(12) United States Patent
Pollack et al.

(10) Patent No.: US 8,951,721 B2
(45) Date of Patent: *Feb. 10, 2015

(54) DROPLET-BASED SURFACE MODIFICATION AND WASHING

(75) Inventors: Michael G. Pollack, San Diego, CA (US); Vamsee K. Pamula, Cary, NC (US); Vijay Srinivasan, Durham, NC (US); Richard B. Fair, Durham, NC (US)

(73) Assignees: Advanced Liquid Logic, Inc., San Diego, CA (US); Duke University, Durham, NC (US)

( * ) Notice: Subject to any disclaimer, the term of this patent is extended or adjusted under 35 U.S.C. 154(b) by 1189 days.

This patent is subject to a terminal disclaimer.

(21) Appl. No.: 12/615,666

(22) Filed: Nov. 10, 2009

(65) Prior Publication Data

US 2010/0116640 A1  May 13, 2010

Related U.S. Application Data

(60) Continuation of application No. 12/113,385, filed on May 1, 2008, now Pat. No. 8,541,176, which is a division of application No. 11/639,736, filed on Dec. 15, 2006, now Pat. No. 7,439,014.

(60) Provisional application No. 60/745,058, filed on Apr. 18, 2006, provisional application No. 60/745,039, filed on Apr. 18, 2006, provisional application No. 60/745,043, filed on Apr. 18, 2006, provisional application No. 60/745,059, filed on Apr. 18, 2006, provisional application No. 60/745,914, filed on Apr. 28, 2006, provisional application No. 60/745,950, filed on Apr. 28, 2006, provisional application No. 60/746,797, filed on May 9, 2006, provisional application No. 60/746,801, filed on May 9, 2006, provisional application No. 60/806,412, filed on Jun. 30, 2006, provisional application No. 60/807,104, filed on Jul. 12, 2006.

(51) Int. Cl.
| | |
|---|---|
| *C12Q 1/00* | (2006.01) |
| *B01L 3/00* | (2006.01) |
| *B01F 13/00* | (2006.01) |
| *B01L 7/00* | (2006.01) |
| *G01N 35/00* | (2006.01) |
| *B01L 3/02* | (2006.01) |

(52) U.S. Cl.
CPC ... *B01L 3/502715* (2013.01); *B01L 2300/0654* (2013.01); *B01L 2200/0673* (2013.01); *B01L 3/502784* (2013.01); *B01L 2300/089* (2013.01); *B01L 2400/0427* (2013.01); *B01L 2200/027* (2013.01); *B01L 7/52* (2013.01); *B01L 7/525* (2013.01); *B01L 2400/0415* (2013.01); *B01L 2300/0816* (2013.01); *G01N 2035/00158* (2013.01); *B01L 2300/0867* (2013.01); *G01N 35/00029* (2013.01); *G01N 2035/00237* (2013.01); *B01L 2400/0448* (2013.01); *B01L 2400/043* (2013.01); *B01L 3/502761* (2013.01); *B01L 2300/0861* (2013.01); *B01L 2400/0406* (2013.01); *B01F 13/0076* (2013.01); *B01L 2400/0442* (2013.01); *B01L 2400/0436* (2013.01); *B01L 2300/0864* (2013.01); *B01L 3/502792* (2013.01); *B01F 13/0071* (2013.01); *B01L 2400/0424* (2013.01); *B01L 2200/0668* (2013.01); *B01L 3/0268* (2013.01); *B01L 2300/1827* (2013.01)

USPC .......................................................... 435/4

(58) Field of Classification Search
None
See application file for complete search history.

(56) References Cited

U.S. PATENT DOCUMENTS

| | | | |
|---|---|---|---|
| 4,636,785 | A | 1/1987 | Le Pesant |
| 5,181,016 | A | 1/1993 | Lee et al. |
| 5,486,337 | A | 1/1996 | Ohkawa |
| 5,770,457 | A | 6/1998 | Stocker et al. |
| 5,980,719 | A | 11/1999 | Cherukuri et al. |
| 6,063,339 | A | 5/2000 | Tisone et al. |
| 6,106,685 | A | 8/2000 | McBride et al. |
| 6,130,098 | A | 10/2000 | Handique et al. |
| 6,294,063 | B1 | 9/2001 | Becker et al. |
| 6,319,668 | B1 | 11/2001 | Nova et al. |
| 6,379,929 | B1 | 4/2002 | Burns et al. |

(Continued)

FOREIGN PATENT DOCUMENTS

| | | |
|---|---|---|
| EP | WO03069380 A1 | 8/2003 |
| EP | WO2004027490 A1 | 4/2004 |

(Continued)

OTHER PUBLICATIONS

Weaver, "Application of Magnetic Microspheres for Pyrosequencing on a Digital Microfludic Platform", web publication, Aug. 29, 2005.*

(Continued)

*Primary Examiner* — Ann Lam
(74) *Attorney, Agent, or Firm* — William A. Barrett; Ward & Smith, P.A.

(57) ABSTRACT

The present invention relates to droplet-based surface modification and washing. According to one embodiment, a method of splitting a droplet is provided, the method including providing a droplet microactuator including a droplet including one or more beads and immobilizing at least one of the one or more beads. The method further includes conducting one or more droplet operations to divide the droplet to yield a set of droplets including a droplet including the one or more immobilized beads and a droplet substantially lacking the one or more immobilized beads.

22 Claims, 21 Drawing Sheets

(56) References Cited

U.S. PATENT DOCUMENTS

| | | |
|---|---|---|
| 6,432,290 B1 | 8/2002 | Harrison et al. |
| 6,461,570 B2 | 10/2002 | Ishihara et al. |
| 6,473,492 B2 | 10/2002 | Prins |
| 6,538,823 B2 | 3/2003 | Kroupenkine et al. |
| 6,545,815 B2 | 4/2003 | Kroupenkine et al. |
| 6,565,727 B1 | 5/2003 | Shenderov |
| 6,629,826 B2 | 10/2003 | Yoon et al. |
| 6,665,127 B2 | 12/2003 | Bao et al. |
| 6,761,962 B2 | 7/2004 | Bentsen et al. |
| 6,773,566 B2 | 8/2004 | Shenderov |
| 6,790,011 B1 | 9/2004 | Le Pesant et al. |
| 6,846,638 B2 | 1/2005 | Shipwash |
| 6,911,132 B2 | 6/2005 | Pamula et al. |
| 6,924,792 B1 | 8/2005 | Jessop |
| 6,949,176 B2 | 9/2005 | Vacca et al. |
| 6,958,132 B2 | 10/2005 | Chiou et al. |
| 6,977,033 B2 | 12/2005 | Becker et al. |
| 6,989,234 B2 | 1/2006 | Kolar et al. |
| 7,052,244 B2 | 5/2006 | Fouillet et al. |
| 7,163,612 B2 | 1/2007 | Sterling et al. |
| 7,189,359 B2 | 3/2007 | Yuan et al. |
| 7,189,560 B2 | 3/2007 | Kim et al. |
| 7,211,223 B2 | 5/2007 | Fouillet et al. |
| 7,255,780 B2 | 8/2007 | Shenderov |
| 7,328,979 B2 | 2/2008 | Decre et al. |
| 7,329,545 B2 | 2/2008 | Pamula et al. |
| 7,439,014 B2 | 10/2008 | Pamula et al. |
| 7,458,661 B2 | 12/2008 | Kim et al. |
| 7,531,072 B2 | 5/2009 | Roux et al. |
| 7,547,380 B2 | 6/2009 | Velev |
| 7,569,129 B2 * | 8/2009 | Pamula et al. ............... 204/450 |
| 7,641,779 B2 | 1/2010 | Becker et al. |
| 7,727,466 B2 | 6/2010 | Meathrel et al. |
| 7,727,723 B2 * | 6/2010 | Pollack et al. ............... 435/6.11 |
| 7,759,132 B2 | 7/2010 | Pollack et al. |
| 7,763,471 B2 | 7/2010 | Pamula et al. |
| 7,815,871 B2 | 10/2010 | Pamula et al. |
| 7,816,121 B2 * | 10/2010 | Pollack et al. ............. 435/286.5 |
| 7,822,510 B2 | 10/2010 | Paik et al. |
| 7,851,184 B2 * | 12/2010 | Pollack et al. ............... 435/91.2 |
| 7,875,160 B2 | 1/2011 | Jary |
| 7,901,947 B2 | 3/2011 | Pollack et al. |
| 7,919,330 B2 | 4/2011 | De Guzman et al. |
| 7,922,886 B2 | 4/2011 | Fouillet et al. |
| 7,943,030 B2 | 5/2011 | Shenderov |
| 7,989,056 B2 | 8/2011 | Plissonnier et al. |
| 7,998,436 B2 | 8/2011 | Pollack |
| 8,007,739 B2 | 8/2011 | Pollack et al. |
| 8,041,463 B2 | 10/2011 | Pollack et al. |
| 8,048,628 B2 | 11/2011 | Pollack et al. |
| 8,075,754 B2 | 12/2011 | Sauter-Starace et al. |
| 8,137,917 B2 | 3/2012 | Pollack et al. |
| 8,147,668 B2 | 4/2012 | Pollack et al. |
| 8,221,605 B2 | 7/2012 | Pollack et al. |
| 8,236,156 B2 | 8/2012 | Sarrut et al. |
| 8,287,711 B2 | 10/2012 | Pollack et al. |
| 8,304,253 B2 | 11/2012 | Yi et al. |
| 8,313,698 B2 | 11/2012 | Pollack et al. |
| 8,342,207 B2 | 1/2013 | Raccurt et al. |
| 8,349,276 B2 | 1/2013 | Pamula et al. |
| 8,388,909 B2 | 3/2013 | Pollack et al. |
| 8,389,297 B2 * | 3/2013 | Pamula et al. ................ 436/526 |
| 8,394,249 B2 | 3/2013 | Pollack et al. |
| 8,470,606 B2 * | 6/2013 | Srinivasan et al. ............ 436/180 |
| 2002/0005354 A1 | 1/2002 | Spence et al. |
| 2002/0036139 A1 | 3/2002 | Becker et al. |
| 2002/0043463 A1 | 4/2002 | Shenderov |
| 2002/0058332 A1 | 5/2002 | Quake et al. |
| 2002/0093651 A1 | 7/2002 | Roe |
| 2002/0128546 A1 | 9/2002 | Silver |
| 2002/0143437 A1 | 10/2002 | Handique et al. |
| 2002/0168671 A1 | 11/2002 | Burns et al. |
| 2002/0172969 A1 | 11/2002 | Burns et al. |
| 2003/0006140 A1 | 1/2003 | Vacca et al. |
| 2003/0012483 A1 | 1/2003 | Ticknor et al. |
| 2003/0012699 A1 | 1/2003 | Moore et al. |
| 2003/0082081 A1 | 5/2003 | Fouillet et al. |
| 2003/0103021 A1 | 6/2003 | Young et al. |
| 2003/0119057 A1 | 6/2003 | Gascoyne et al. |
| 2003/0164295 A1 | 9/2003 | Sterling |
| 2003/0183525 A1 | 10/2003 | Elrod et al. |
| 2003/0198576 A1 | 10/2003 | Coyne et al. |
| 2003/0205632 A1 | 11/2003 | Kim et al. |
| 2003/0206351 A1 | 11/2003 | Kroupenkine |
| 2003/0224528 A1 | 12/2003 | Chiou et al. |
| 2003/0227100 A1 | 12/2003 | Chandross et al. |
| 2004/0007377 A1 | 1/2004 | Fouillet et al. |
| 2004/0031688 A1 | 2/2004 | Shenderov |
| 2004/0042721 A1 | 3/2004 | Kroupenkine et al. |
| 2004/0055536 A1 | 3/2004 | Kolar et al. |
| 2004/0055891 A1 | 3/2004 | Pamula et al. |
| 2004/0058450 A1 | 3/2004 | Pamula et al. |
| 2004/0091392 A1 | 5/2004 | McBride et al. |
| 2004/0136876 A1 | 7/2004 | Fouillet et al. |
| 2004/0231987 A1 | 11/2004 | Sterling et al. |
| 2005/0048581 A1 | 3/2005 | Chiu et al. |
| 2005/0056569 A1 | 3/2005 | Yuan et al. |
| 2005/0100675 A1 | 5/2005 | Mao et al. |
| 2005/0106742 A1 | 5/2005 | Wahl |
| 2005/0148042 A1 | 7/2005 | Prestwich et al. |
| 2005/0158755 A1 | 7/2005 | Lee et al. |
| 2005/0179746 A1 | 8/2005 | Roux et al. |
| 2005/0227349 A1 | 10/2005 | Kim et al. |
| 2005/0287572 A1 | 12/2005 | Mathies et al. |
| 2006/0021875 A1 | 2/2006 | Griffith et al. |
| 2006/0054503 A1 | 3/2006 | Pamula et al. |
| 2006/0068450 A1 | 3/2006 | Combette et al. |
| 2006/0164490 A1 | 7/2006 | Kim et al. |
| 2006/0194331 A1 | 8/2006 | Pamula et al. |
| 2006/0231398 A1 | 10/2006 | Sarrut et al. |
| 2006/0254933 A1 | 11/2006 | Adachi et al. |
| 2007/0023292 A1 | 2/2007 | Kim et al. |
| 2007/0037294 A1 | 2/2007 | Pamula et al. |
| 2007/0045117 A1 | 3/2007 | Pamula et al. |
| 2007/0064990 A1 | 3/2007 | Roth |
| 2007/0086927 A1 | 4/2007 | Natarajan et al. |
| 2007/0207513 A1 | 9/2007 | Sorensen et al. |
| 2007/0217956 A1 | 9/2007 | Pamula et al. |
| 2007/0241068 A1 | 10/2007 | Pamula et al. |
| 2007/0242105 A1 | 10/2007 | Srinivasan et al. |
| 2007/0242111 A1 | 10/2007 | Pamula et al. |
| 2007/0243634 A1 | 10/2007 | Pamula et al. |
| 2007/0267294 A1 | 11/2007 | Shenderov |
| 2007/0275415 A1 * | 11/2007 | Srinivasan et al. ............. 435/7.4 |
| 2008/0006535 A1 | 1/2008 | Paik et al. |
| 2008/0038810 A1 | 2/2008 | Pollack et al. |
| 2008/0044893 A1 | 2/2008 | Pollack et al. |
| 2008/0044914 A1 | 2/2008 | Pamula et al. |
| 2008/0050834 A1 | 2/2008 | Pamula et al. |
| 2008/0053205 A1 | 3/2008 | Pollack et al. |
| 2008/0105549 A1 | 5/2008 | Pamela et al. |
| 2008/0124252 A1 | 5/2008 | Marchand et al. |
| 2008/0142376 A1 | 6/2008 | Fouillet et al. |
| 2008/0151240 A1 | 6/2008 | Roth |
| 2008/0210558 A1 | 9/2008 | Sauter-Starace et al. |
| 2008/0247920 A1 | 10/2008 | Pollack et al. |
| 2008/0264797 A1 | 10/2008 | Pamula et al. |
| 2008/0274513 A1 | 11/2008 | Shenderov et al. |
| 2008/0302431 A1 | 12/2008 | Marchand et al. |
| 2008/0305481 A1 | 12/2008 | Whitman et al. |
| 2009/0014394 A1 | 1/2009 | Yi et al. |
| 2009/0042319 A1 | 2/2009 | De Guzman et al. |
| 2009/0127123 A1 | 5/2009 | Raccurt et al. |
| 2009/0134027 A1 | 5/2009 | Jary |
| 2009/0142564 A1 | 6/2009 | Plissonnier et al. |
| 2009/0155902 A1 | 6/2009 | Pollack et al. |
| 2009/0192044 A1 | 7/2009 | Fouillet |
| 2009/0260988 A1 | 10/2009 | Pamula et al. |
| 2009/0263834 A1 | 10/2009 | Sista et al. |
| 2009/0280251 A1 | 11/2009 | De Guzman et al. |
| 2009/0280475 A1 | 11/2009 | Pollack et al. |
| 2009/0280476 A1 | 11/2009 | Srinivasan et al. |
| 2009/0288710 A1 | 11/2009 | Viovy et al. |
| 2009/0291433 A1 | 11/2009 | Pollack et al. |

(56) References Cited

U.S. PATENT DOCUMENTS

| | | |
|---|---|---|
| 2010/0025242 A1 | 2/2010 | Pamula et al. |
| 2010/0096266 A1 | 4/2010 | Kim et al. |
| 2010/0116640 A1 | 5/2010 | Pamula et al. |
| 2010/0140093 A1 | 6/2010 | Pamula et al. |
| 2010/0143963 A1 | 6/2010 | Pollack |
| 2010/0213074 A1 | 8/2010 | Mousa et al. |
| 2010/0258441 A1 | 10/2010 | Sista et al. |
| 2010/0279374 A1 | 11/2010 | Sista et al. |
| 2010/0291578 A1 | 11/2010 | Pollack et al. |
| 2011/0100823 A1 | 5/2011 | Pollack et al. |
| 2011/0114490 A1 | 5/2011 | Pamula et al. |
| 2011/0180571 A1 | 7/2011 | Srinivasan et al. |
| 2011/0186433 A1 | 8/2011 | Pollack et al. |
| 2011/0203930 A1 | 8/2011 | Pamula et al. |
| 2011/0209998 A1 | 9/2011 | Shenderov |
| 2012/0018306 A1 | 1/2012 | Srinivasan et al. |
| 2012/0132528 A1 | 5/2012 | Shenderov et al. |
| 2012/0165238 A1 | 6/2012 | Pamula et al. |

FOREIGN PATENT DOCUMENTS

| | | |
|---|---|---|
| FI | WO9954730 A1 | 10/1999 |
| JP | 2006078225 A | 3/2006 |
| WO | WO9915876 A1 | 4/1999 |
| WO | WO9917093 A1 | 4/1999 |
| WO | 0069565 A1 | 11/2000 |
| WO | 0073655 A1 | 12/2000 |
| WO | 2004029585 A1 | 4/2004 |
| WO | 2004030820 | 4/2004 |
| WO | 2005047696 A1 | 5/2005 |
| WO | 2005069015 | 7/2005 |
| WO | 2006003292 | 1/2006 |
| WO | 2006013303 A1 | 2/2006 |
| WO | WO2006026351 A1 | 3/2006 |
| WO | 2006070162 A1 | 7/2006 |
| WO | 2006081558 | 8/2006 |
| WO | 2006124458 A2 | 11/2006 |
| WO | 2006127451 A2 | 11/2006 |
| WO | 2006134307 A1 | 12/2006 |
| WO | 2006138543 | 12/2006 |
| WO | 2007003720 A1 | 1/2007 |
| WO | 2007012638 A1 | 2/2007 |
| WO | 2007033990 A1 | 3/2007 |
| WO | 2007048111 | 4/2007 |
| WO | 2007120240 A2 | 10/2007 |
| WO | 2007120241 A2 | 10/2007 |
| WO | 2007123908 A2 | 11/2007 |
| WO | 2008051310 A2 | 5/2008 |
| WO | 2008055256 A3 | 5/2008 |

OTHER PUBLICATIONS

Dewey A, Srinivasan V, Icoz E, "Visual modeling and design of microelectromechanical system transducers", Microelectronics Journal, vol. 32, pp. 373-381, Apr. 2001.

Dewey A, Srinivasan V, Icoz E, "Towards a visual modeling approach to designing micro electromechanical system transducers," Journal of Micromechanics and Microengineering, vol. 9, pp. 332-340, Dec. 1999.

R.B. Fair, A. Khlystov, T. Tailor, V. Ivanov, R.D. Evans, V. Srinivasan, V. Pamula, M.G. Pollack, P.B. Griffin, and J. Zhoud, "Chemical and Biological Applications of Digital Microfluidic Devices", IEEE Design and Test of Computers, vol. 24(1): pp. 10-24 Jan.-Feb. 2007.

R.B. Fair, A. Khlystov, V. Srinivasan, V. K. Pamula, K.N. Weaver, "Integrated chemical/biochemical sample collection, pre-concentration, and analysis on a digital microfluidic lab-on-a-chip platform," Lab-on-a-Chip: Platforms, Devices, and Applications, Conf. 5591, SPIE Optics East, Philadelphia, Oct. 25-28, 2004.

E. Verpoorte, "Beads and chips: new recipes for analysis," Lab on a Chip (LOC), vol. 3, pp. 60N-68N, 2003.

R.B. Fair, V. Srinivasan, H. Ren, P. Paik, V.K. Pamula, M.G. Pollack, "Electrowetting-based On-Chip Sample Processing for Integrated Microfluidics," IEEE Inter. Electron Devices Meeting (IEDM), pp. 32.5.1-32.5.4, 2003.

Phil Paik, Vamsee K. Pamula, and K. Chakrabarty, "Thermal effects on Droplet Transport in Digital Microfluidics with Applications to Chip Cooling Processing for Integrated Microfluidics," International Conference on Thermal, Mechanics, and Thermomechanical Phenomena in Electronic Systems (ITherm), pp. 649-654, 2004.

Phil Paik, Vamsee K. Pamula, and Richard B. Fair, "Rapid droplet mixers for digital microfluidic systems," Lab on a Chip, vol. 3, pp. 253-259, 2003.

Phil Paik, Vamsee K. Pamula, Michael G. Pollack and Richard B. Fair, "Electrowetting-based droplet mixers for microfluidic systems", Lab on a Chip (LOC), vol. 3, pp. 28-33, 2003.

Vamsee K. Pamula and Krishnendu Chakrabarty, "Cooling of integrated circuits using droplet-based microfluidics," Proc. ACM Great Lakes Symposium on VLSI, pp. 84-87, Apr. 2003.

V.K. Pamula, V. Srinivasan, H. Chakrapani, R.B. Fair, E.J. Toone, "A droplet-based lab-on-a-chip for colorimetric detection of nitroaromatic explosives," Proceedings of Micro Electro Mechanical Systems, pp. 722-725, 2005.

M. G. Pollack, P. Y. Paik, A. D. Shenderov, V. K. Pamula, F. S. Dietrich, and R. B. Fair, "Investigation of electrowetting-based microfluidics for real-time PCR applications," UTAS 2003.

Pollack et al., "Electrowetting-Based Microfluidics for High-Throughput Screening," smallTalk2001 Conference Program Abstract (Aug. 2001), p. 149, San Diego.

Hong Ren, Vijay Srinivasan, Michael G. Pollack, and Richard B. Fair, "Automated electrowetting-based droplet dispensing with good reproducibility," Proc. Micro Total Analysis Systems (mTAS), pp. 993-996, 2003.

Hong Ren, Vijay Srinivasan, and Richard B. Fair, "Design and testing of an interpolating mixing architecture for electrowetting-based droplet-on-chip chemical dilution", Transducers 2003, pp. 619-622, 2003.

Vijay Srinivasan, Vamsee K. Pamula, Richard B. Fair, "An integrated digital microfluidic lab-on-a-chip for clinical diagnostics on human physiological fluids," Lab on a Chip, vol. 4, pp. 310-315, 2004.

Vijay Srinivasan, Vamsee K. Pamula, Richard B. Fair, "Droplet-based microfluidic lab-on-a-chip for glucose detection," Analytica Chimica Acta, vol. 507, No. 1, pp. 145-150, 2004.

V. Srinivasan, V.K. Pamula, P. Paik, and R.B. Fair, "Protein Stamping for MALDI Mass Spectrometry Using an Electrowetting-based Microfluidic Platform," Lab-on-a-Chip: Platforms, Devices, and Applications, Conf. 5591, SPIE Optics East, Philadelphia, Oct. 25-28, 2004.

Vijay Srinivasan, Vamsee K. Pamula, Michael G. Pollack, and Richard B. Fair, "Clinical diagnostics on human whole blood, plasma, serum, urine, saliva, sweat, and tears on a digital microfluidic platform," Proc. Micro Total Analysis Systems (mTAS), pp. 1287-1290, 2003.

Vijay Srinivasan, Vamsee K. Pamula, Michael G. Pollack, and Richard B. Fair, "A digital microfluidic biosensor for multianalyte detection", Proc. IEEE 16th Micro Electro Mechanical Systems Conference, pp. 327-330, 2003.

Vijay Srinivasan, Vamsee K. Pamula, K. Divakar Rao, Michael G. Pollack, Joseph A. Izatt, and Richard B. Fair, "3-D imaging of moving droplets for microfluidics using optical coherence tomography," Proc. Micro Total Analysis Systems (mTAS), pp. 1303-1306, 2003.

F. Su, S. Ozev and K. Chakrabarty, "Testing of droplet-based microelectrofluidic systems", Proc. IEEE International Test Conference, pp. 1192-1200, 2003.

Nicole Weaver, "Application of Magnetic Microspheres for Pyrosequencing on a Digital Microfluidic Platform", Aug. 29, 2005. PCT International Preliminary Report on Patentability for PCT/US05/030247 dated Feb. 28, 2007.

"Chip mixes droplets faster", MIT Technology Review, Oct. 2003.

"Chip Juggles Droplets", Technology Research News, Sep. 4-11, 2002.

"Laboratory on a Chip", Popular Mechanics, Mar. 2002.

"Lab-on-a-Chip Technology May Present New ESD Challenges", Electrostatic Discharge Journal, Mar. 2002.

"Making materials fit the future: accommodating relentless technological requirements means researchers must recreate and

(56) References Cited

OTHER PUBLICATIONS reconfigure materials, frequently challenging established laws of physics, while keeping an eye on Moore's law", R&D Magazine, Dec. 2001.

Y. Wang et al., "Effcient in-droplet separation of magnetic particles for digital microfluidics," Journal of Micromechanics and Microengineering, vol. 17, pp. 2148-2156 (2007).

Lehmann et al., "Droplet-Based DNA Purification in a Magnetic Lab-on-a-Chip," Angewandte Chemie, vol. 45, pp. 3062-3067, 2006.

N. Pamme, "Magnetism and microfluidics," Lab on a Chip (LOC), vol. 6, pp. 24-38, 2006.

R. Sista, "Development of a Digital Microfluidic Lab-on-a-Chip for Automated Immunoassay with Magnetically Responsive Beads", PhD Thesis, Department of Chemical Engineering, Florida State University, 2007.

Vijay Srinivasan, Anand Jog and Richard B. Fair, "Scalable Macromodels for Microelectromechanical Systems," Technical Proc. 2001 Int. Conf. on Modeling and Simulation of Microsystems, pp. 72-75, 2001.

Chakrabarty, "Automated Design of Microfluidics-Based Biochips: connecting Biochemistry of Electronics CAD", IEEE International Conference on Computer Design, San Jose, CA, Oct. 1-4, 2006, 93-100.

Chakrabarty et al., "Design Automation Challenges for Microfluidics-Based Biochips", DTIP of MEMS & MOEMS, Montreux, Switzerland, Jun. 1-3, 2005.

Chakrabarty et al., "Design Automation for Microfluidics-Based Biochips", ACM Journal on Engineering Technologies in Computing Systems, 1(3), Oct. 2005, 186-223.

Chakrabarty, "Design, Testing, and Applications of Digital Microfluidics-Based Biochips", Proceedings of the 18th International Conf. On VLSI held jointly with 4th International Conf. on Embedded Systems Design (VLSID'05), IEEE, Jan. 3-7, 2005.

Chen et al., "Development of Mesoscale Actuator Device with Micro Interlocking Mechanism", J. Intelligent Material Systems and Structures, vol. 9, No. 4, Jun. 1998, pp. 449-457.

Chen et al., "Mesoscale Actuator Device with Micro Interlocking Mechanism", Proc. IEEE Micro Electro Mechanical Systems Workshop, Heidelberg, Germany, Jan. 1998, pp. 384-389.

Chen et al., "Mesoscale Actuator Device: Micro Interlocking Mechanism to Transfer Macro Load", Sensors and Actuators, vol. 73, Issues 1-2, Mar. 1999, pp. 30-36.

Fair et al., "A Micro-Watt Metal-Insulator-Solution-Transport (MIST) Device for Scalable Digital Bio-Microfluidic Systems", IEEE IEDM Technical Digest, 2001, 16.4.1-4.

Fair et al., "Advances in droplet-based bio lab-on-a-chip", BioChips 2003, Boston, 2003.

Fair et al., "Bead-Based and Solution-Based Assays Performed on a Digital Microfluidic Platform", Biomedical Engineering Society (BMES) Fall Meeting, Baltimore, MD, Oct. 1, 2005.

Fair, "Biomedical Applications of Electrowetting Systems", 5th International Electrowetting Workshop, Rochester, NY, May 31, 2006.

Fair et al., "Chemical and biological pathogen detection in a digital microfluidic platform", DARPA Workshop on Microfluidic Analyzers for DoD and National Security Applications, Keystone, CO, 2006.

Fair, "Droplet-based microfluidic Genome sequencing", NHGRI PI's meeting, Boston, 2005.

Fouillet et al., "Design and Validation of a Complex Generic Fluidic Microprocessor Based on EWOD Droplet for Biological Applications", 9th International Conference on Miniaturized Systems for Chem and Life Sciences, Boston, MA, Oct. 9-13, 2005, 58-60.

Jun et al., "Valveless Pumping using Traversing Vapor Bubbles in Microchannels", J. Applied Physics, vol. 83, No. 11, Jun. 1998, pp. 5658-5664.

Kim et al., "MEMS Devices Based on the Use of Surface Tension", Proc. Int. Semiconductor Device Research Symposium (ISDRS'99), Charlottesville, VA, Dec. 1999, pp. 481-484.

Kim, "Microelectromechanical Systems (MEMS) at the UCLA Micromanufacturing Lab", Dig. Papers, Int. Microprocesses and Nanotechnology Conf. (MNC'98), Kyungju, Korea, Jul. 1998, pp. 54-55.

Kim et al., "Micromachines Driven by Surface Tension", AIAA 99-3800, 30th AIAA Fluid Dynamics Conference, Norfolk, VA, (Invited lecture), Jun. 1999, pp. 1-6.

Lee et al., "Microactuation by Continuous Electrowetting Phenomenon and Silicon Deep Rie Process", Proc. MEMS (DSC-vol. 66) ASME Int. Mechanical Engineering Congress and Exposition, Anaheim, CA, Nov. 1998, 475-480.

Lee et al., "Liquid Micromotor Driven by Continuous Electrowetting", Proc. IEEE Micro Electro Mechanical Systems Workshop, Heidelberg, Germany, Jan. 1998, pp. 538-543.

Lee et al., "Theory and Modeling of Continuous Electrowetting Microactuation", Proc. MEMS (MEMS-vol. 1), ASME Int. Mechanical Engineering Congress and Exposition, Nashville, TN, Nov. 1999, pp. 397-403.

Paik, "Adaptive Hot-Spot Cooling of Integrated Circuits Using Digital Microfluidics", Dissertation, Dept. of Electrical and Computer Engineering, Duke University, Apr. 25, 2006, 1-188.

Paik et al., "Adaptive hot-spot cooling of integrated circuits using digital microfluidics", Proceedings ASME International Mechanical Engineering Congress and Exposition, Orlando, Florida, USA. IMECE2005-81081, Nov. 5-11, 2005, 1-6.

Paik et al., "Coplanar Digital Microfluidics Using Standard Printed Circuit Board Processes", 9th International Conference on Miniaturized Systems for Chemistry and Life Sciences (MicroTAS), Boston, MA; Poster, 2005.

Paik et al., "Coplanar Digital Microfluidics Using Standard Printed Circuit Board Processes", 9th Int'l Conf. on Miniaturized Systems for Chemistry and Life Sciences, Boston, MA, Oct. 9-13, 2005, 566-68.

Paik et al., "Droplet-Based Hot Spot Cooling Using Topless Digital Microfluidics on a Printed Circuit Board", Int'l Workshops on Thermal Investigations of ICs and Systems (Therminic), 2005, 278-83.

Paik et al., "Rapid Droplet Mixers for Digital Microfluidic Systems", Masters Thesis, Duke Graduate School., 2002, 1-82.

Pamula, "A digital microfluidic platform for multiplexed explosive detection", Chapter 18, Electronics Noses and Sensors for the Detection of Explosives, Eds., J.W. Gardner and J. Yinon, Kluwer Academic Publishers, 2004.

Pamula et al., "Digital microfluidic lab-on-a-chip for protein crystallization", 5th Protein Structure Initiative "Bottlenecks" Workshop, NIH, Bethesda, MD, Apr. 13-14, 2006, I-16.

Pamula et al., "Digital Microfluidics Platform for Lab-on-a-chip applications", Duke University Annual Post Doctoral Research Day, 2002.

Pamula et al., "Microfluidic electrowetting-based droplet mixing", IEEE, 2002, 8-10.

Pamula et al. (Co-Chair, "Digital Microfluidics for Lab-on-a-Chip Applications", "Emerging CAD Challenges for Biochip Design" Workshop, Conference on Design, Automation, and Test in Europe (DATE), Munich, Germany, Advance Programme, 2006, pp. 85-87.

Pollack, et al., "Electrowetting-Based Actuation of Droplets for Integrated Microfluidics", Lab on a Chip (LOC), vol. 2, 2002, 96-101.

Pollack et al., "Electrowetting-based actuation of liquid droplets for microfluidic applications", Appl. Phys. Letters, vol. 77, No. 11, Sep. 11, 2000, 1725-1726.

Pollack, "Electrowetting-based Microactuation of Droplets for Digital Microfluidics", PhD Thesis, Department of Electrical and Computer Engineering, Duke University, 2001.

Ren et al., "Automated on-chip droplet dispensing with volume control by electro-wetting actuation and capacitance metering", Sensors and Actuators B: Chemical, vol. 98, Mar. 2004, 319-327.

Ren et al., "Dynamics of electro-wetting droplet transport", Sensors and Actuators B (Chemical), vol. B87, No. 1, Nov. 15, 2002, 201-206.

Ren et al., "Micro/Nano Liter Droplet Formation and Dispensing by Capacitance Metering and Electrowetting Actuation", IEEE-NANO, 2002, 369-372.

Sherman et al., "Flow Control by Using High-Aspect-Ratio, In-Plane Microactuators", Sensors and Actuators, vol. 73, 1999, pp. 169-175.

(56) References Cited

OTHER PUBLICATIONS

Sherman et al., "In-Plane Microactuator for Fluid Control Application", Proc. IEEE Micro Electro Mechanical Systems Workshop, Heidelberg, Germany, Jan. 1998, pp. 454-459.

Srinivasan, "A Digital Microfluidic Lab-on-a-Chip for Clinical Diagnostic Applications", Ph.D. thesis, Dept of Electrical and Computer Engineering, Duke University, 2005.

Su et al., "Yield Enhancement of Digital Microfluidics-Based Biochips Using Space Redundancy and Local Reconfiguration", Proc. Design, Automation and Test in Europe (DATE) Conf., IEEE, 2005, 1196-1201.

Sudarsan et al., "Printed circuit technology for fabrication of plastic based microfluidic devices", Analytical Chemistry vol. 76, No. 11, Jun. 1, 2004, Previously published on-line, May 2004, 3229-3235.

Wang et al., "Droplet-based micro oscillating-flow PCR chip", J. Micromechanics and Microengineering, vol. 15, 2005, 1369-1377.

Xu et al., "Droplet-Trace-Based Array Partitioning and a Pin Assignment Algorithm for the Automated Design of Digital Microfluidic Biochips", CODES, 2006, 112-117.

Yao et al., "Spot Cooling Using Thermoelectric Microcooler", Proc. 18th Int. Thermoelectric Conf, Baltimore, VA, pp. 256-259, Aug. 1999.

Yi et al., "Channel-to-droplet extractions for on-chip sample preparation", Solid-State Sensor, Actuators and Microsystems Workshop (Hilton Head '06), Hilton Head Island, SC, Jun. 2006, 128-131.

Yi et al., "Characterization of electrowetting actuation on addressable single-side coplanar electrodes", Journal of Micromechanics and Microengineering, vol. 16., Oct. 2006, 2053-2059.

Yi et al., "EWOD Actuation with Electrode-Free Cover Plate", Digest of Tech. papers, 13th International Conference on Solid-State Sensors, Actuators and Microsystems (Transducers '05), Seoul, Korea, Jun. 5-9, 2005, 89-92.

Yi et al., "Geometric surface modification of nozzles for complete transfer of liquid drops", Solid-State Sensor, Actuator and Microsystems Workshop, Hilton Head Island, South Carolina, Jun. 6-10, 2004, 164-167.

Yi, "Soft Printing of Biological Liquids for Micro-arrays: Concept, Principle, Fabrication, and Demonstration", Ph.D. dissertation, UCLA, 2004.

Yi et al., "Soft Printing of Droplets Digitized by Electrowetting", Transducers 12th Int'l Conf. on Solid State Sensors, Actuators and Microsystems, Boston, Jun. 8-12, 2003, 1804-1807.

Yi et al., "Soft Printing of Droplets Pre-Metered by Electrowetting", Sensors and Actuators A: Physical, vol. 114, Jan. 2004, 347-354.

Zeng et al., "Actuation and Control of Droplets by Using Electrowetting-on-Dielectric", Chin. Phys. Lett., vol. 21(9), 2004, 1851-1854.

Zhao et al., "In-droplet particle separation by travelling wave dielectrophoresis (twDEP) and EWOD", Solid-State Sensor, Actuators and Microsystems Workshop (Hilton Head '06), Hilton Head Island, SC, Jun. 2006, 181-184.

Zhao et al., "Micro air bubble manipulation by electrowetting on dielectric (EWOD): transporting, splitting, merging and eliminating of bubbles", Lab on a chip, vol. 7, 2007, First published as an Advance Article on the web, Dec. 4, 2006, 273-280.

Su et al., "Testing of droplet-based microelectrofluidic systems", Proc. IEEE International Test Conference, pp. 1192-1200, 2003.

PCT International Search Report and Written Opinion for PCT/US2006/047486 dated May 2, 2008.

PCT International Preliminary Report on Patentability for PCT/US2006/047486 dated May 2, 2008.

\* cited by examiner

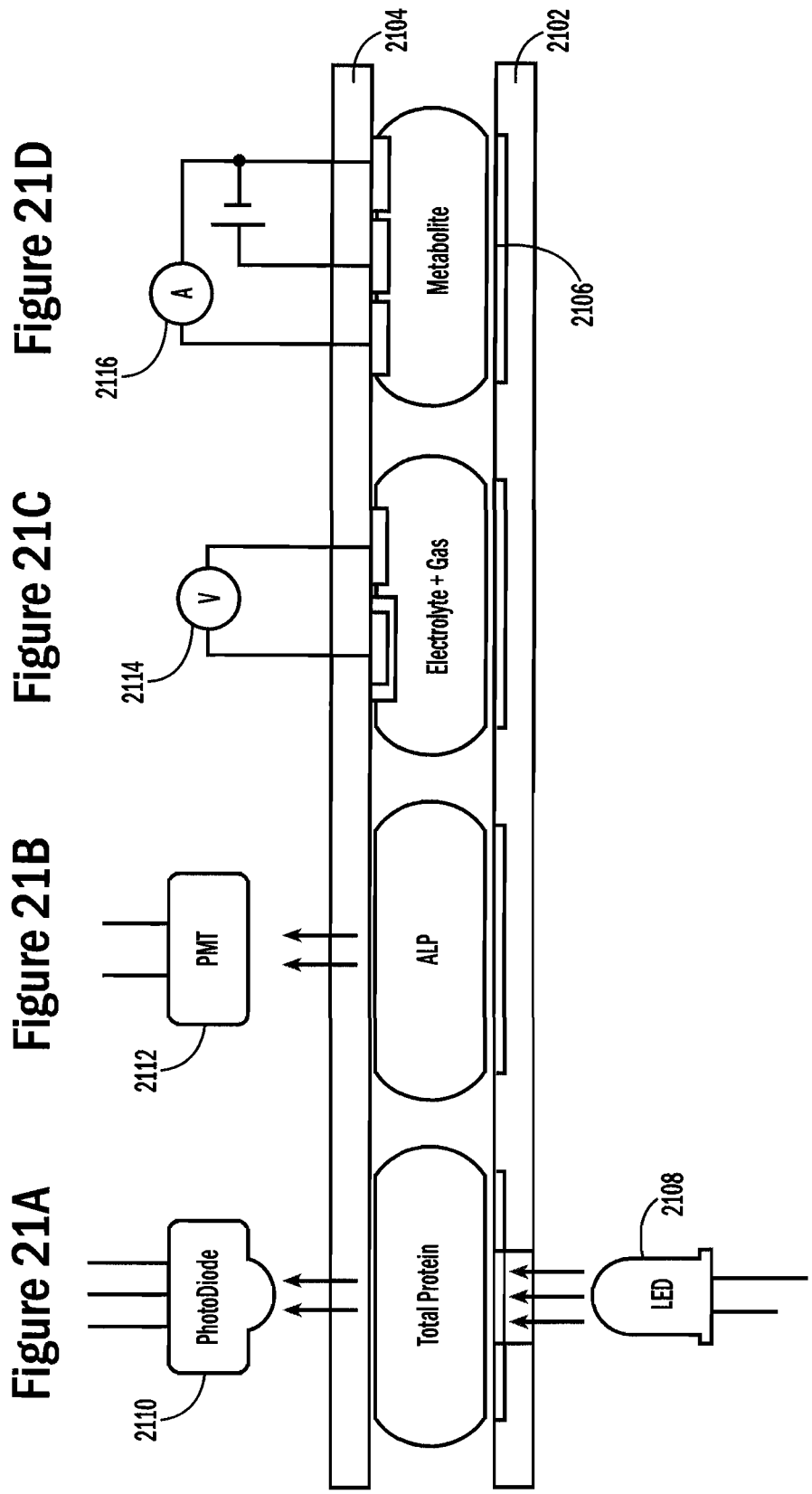

DROPLET-BASED SURFACE MODIFICATION AND WASHING

2 RELATED APPLICATIONS

This application is a continuation of and incorporates by reference co-pending U.S. patent application Ser. No. 12/113,385, entitled "Droplet-Based Surface Modification and Washing" filed on May 1, 2008, which is a divisional of and incorporates by reference U.S. patent application Ser. No. 11/639,736, entitled "Droplet-Based Surface Modification and Washing" filed on Dec. 15, 2006 (now U.S. Pat. No. 7,439,014 issued Oct. 21, 2008), and which claims priority to and incorporates by reference related provisional U.S. Patent Application Nos. 60/745,058, entitled "Filler Fluids for Droplet-Based Microfluidics" filed on Apr. 18, 2006; 60/745,039, entitled "Apparatus and Methods for Droplet-Based Blood Chemistry," filed on Apr. 18, 2006; 60/745,043, entitled "Apparatus and Methods for Droplet-Based PCR," filed on Apr. 18, 2006; 60/745,059, entitled "Apparatus and Methods for Droplet-Based Immunoassay," filed on Apr. 18, 2006; 60/745,914, entitled "Apparatus and Method for Manipulating Droplets with a Predetermined Number of Cells" filed on Apr. 28, 2006; 60/745,950, entitled "Apparatus and Methods of Sample Preparation for a Droplet Microactuator," filed on Apr. 28, 2006; 60/746,797 entitled "Portable Analyzer Using Droplet-Based Microfluidics," filed on May 9, 2006; 60/746,801, entitled "Apparatus and Methods for Droplet-Based Immuno-PCR," filed on May 9, 2006; 60/806,412, entitled "Systems and Methods for Droplet Microactuator Operations," filed on Jun. 30, 2006; and 60/807,104, entitled "Method and Apparatus for Droplet-Based Nucleic Acid Amplification," filed on Jul. 12, 2006.

1 GRANT INFORMATION

This invention was made with government support under 1 R21 HG003706-01; 5 U01 AI066590-02; and 1 R43 CA114993-01A2, each awarded by the National Institutes of Health of the United States. The United States Government has certain rights in the invention.

3 FIELD OF THE INVENTION

The invention relates to a droplet microactuator and to systems, apparatuses and methods employing the droplet microactuator for executing various protocols using discrete droplets. More particularly, the invention relates to droplet-based surface modification and washing.

4 BACKGROUND OF THE INVENTION

The capability to rapidly conduct biochemical and other assays is critical in a wide variety of fields. For example, rapid and accurate diagnosis of infectious disease is crucial both for the effective management of disease in individual subjects and for ameliorating the public health problems of multi-drug resistant pathogens and community acquired infections.

Current PCR-based DNA amplification methods suffer from a number of drawbacks including high reagent costs, labor intensity and susceptibility to cross-contamination. Furthermore, compared to culture, PCR tests are less capable of simultaneously assaying multiple species, virulence factors, and drug resistant markers. They often lack sensitivity and cost-effective quantification of the pathogen. There is a need in the art for improved devices for nucleic acid detection that would overcome these limitations while also miniaturizing and automating the technique so that these assays could potentially be applied at the point-of-sample collection with minimal training.

Nucleic acid sequencing is becoming increasingly common in a variety of fields, such as whole genome sequencing, diagnostics, pharmacogenomics, and forensics. However, the sequencing field has been hampered by the expensive nature of sequencing machines. The development of inexpensive, high-throughput testing systems is critically important to the spread of genetic testing and the many advantages that are associated with it. There is thus a need for new technological platforms that allow one to quickly and reliably sequence nucleic acids at a reasonable cost. The invention described herein provides an inexpensive, droplet-based sequencing system.

Immunoassays are widely used for clinical diagnostics and constitute more than a $3 billion market in the US alone. Immunoassays are among the most sensitive and specific methods that are routinely used in a clinical laboratory. Immunoassays make use of the high-affinity and specificity in binding between an antigen and its homologous antibody to detect and quantify the antigen in a sample matrix. Heterogeneous immunoassays such as ELISA (Enzyme-Linked Immunosorbent Assay) are among the most sensitive and specific clinical analysis methods, and have been widely used for identification of a large class of antigens and antibodies. For example, immunoassays are performed, among other things, for identification of cardiac markers, tumor markers, drugs, hormones, and infectious diseases.

Small sample consumption, faster analysis, and complete automation are three highly desirable features that require continual improvement in any clinical analyzer. Although state-of-the-art laboratory immunoassay analyzers offer good automation and throughput, they require a significant amount of sample per test (including dead volumes) and lengthy analysis times. The long assay times and the large size of these analyzers make them impractical for use in a point-of-sample collection setting.

Also, there is considerable variability in the immunoassay performance, in large part attributed to the techniques being operator dependent, resulting in difficulty comparing results from study to study and even within the same study if more than one laboratory is used. A fully automated and integrated analyzer that eliminates the operator dependence and standardizes results for the immune monitoring assays would considerably improve the interpretation of results from assays.

Though significant advances have been made in the automation of immunoassays, these analyzers are prohibitively expensive and are not affordable in a low-throughput research setting. Lower end systems with automated plate washers, incubators and integrated optics still require a skilled technician to perform several key steps in an immunoassay such as preparing microtiter plates with antibodies and loading samples onto the plates. This results in human error due to repeated manual intervention and is a major source of inter-assay and intra-assay variation.

There is also a need for point of sample collection testing in a variety of fields, such as medicine, environmental, and bioterrorism-related detection fields. As an example, point-of-sample collection (POC) testing for bedside blood analysis has improved but remains a key challenge for modern medical care. Ideally, POC testing would enable the clinicians to diagnose and implement life-saving technologies in real-time by avoiding the need for large laboratory facilities. There remains a need in the art for a lab-on-a-chip that enables simultaneous monitoring of blood gases, metabolites, electrolytes, enzymes, DNA, proteins, and cells, on low sample volumes at the POC.

Microfluidic control of the fluids is an essential requirement for a successful lab-on-a-chip. Microfluidic systems can be broadly grouped into continuous-flow and discrete-flow based architectures. As the name suggests, continuous-flow systems rely on continuous flow of liquids in channels whereas discrete-flow systems utilize droplets of liquid either within channels or in a channel-less architecture. A common limitation of continuous flow systems is that liquid transport is physically confined to permanently fixed channels. The transport mechanisms used are usually pressure-driven by external pumps or electrokinetically-driven by high-voltages. These approaches involve complex channeling and require large supporting systems in the form of external valves or power supplies. These restrictions make it difficult to achieve a high degree of functional integration and control in conventional continuous-flow systems, particularly in realizing a handheld device at the point-of-sample collection. There remains a need in the art for a point of sample collection testing system that makes use of droplet manipulations and especially a system that can accomplish multiple tests or multiple types of tests on a single chip.

5 BRIEF DESCRIPTION OF THE INVENTION

The present invention relates to droplet-based surface modification and washing. According to one embodiment, a method of splitting a droplet is provided, the method comprising providing a droplet microactuator comprising a droplet comprising one or more beads and immobilizing at least one of the one or more beads. The method further comprises conducting one or more droplet operations to divide the droplet to yield a set of droplets comprising a droplet comprising the one or more immobilized beads and a droplet substantially lacking the one or more immobilized beads.

6 DEFINITIONS

As used herein, the following terms have the meanings indicated.

"Activate" with reference to one or more electrodes means effecting a change in the electrical state of the one or more electrodes which results in a droplet operation.

"Affinity" means the specific or non-specific intramolecular attraction of one molecule for another molecule or for a substrate, such as the attraction of an antibody for its corresponding antigen or hapten.

"Analyte," means a target substance for detection which may be present in a sample. Illustrative examples include antigenic substances, haptens, antibodies, proteins, peptides, amino acids, nucleotides, nucleic acids, drugs, ions, salts, small molecules, cells.

"Antibody" means a polypeptide that has affinity for an epitope or hapten. An antibody can be a polyclonal antibody, a monoclonal antibody, an antibody fragment, and/or an engineered molecule capable of binding the corresponding member of a specific binding pair. Antibodies may be labeled or otherwise conjugated to molecules that facilitate direct or indirect detection of and/or quantification of the antibody.

"Bead," with respect to beads on a droplet microactuator, means any bead or particle capable of interacting with a droplet on or in proximity with a droplet microactuator. Beads may be any of a wide variety of shapes, such as spherical, generally spherical, egg shaped, disc shaped, cubical and other three dimensional shapes. The bead may, for example, be capable of being transported in a droplet on a droplet microactuator; configured with respect to a droplet microactuator in a manner which permits a droplet on the droplet microactuator to be brought into contact with the bead, on the droplet microactuator and/or off the droplet microactuator. Beads may be manufactured using a wide variety of materials, including for example, resins, and polymers. The beads may be any suitable size, including for example, microbeads, microparticles, nanobeads and nanoparticles. In some cases, beads are magnetically responsive; in other cases beads are not significantly magnetically responsive. For magnetically responsive beads, the magnetically responsive material may constitute substantially all of a bead or only one component of a bead. The remainder of the bead may include, among other things, polymeric material, coatings, and moieties which permit attachment of an assay reagent. Examples of suitable magnetically responsive beads are described in U.S. Patent Publication No. 2005-0260686, "Multiplex flow assays preferably with magnetic particles as solid phase," published on Nov. 24, 2005, the entire disclosure of which is incorporated herein by reference for its teaching concerning magnetically responsive materials and beads.

"dNTP" means deoxynucleotidetriphosphate, where the nucleotide is any nucleotide, such as A, T, C, G or U. "ddNTP" means dideoxynucleotidetriphosphate, where the nucleotide is any nucleotide, such as A, T, C, G or U. It will be appreciated that unless otherwise specifically indicated, ddNTP can be substituted for dNTP, and vice versa.

"Droplet" means a volume of liquid on a droplet microactuator which is at least partially bounded by filler fluid. For example, a droplet may be completely surrounded by filler fluid or may be bounded by filler fluid and one or more surfaces of the droplet microactuator. Droplets may take a wide variety of shapes; nonlimiting examples include generally disc shaped, slug shaped, truncated sphere, ellipsoid, spherical, partially compressed sphere, hemispherical, ovoid, cylindrical, and various shapes formed during droplet operations, such as merging or splitting or formed as a result of contact of such shapes with one or more surfaces of a droplet microactuator.

"Droplet operation" means any manipulation of a droplet on a droplet microactuator. A droplet operation may, for example, include: loading a droplet into the droplet microactuator; dispensing one or more droplets from a source droplet; splitting, separating or dividing a droplet into two or more droplets; transporting a droplet from one location to another in any direction; merging or combining two or more droplets into a single droplet; diluting a droplet; mixing a droplet; agitating a droplet; deforming a droplet; retaining a droplet in position; incubating a droplet; heating a droplet; vaporizing a droplet; cooling a droplet; disposing of a droplet; transporting a droplet out of a droplet microactuator; other droplet operations described herein; and/or any combination of the foregoing. The terms "merge," "merging," "combine," "combining" and the like are used to describe the creation of one droplet from two or more droplets. It should be understood that when such a term is used in reference to two or more droplets, any combination of droplet operations sufficient to result in the combination of the two or more droplets into one droplet may be used. For example, "merging droplet A with droplet B," can be achieved by transporting droplet A into contact with a stationary droplet B, transporting droplet B into contact with a stationary droplet A, or transporting droplets A and B into contact with each other. The terms "splitting," "separating" and "dividing" are not intended to imply any particular outcome with respect to size of the resulting droplets (i.e., the size of the resulting droplets can be the same or different) or number of resulting droplets (the number of resulting droplets may be 2, 3, 4, 5 or more). The term "mixing" refers to droplet operations which result in more homogenous distribution of one or more components within a droplet. Examples of "loading" droplet operations include microdialysis loading, pressure assisted loading, robotic loading, passive loading, and pipette loading.

"Electronically coupled" is used herein to indicate an electrical or data relationship between two or more components or elements. As such, the fact that a first component is said to be electronically coupled to a second component is not intended to exclude the possibility that additional components may be present between, and/or operatively associated or engaged with, the first and second components. Further, electrically coupled components may in some embodiments include wireless intervening components.

"Highlight" used with reference to a user interface or the like, such as a droplet microactuator map as described herein, means that a component of the user interface or map may be visually differentiated, e.g., by a change in color, brightness, shading, shape, or by appearance/disappearance of a symbol, icon, or other visual identifier. For example, mousing over or selecting a representation of an electrode on the user interface or may cause the electrode representation to change color. Sounds may also accompany highlighted items to further facilitate user interaction with the system.

"Input device" is used broadly to include all possible types of devices and ways to input information into a computer system or onto a network. Examples include stylus-based devices, pen-based devices, keyboard devices, keypad devices, touchpad devices, touch screen devices, joystick devices, trackball devices, mouse devices, bar-code reader devices, magnetic strip reader devices, infrared devices, speech recognition technologies.

"Magnetically responsive" means responsive to a magnetic field. Examples of magnetically responsive materials include paramagnetic materials, ferromagnetic materials, ferrimagnetic materials, and metamagnetic materials. Examples of suitable paramagnetic materials include iron, nickel, and cobalt, as well as metal oxides such as $Fe_3O_4$, $BaFe_{12}O_{19}$, CoO, NiO, $Mn_2O_3$, $Cr_2O_3$, and CoMnP.

"Output device" is used broadly to include all possible types of devices and ways to output information or data from a computer system to a user or to another system. Examples include visual displays, LEDs, printers, speakers, modems and wireless transceivers.

"Protocol" means a series of steps that includes, but is not limited to, droplet operations on one or more droplet microactuators.

"Select" with reference to a user interactive element, such as icon, field, or virtual button, displayed on a user interface means to provide input which results in the execution of instructions associated with the object. Thus, for example, selection of a representation of an electrode displayed on a droplet microactuator map by pointing and clicking on the electrode representation may result in execution of instructions necessary for activating the actual electrode and/or instructions necessary for adding a line of code to a set of instructions which instructs activation of the actual electrode. Selection may be achieved using any of a variety of input devices or combination of input devices, such as mouse, joystick, and/or keyboard.

"Surface" with reference to immobilization of a molecule, such as an antibody or in analyte, on the surface, means any surface on which the molecule can be immobilized while retaining the capability to interact with droplets on a droplet microactuator. For example, the surface may be a surface on the droplet microactuator, such as a surface on the top plate or bottom plate of the droplet microactuator; a surface extending from the top plate or bottom plate of the droplet microactuator; a surface on a physical object positioned on the droplet microactuator in a manner which permits it to interact with droplets on the droplet microactuator; and/or a bead positioned on the droplet microactuator, e.g., in a droplet and/or in a droplet microactuator but exterior to the droplet.

"Washing" with respect to washing a surface means reducing the amount of one or more substances in contact with the surface or exposed to the surface from a droplet in contact with the surface. The reduction in the amount of the substance may be partial, substantially complete, or even complete. The substance may be any of a wide variety of substances; examples include target substances for further analysis, and unwanted substances, such as components of a sample, contaminants, and/or excess reagent. The surface may, for example, be a surface of a droplet microactuator or a surface of a bead on a droplet microactuator. In some embodiments, a washing operation begins with a starting droplet in contact with a surface, where the droplet includes an initial total amount of a substance. The washing operation may proceed using a variety of droplet operations. The washing operation may yield a droplet in contact with the surface, where the droplet has a total amount of the substance which is less than the initial amount of the substance. In another embodiment, the droplet operation may yield the surface in the absence of a droplet, where the total amount of the substance in contact with the surface or otherwise exposed to the surface is less than the initial amount of the substance in contact with the surface or exposed to the surface in the starting droplet. Other embodiments are described elsewhere herein, and still others will be immediately apparent in view of the present disclosure.

When a given component such as a layer, region or substrate is referred to herein as being disposed or formed "on" another component, that given component can be directly on the other component or, alternatively, intervening components (for example, one or more coatings, layers, interlayers, electrodes or contacts) can also be present. It will be further understood that the terms "disposed on" and "formed on" are used interchangeably to describe how a given component is positioned or situated in relation to another component. Hence, the terms "disposed on" and "formed on" are not intended to introduce any limitations relating to particular methods of material transport, deposition, or fabrication.

When a liquid in any form (e.g., a droplet or a continuous body, whether moving or stationary) is described as being "on", "at", or "over" an electrode, array, matrix or surface, such liquid could be either in direct contact with the electrode/array/matrix/surface, or could be in contact with one or more layers or films that are interposed between the liquid and the electrode/array/matrix/surface.

When a droplet is described as being "on" or "loaded on" a droplet microactuator, it should be understood that the droplet is arranged on the droplet microactuator in a manner which facilitates using the droplet microactuator to conduct droplet operations on the droplet, the droplet is arranged on the droplet microactuator in a manner which facilitates sensing of a property of or a signal from the droplet, and/or the droplet has been subjected to a droplet operation on the droplet microactuator.

7 BRIEF DESCRIPTION OF THE DRAWINGS

FIGS. 21A-21D is a side profile view illustrating various droplet microactuator sensor element configurations in accordance with various embodiments of the present invention.

8 DETAILED DESCRIPTION OF THE INVENTION

The invention provides methods, devices and systems for executing one or more droplet-based biochemical assays. For example, the invention provides methods, devices and systems for amplifying nucleic acids, analyzing the sequences of nucleic acids, conducting affinity-based assays, and/or analyzing components of bodily fluids.

In certain embodiments, a protocol of the system may involve one or more of the following steps in any order which achieves the detection end of the invention: extracting sample from a subject; processing the sample for loading onto a droplet microactuator; loading the sample onto the droplet microactuator; dispensing one or more sample droplets of the sample for transport on the droplet microactuator; loading one or more reagents onto the droplet microactuator; dispensing one or more reagent droplets for transport on the droplet microactuator; transporting one or more reagent droplets and/or one or more sample droplets so as to bring the one or more reagent droplets into contact with the one or more sample droplets thereby effecting interaction of the reagent with the sample; detecting an effect of the interaction of the reagent with the sample; providing output notifying the user of the results of the detecting step. Examples of biochemical protocols for use with a droplet microactuator of the invention are discussed in the ensuing sections.

8.1 Nucleic Acid Amplification

The invention provides methods, devices and systems for amplification of nucleic acids in droplets on a droplet microactuator. A large number of copies of one or more nucleic acid molecules can be made in a single droplet from a small number of copies or even a single copy present in the droplet. The methods of the invention generally involve combining the necessary reactants to form an amplification-ready droplet and thermal cycling the droplet at temperatures sufficient to result in amplification of a target nucleic acid, e.g., by the polymerase chain reaction (PCR). In some embodiments, a droplet including the amplified target nucleic acid may then be transported into a subsequent process, such as a detection process, a process for further manipulation of the target nucleic acid, and/or a sequencing process (e.g., as described in Section 8.2). Amplification devices may include a droplet microactuator and components sufficient to conduct droplet operations affecting the methods of the invention when the droplet microactuator is loaded with appropriate reagents. Systems of the invention may include the droplet microactuator plus system components designed to facilitate software control of the operation of the droplet microactuator to execute protocols of the invention.

Figure 1:
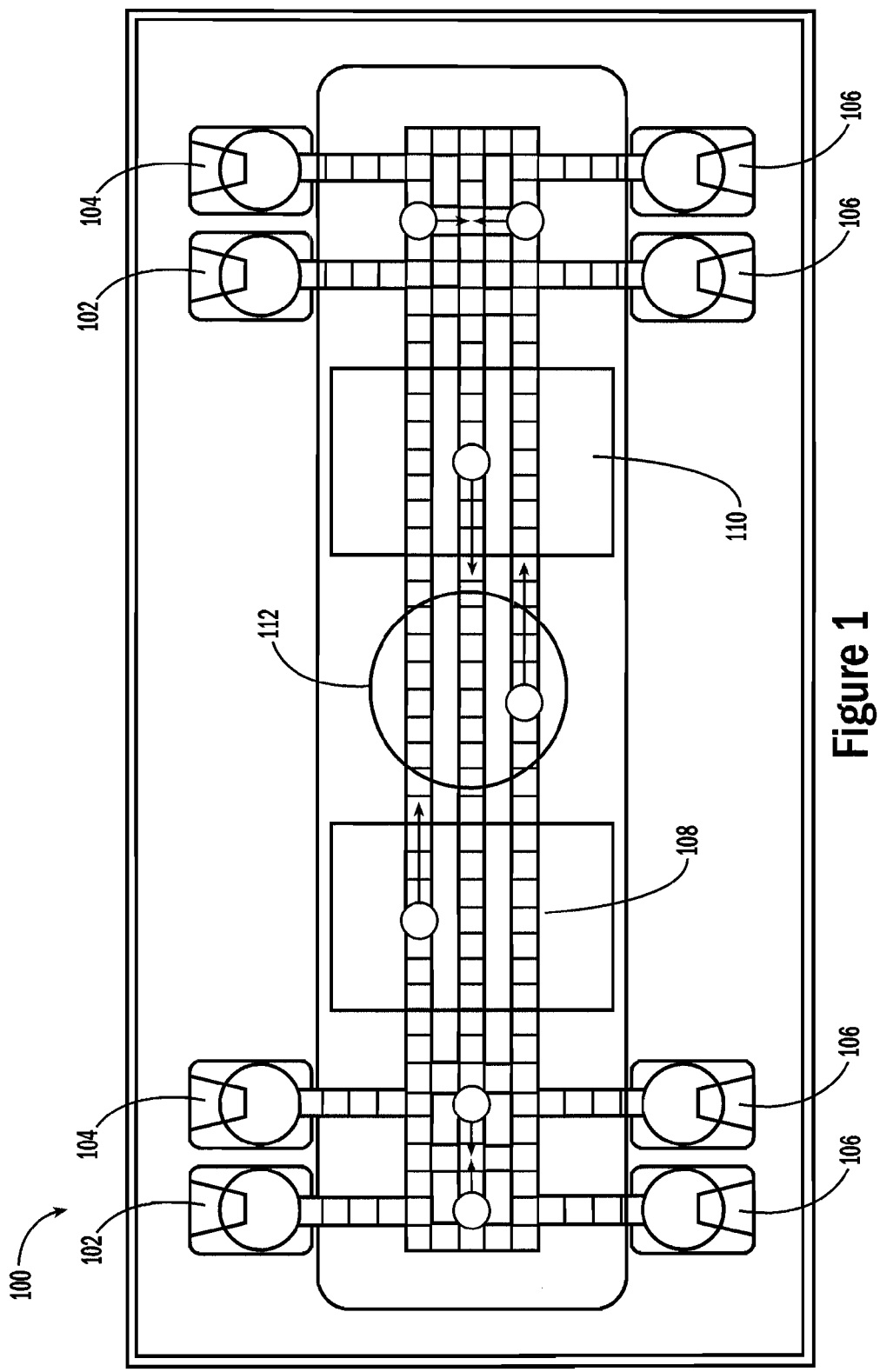
FIG. 1 is a top plan view of a droplet microactuator for use in amplification protocols in accordance with an embodiment of the present invention.

An illustrative droplet microactuator 100 for use in amplification protocols of the invention is illustrated in FIG. 1. In this embodiment, multiple fluid ports and/or reservoirs may be provided, such as sample reservoirs 102, PCR reagent reservoirs 104, and primer set reservoirs 106. Heating areas may also be provided, such as lower temperature heating area 108 and upper temperature heating area 110. A sample visualization area 112 may also be provided, utilizing, for example, a microscope or photomultiplier tube (PMT).

In one embodiment, the invention provides a droplet microactuator and/or system configured and programmed to effect amplification of a sample in a amplification-ready droplet followed by capture of the amplified nucleic acid. The amplified nucleic acid may be treated to denature it into single-stranded nucleic acid before or after it is contacted with magnetically responsive beads to permit the single-stranded nucleic acid to bind to the magnetically responsive beads. Binding, for example, may be accomplished using a biotin-streptavidin system, e.g., in which the single-stranded nucleic acid is biotinylated, and the surface (e.g., beads or droplet microactuator surface) is coated with streptavidin covalently bound thereto. Amplification reagents may be washed away using a washing protocol. Various other methods, devices, systems, and other aspects of the invention will be apparent from the ensuing discussion.

It will be appreciated that an important aspect of the invention involves the ability to conduct droplet operations using each of the nucleic acid amplification reagents and/or samples on a droplet microactuator. For example, the invention includes:

(1) a droplet microactuator comprising thereon a droplet comprising any one or more of the reagents and/or samples described herein for conducting nucleic acid amplification;
(2) a device or system of the invention comprising such droplet microactuator;
(3) a method of conducting droplet operations on or otherwise manipulating a droplet making use of such droplet microactuator or system; and/or
(4) a method of conducting an droplet-based sequence analysis protocol making use of such droplet microactuator or system.

For example, the droplet operations may include one or more of the following: loading a droplet into the droplet microactuator; dispensing one or more droplets from a source droplet; splitting, separating or dividing a droplet into two or more droplets; transporting a droplet from one location to another in any direction; merging or combining two or more droplets into a single droplet; diluting a droplet; mixing a droplet; agitating a droplet; deforming a droplet; retaining a droplet in position; incubating a droplet; heating a droplet; vaporizing a droplet; cooling a droplet; disposing of a droplet; transporting a droplet out of a droplet microactuator; other droplet operations described herein; and/or any combination of the foregoing. Various other methods, devices, systems, and other aspects of the invention will be apparent from the ensuing discussion.

8.1.1 Samples and Sample Preparation

The amplification methods of the invention make use of a sample which includes a nucleic acid template for amplification. The nucleic acid template may be of any type, e.g., genomic DNA, RNA, plasmids, bacteriophages, and/or artificial sequences. The nucleic acid template may be from any source, e.g., whole organisms, organs, tissues, cells, organelles (e.g., chloroplasts, mitochondria), synthetic nucleic acid sources, etc. Further, templates may have a wide variety of origins, e.g., pathological samples, forensic samples, archaeological samples, etc. Biological specimens may, for example, include whole blood, lymphatic fluid, serum, plasma, sweat, tear, saliva, sputum, cerebrospinal (CSF) fluids, amniotic fluid, seminal fluid, vaginal excretions, serous fluid, synovial fluid, pericardial fluid, peritoneal fluid, pleural fluid, transudates, exudates, cystic fluid, bile, urine, gastric fluids, intestinal fluids, fecal samples, and swabs or washes (e.g., oral, nasopharangeal, optic, rectal, intestinal, vaginal, epidermal, etc.) and/or other biological specimens.

Various sample processing steps may be accomplished to prepare the nucleic acid template. In some cases, such as amplification from plasmids or bacteriophages, crude sample will suffice. In other cases, such as amplification of large fragments from genomic DNA, highly purified template is preferred. Sample preparation steps may take place on or off the droplet microactuator.

The system of the invention may be configured and programmed to permit processing of a biological sample to prepare a droplet including a nucleic acid template for amplification. Some portion or all of this processing may be effected on or off the droplet microactuator, e.g., using beads having reagents bound thereto with affinity for target organisms to isolate the target organisms from a biological sample. The droplet microactuator may process the sample by dividing it into one or more discrete droplets for subsequent operations on the droplet microactuator.

Specimens may, in some instances, be treated to change reduce viscosity during subsequent droplet operations. For example, samples can be prepared on the droplet microactuator or off the droplet microactuator by mixing with an alkaline solution (for example, 10% KOH) or reducing agents such as dithiothreitol (DTT) or dithioerythritol (DTE) to liquefy the sample and render it sufficiently fluid to facilitate droplet operations on a droplet microactuator. Other examples of suitable sample preparation techniques are described in U.S. Patent Application No. 60/745,950, entitled "Apparatus and Methods of Sample Preparation for a Droplet Microactuator," filed on Apr. 28, 2006.

A droplet including the nucleic acid template may be combined with amplification reagents to provide an amplification-ready droplet, e.g., combined with PCR reagents to yield a PCR-ready droplet. Depending on the reagents selected, the amplification-ready droplet may be isothermally amplified or thermal cycled to effect amplification of a target nucleic acid. Amplified product may be detected and/or quantified in real-time on a droplet microactuator. In this manner, the invention provides on-chip, real-time, quantitative amplification to detect and quantify a target nucleic acid in a sample.

As nearly 100% of the sample can be utilized for analysis (there is no requirement for priming of channels or pumps), very small sample volumes (e.g., less than about 100 μL or less than about 50 μL or less than about 25 μL) can be analyzed. Many tests can be performed using a single, small sample, and reagent costs can be minimized.

8.1.2 Reagents

In the amplification protocols of the invention, various reagents may be combined with a nucleic acid template to yield an amplification-ready droplet, such as a PCR-ready droplet. PCR reagents typically include primers, nucleotides, polymerase, and buffers. These input reagents may be provided as individual reagents loaded separately onto the droplet microactuator and combined using droplet operations on the droplet microactuator. Moreover, some or all of the reagents may be provided as reagent mixes that are loaded onto the droplet microactuator in a premixed form. In one embodiment, all amplification reagents are combined into a single droplet that must only be combined with a sample droplet in order to yield an amplification-ready droplet, e.g., a PCR-ready droplet.

8.1.2.1 Buffer

Reagents will typically include a buffer. The buffer is selected to facilitate the amplification reaction. Any buffer which fulfills this function is suitable. Magnesium ions are usefully included in the buffer where the nucleic acid being amplified is a DNA.

In one embodiment, the buffer includes KCl, Tris and $MgCl_2$. Other suitable buffers are described in Chamberlain et al., *Nucleic Acid Research* 16:11141-11156 (1988). For example, the buffer may comprise about 500 mM KCl, about 100 mM Tris-HCl (pH 8.3), and about 15 mM $MgCl_2$. In another example, the buffer may comprise about 83 mM $(NH_4)_2SO_4$, about 335 mM Tris-HCl (pH8.8), about 33.5 mM $MgCl_2$, about 50 mM β-Mercapthoethanol, and about 34 mM EDTA. The buffer may also include primers and/or polymerases.

In one embodiment, PCR may be performed sequentially or in parallel in several droplets in which the concentration of one or more buffer components is systematically varied (e.g., in a series of droplets) in order to improve or optimize the buffer for a specific reaction. Thus, for example, any one or more of the following buffer components may be varied: KCl; Tris; $MgCl_2$; $(NH_4)_2SO_4$; β-Mercaptoethanol; EDTA. Once the best of the tested buffer conditions is identified, PCR can proceed using the best buffer system or further optimization may be conducted around the best of the tested buffer systems.

The invention includes a droplet microactuator including a droplet thereon which is a buffer or which comprises a buffer component, as well as systems and/or devices including such a droplet microactuator, and methods of conducting droplet operations on or otherwise manipulating such droplet on a droplet microactuator. Thus, for example, the invention includes a droplet microactuator comprising a droplet thereon, which droplet comprises one or more of the following components: KCl, Tris, $MgCl_2$; $(NH_4)_2SO_4$; β-Mercapthoethanol; EDTA.

Further, the invention includes a droplet microactuator comprising a droplet thereon, which droplet comprises one or more of the foregoing components at a concentration sufficient to facilitate amplification of a target nucleic acid. Moreover, the invention includes such a droplet along with a polymerase, nucleotides and/or one or more primers at a concentration sufficient to facilitate amplification of a target nucleic acid. The invention also includes a method of conducting droplet operations on or otherwise manipulating any of the droplets described in this section using the droplet microactuator, device, and/or system. For example, the droplet operation may include one of more the following: loading a droplet into the droplet microactuator; dispensing one or more droplets from a source droplet; splitting, separating or dividing a droplet into two or more droplets; transporting a droplet from one location to another in any direction; merging or combining two or more droplets into a single droplet; diluting a droplet; mixing a droplet; agitating a droplet; deforming a droplet; retaining a droplet in position; incubating a droplet; heating a droplet; vaporizing a droplet; cooling a droplet; disposing of a droplet; transporting a droplet out of a droplet microactuator; other droplet operations described herein; and/or any combination of the foregoing.

8.1.2.2 Primers

Reagents used in the amplification methods of the invention will include one or more primers. In typical methods, two primers are used to define the region of the nucleic acid template that will be amplified. Primers will typically have a sequence and a length which is selected to ensure efficient replication with few mistakes. Such primers are often in the range of about 18-24 bases long. Other requirements for selection of effective primers are known. Examples of suitable primer properties include lack of internal secondary structure, 40-60% G/C content, balanced distribution of G/C and A/T rich domains, and lack of complementary at the 3' ends to avoid formation of primer dimers. Though not specifically required, primers with one or more of these properties may be suitably employed in the practice of the invention. Additionally, the melting temperature (Tm) for primers is typically selected to permit annealing temperatures of about 55 to about 65° C., or about 62 to about 65° C. A variety of publicly available computer programs exist to help identify primers with properties suitable for use in amplification settings. Where two primers are used, they are typically provided in equal concentrations. Primers may not be necessary in cases in which the nucleic acid being amplified is an RNA.

In some embodiments, degenerate mixtures of primers are used. For example, since a given amino acid sequence may be encoded by several possible codons, the mixture may include all possible sequences covering all codon combinations for a target polypeptide. The degenerate primer mixture may be simplified by identifying codon bias for the organism in question, and including only primers commonly used by the organism.

Primers are provided at any concentration which facilitates amplification of the target nucleic acid. Concentrations should be low enough to avoid an undue amount of mispriming, accumulation of non-specific product, and/or primer-dimer formation. Primer concentration should be high enough to avoid exhaustion of primer prior to completion of the amplification reaction. In some embodiments, concentrations range from about 0.1 μM to about 1 μM or from about 0.1 μM to about 0.6 μM.

Primers may also be labeled. For example, labels may be selected to facilitate detection, localization, quantification, and/or isolation of PCR product. For example, biotinylation can be used to facilitate detection and/or purification using streptavidin to capture biotinylated PCR product on surface. Further, streptavidin can be associated with magnetically responsive beads for capture of biotinylated PCR product. Digoxigenin can also be used for detection of PCR product. Primers may, for example, be labeled at their 5' ends and/or internally, and further, labeled nucleotides may be incorporated into the PCR product for detection, localization, quantification, and/or isolation.

The invention includes a droplet microactuator including a droplet thereon which includes labeled and/or unlabeled primers (e.g., at concentrations ranging from about 0.1 μM to about 1 μM or from about 0.1 μM to about 0.6 μM) for amplification of a target nucleic acid in a concentration sufficient to facilitate the amplification reaction, as well as systems and/or devices including such a droplet microactuator, and methods of conducting droplet operations or otherwise manipulating such droplet on a droplet microactuator. As another example, the invention includes a droplet microactuator including a droplet thereon including labeled and/or unlabeled primers at a low enough concentration to reduce or eliminate mispriming and accumulation of non-specific product and a high enough concentration to avoid exhaustion of primer prior to completion of the amplification reaction. In yet another example, the invention includes a droplet microactuator comprising a droplet thereon including labeled and/or unlabeled primers at a concentration ranging from about 0.1 μM to about 1 μM or from about 0.1 μM to about 0.6 μM. Further, the invention includes such a droplet along with a polymerase, nucleotides and/or buffer components at concentrations selected to facilitate amplification of a target nucleic acid. Moreover, the invention includes a method of conducting droplet operations on or otherwise manipulating any of the droplets described in this section using the droplet microactuator, device, and/or system. For example, the droplet operation may include one of more the following: loading a droplet into the droplet microactuator; dispensing one or more droplets from a source droplet; splitting, separating or dividing a droplet into two or more droplets; transporting a droplet from one location to another in any direction; merging or combining two or more droplets into a single droplet; diluting a droplet; mixing a droplet; agitating a droplet; deforming a droplet; retaining a droplet in position; incubating a droplet; heating a droplet; vaporizing a droplet; cooling a droplet; disposing of a droplet; transporting a droplet out of a droplet microactuator; other droplet operations described herein; and/or any combination of the foregoing.

8.1.2.3 Nucleotides

Reagents used in the amplification methods of the invention will include nucleotides. Stock solutions of dNTPs are commercially available from a variety of sources. Stock solutions are typically provided at concentrations of 100-300 mM. Stock solutions can be diluted prior to introduction to the droplet microactuator and/or on the droplet microactuator using droplet operations to combine the stock solutions with one or more buffer solutions. Final concentrations in the PCR-ready droplet will typically range from about 50 μmol to about 200 μmol. The four dNTPs are typically provided in equimolar concentrations.

A variety of modified nucleotides may be employed in the practice of the invention. Examples include nucleotides designed to reduce secondary structure resolution, prevent contamination, as well as radiolabeled nucleotides, non-radioactive labeled nucleotides, and nucleotides designed to promote random mutagenesis. For examples, see McPherson et al., PCR, Taylor and Francis Group, 2006 (the entire disclosure which is incorporated herein by reference).

The invention includes a droplet microactuator including a droplet thereon which includes nucleotides for amplification of a target nucleic acid in a concentration sufficient to facilitate the amplification reaction, as well as systems and/or devices including such a droplet microactuator, and methods of conducting droplet operations on or otherwise manipulating such a droplet on a droplet microactuator. Thus, for example, the invention includes a droplet microactuator comprising a droplet thereon including one or more nucleotides in a concentration ranging from about 100 mM to about 300 mM (stock concentration) or from about 50 μmol to about 200 μmol (operating concentration). In another example, the invention includes a droplet microactuator comprising a droplet thereon including 1, 2, 3 or 4 nucleotides, each in a concentration ranging from about 100 mM to about 300 mM or from about 50 μM to about 200 μM. The system of the invention may be configured and programmed to execute a protocol for diluting stock nucleotide concentrations to provide droplets comprising operating nucleotide concentrations. For example, the system of the invention may be configured and programmed to execute a protocol diluting stock nucleotide concentrations ranging from about 100 mM to about 300 mM to provide operating solutions ranging from about 50 μmol to about 200 μmol. Further, the invention includes nucleotide-containing droplets along with polymerase(s), primer(s) and/or buffer components in concentrations selected to provide conditions that facilitate amplification of a target nucleic acid. Moreover, the invention includes a method of conducting droplet operations on or otherwise manipulating any of the droplets described in this section using the droplet microactuator, device, and/or system. For example, the droplet operation may include one of more the following: loading a droplet into the droplet microactuator; dispensing one or more droplets from a source droplet; splitting, separating or dividing a droplet into two or more droplets; transporting a droplet from one location to another in any direction; merging or combining two or more droplets into a single droplet; diluting a droplet; mixing a droplet; agitating a droplet; deforming a droplet; retaining a droplet in position; incubating a droplet; heating a droplet; vaporizing a droplet; cooling a droplet; disposing of a droplet; transporting a droplet out of a droplet microactuator; other droplet operations described herein; and/or any combination of the foregoing.

8.1.2.4 PCR Polymerases

A variety of PCR polymerases may be used in the droplet-based PCR protocols of the invention. Suitable polymerases will often have optimal activity at about 75° C. and the ability to retain that activity after prolonged incubation, e.g., at temperatures greater than 95° C. Useful polymerases may, for example, include DNA-dependent DNA polymerases and/or RNA-dependent DNA polymerases (reverse transcriptases). Various thermostable polymerases, such as Taq DNA polymerases, may be used. Suitable examples include Ampli-Taq®, AmpliTaq Gold®, the Stoffel fragment of AmpliTaq®, and others. Examples of thermostable polymerases with proofreading capability include Vent®, Tli, DeepVent®, Pfu, Pwo, UlTma®, Accuzyme®, and KOD Hifi, DNA polymerases, as well as various exo⁻versions of the foregoing. Polymerase preparations may in some cases include dyes for determining or confirming concentrations of PCR reagents. In some cases, the system is configured and programmed to detect such dyes and calculate reagent concentrations based on colorimetric measurements. In some cases, the invention makes use of droplets including a combination of a thermostable polymerase (e.g., Taq DNA Polymerase) and a proofreading polymerase (e.g., Pwo DNA Polymerase).

The invention includes a droplet microactuator including a droplet thereon which includes one or more polymerases at concentrations sufficient to facilitate the amplification reaction, as well as systems and/or devices including such a droplet microactuator, and methods of conducting droplet operations or otherwise manipulating such droplet on a droplet microactuator. Moreover, the invention includes a method of conducting droplet operations on or otherwise manipulating any of the droplets described in this section using the droplet microactuator, device, and/or system. For example, the droplet operation may include one of more the following: loading a droplet into the droplet microactuator; dispensing one or more droplets from a source droplet; splitting, separating or dividing a droplet into two or more droplets; transporting a droplet from one location to another in any direction; merging or combining two or more droplets into a single droplet; diluting a droplet; mixing a droplet; agitating a droplet; deforming a droplet; retaining a droplet in position; incubating a droplet; heating a droplet; vaporizing a droplet; cooling a droplet; disposing of a droplet; transporting a droplet out of a droplet microactuator; other droplet operations described herein; and/or any combination of the foregoing. Further, the invention includes polymerase-containing droplets on a droplet microactuator of the invention along with nucleotides, primer and/or buffer in concentrations selected to provide conditions sufficient to facilitate amplification of a target nucleic acid.

8.1.2.5 Detection of Amplified Product

In some embodiments, amplified nucleic acid will be detected after some number of amplification cycles. For example, amplified nucleic acid may be quantified during or after each cycle, or after some predetermined number of cycles, e.g., after each set of 2, 3, 4, 5, 6, 7, 8, 9, or 10 cycles. Detection generally involves using droplet operations to transport the droplet into detection zone in which a sensor measures some aspect of the droplet, such as a physical, chemical or electrical aspect, which correlates with amplification. The system may be programmed so that amplification cycles may be continued until detection reveals that a desired level of signal has been achieved. In one embodiment, the detection method for amplification is a fluorescence technique.

Further, in some embodiments, a droplet comprising amplified nucleic acid may be transported for further processing/detection. For example, in diagnostic embodiments, a droplet including amplified nucleic acid may be transported for detection of the presence of a target diagnostic nucleic acid. The target nucleic acid may, for example, include a nucleic acid from the pathogenic organism, such as a DNA or RNA associated with a parasite, bacteria, fungus or virus. The droplet microactuator may be provided as a component of an integrated and portable diagnostic platform. The system may provide for fully automated, rapid detection of a panel of infectious diseases by real-time PCR. The system may be used at the bedside, stat laboratory, physician's office, or in the field.

Fluorescence detection is suitable for detection of amplified nucleic acid. Light emitting diodes (LEDS) and laser diodes are suitable as excitation sources because of their small physical size, low power requirements and long life. LEDs are appealing because of their low cost and laser diodes because of their narrow spectral width, and the fact that they can be focused to small spot sizes without discarding a substantial amount of light.

In addition to the reagents already discussed, reagents usefully employed in nucleic acid amplification protocols of the invention include various detection reagents, such as fluorescent and non-fluorescent dyes and probes. For example, the protocols may employ reagents suitable for use in a TaqMan reaction, such as a TaqMan probe; reagents suitable for use in a SYBR® Green reaction, such as SYBR® Green; reagents suitable for use in a molecular beacon reaction, such as a molecular beacon probe; reagents suitable for use in a scorpion reaction, such as a scorpion probe; reagents suitable for use in a fluorescent DNA-binding dye-type reaction, such as a fluorescent probe; and/or reagents for use in a LightUp protocol, such as a LightUp probe.

The invention includes a droplet microactuator including a droplet thereon which includes one or more detection reagents, such as any one or more of the aforementioned probes, at concentrations sufficient to facilitate detection of the amplification reaction, as well as systems and/or devices including such a droplet microactuator, and methods of conducting droplet operations or otherwise manipulating such droplet on a droplet microactuator. Moreover, the invention includes a method of conducting droplet operations on or otherwise manipulating any of the droplets described in this section using the droplet microactuator, device, and/or system. For example, the droplet operation may include one of more the following: loading a droplet into the droplet microactuator; dispensing one or more droplets from a source droplet; splitting, separating or dividing a droplet into two or more droplets; transporting a droplet from one location to another in any direction; merging or combining two or more droplets into a single droplet; diluting a droplet; mixing a droplet; agitating a droplet; deforming a droplet; retaining a droplet in position; incubating a droplet; heating a droplet; vaporizing a droplet; cooling a droplet; disposing of a droplet; transporting a droplet out of a droplet microactuator; other droplet operations described herein; and/or any combination of the foregoing. Further, the invention includes nucleotide-containing droplets on a droplet microactuator of the invention along with a nucleotides, primer, detection probe and/or buffer in concentrations selected to provide conditions sufficient to facilitate amplification of a target nucleic acid.

Furthermore, the invention includes methods of detecting and/or quantifying amplification which methods include measuring a signal (e.g., a fluorescent signal) from droplet on a droplet microactuator. Thus, for example, the method may employ exposure of a droplet potentially including a fluorescent dye (such as SYBR® Green) to a light source at a wavelength selected to cause the compound to fluoresce and measuring the resulting fluorescence. Fluorescence emitted from the droplet can be tracked during an amplification reaction to permit monitoring of the reaction, e.g., using a SYBR® Green-type compound. A system of the invention may, for example, be programmed to detect such fluorescence and to display a corresponding graph or other output permitting a user to track the progress of a PCR reaction in real-time.

In another example, the invention includes a method of detecting and/or quantifying the presence of a target nucleic acid by including a probe with specificity for a target nucleic acid (e.g., a TaqMan-type probe) in an amplification-ready droplet potentially including the target nucleic acid, thermal cycling the amplification-ready droplet, and detecting any fluorescence signal caused by degradation of the probe, where a fluorescent signal is indicative of the presence of the target nucleic acid in the droplet. The invention includes corresponding methods using other target-specific probes, such as scorpion probes and molecular beacons.

8.1.3 Thermal Cycling

In the practice of the invention, a PCR-ready droplet is thermal cycled in order to effect an amplification of a target nucleic acid. Tight control of thermal cycling may be necessary for effective amplification of certain nucleic acids. Examples of structures designed to provide controlled thermal cycling on a droplet microactuator are discussed in Section 8.8.6 below. Typically, each thermal cycle will involve at least two steps:

(1) heating the droplet to a temperature sufficient to denature double stranded nucleic acid in the droplet into single-stranded DNA (typically about 90-100° C.); and
(2) lowering the droplet temperature to permit primers to anneal to their complementary sequences on the nucleic acid template strands (typically about 50-75° C.).

In some cases a thermal cycle may also involve a third step:

(3) adjusting the droplet temperature to facilitate extension of the double stranded segment of the nucleic acid to be extended by incorporation of additional nucleotides (typically about 70-75° C.).

Depending on the reagents selected, incorporation of additional nucleotides may be accomplished at the same temperature at which the primers are permitted to anneal to the nucleic acid template strands, and thus the temperature adjustment of the third step may not be necessary. Additional thermal cycling steps may also be incorporated in various protocols of the invention.

The invention permits multiple droplets to be thermal cycled in parallel. Thus, in various embodiments, more than 2, 3, 4, 5, 10, 20, 30, 40, 50, 100, or 1000 amplification-ready droplets are thermal cycled in parallel on a single droplet microactuator. In some embodiments, detection of amplification in these droplets is measured in parallel in real time.

In one embodiment, each droplet undergoing thermal cycling is positioned in proximity to a sensor, or is transported into proximity with a sensor, so that a signal from the droplet correlating with amplification can be monitored in real time. The system may output real-time information accessible to a user which is indicative of the progress of the amplification process. Further, the system may be arranged to permit such output when thermal cycling multiple droplets in parallel, e.g., more than 2, 3, 4, 5, 10, 20, 30, 40, 50, 100, or 1000 amplification-ready droplets are thermal cycled in parallel on a single droplet microactuator and the system outputs real-time information is indicative of the progress of the amplification process The methods of the invention may include a temperature optimization step or protocol for optimizing temperatures and/or times for denaturation, annealing, and/or extension. In this step, one or more heating zones is used to vary the temperature of one of more heating steps. For example, the methods may include an optimization step or protocol for optimization of annealing temperature. A series of droplets may be thermal cycled using varied annealing temperatures followed by detection to quantify amplification and thereby determine which of the tested annealing temperatures produces the best results. Subsequent thermal cycling can be conducted at the selected temperature. Similarly a series of droplets may be cycled through annealing temperatures for different periods of time followed by detection to quantify amplification and thereby determine which of the tested time periods produces the best results at a given temperature. Subsequent thermal cycling can be conducted using the selected time period. Further, such optimization protocols can be executed sequentially or simultaneously in order to determine both the optimum temperature and the optimum time period. Similar protocols may be executed for optimizing temperatures and/or time periods for denaturation and/or extension steps.

In one embodiment, thermal cycling is accomplished by heating and cooling the entire droplet microactuator. This embodiment generally involves the following steps:

(1) heating the droplet microactuator to a temperature sufficient to denature the double-stranded DNA (present in a droplet on the droplet microactuator) into single-stranded DNA;
(2) lowering the temperature of the droplet microactuator to a temperature sufficient to permit primers (present in a droplet on the droplet microactuator) to anneal to their complementary sequences on the nucleic acid template strands;
(3) optionally, adjusting the temperature of the droplet microactuator to facilitate extension of the double stranded segment of the nucleic acid (present in a droplet on the droplet microactuator) by incorporation of additional nucleotides.

The thermal cycling protocols of the invention may be conducted without significant loss of water or other components of the PCR-ready droplet. Further, the thermal cycling protocols may be conducted without significant cross-contamination between droplets. Moreover, the thermal cycling may be conducted without significant disruption in the capability of the droplet microactuator to continue conducting droplet operations. For example, droplet operations may in some cases continue to be conducted at the various denaturation, annealing, and/or extension temperatures.

In a related embodiment, thermal cycling is accomplished by heating and cooling a section or region of the droplet microactuator. This approach generally involves the following steps:

(1) heating a section or region of the droplet microactuator to a temperature sufficient to denature the double-stranded DNA (present in a droplet on the droplet microactuator) into single-stranded DNA;
(2) lowering the temperature of a section or region of the droplet microactuator to a temperature sufficient to permit primers (present in a droplet on the droplet microactuator) to anneal to their complementary sequences on the nucleic acid template strands;
(3) optionally, adjusting the temperature of a section or region of the droplet microactuator to facilitate extension of the double stranded segment of the nucleic acid (present in a droplet on the droplet microactuator) by incorporation of additional nucleotides.

Figure 2B:
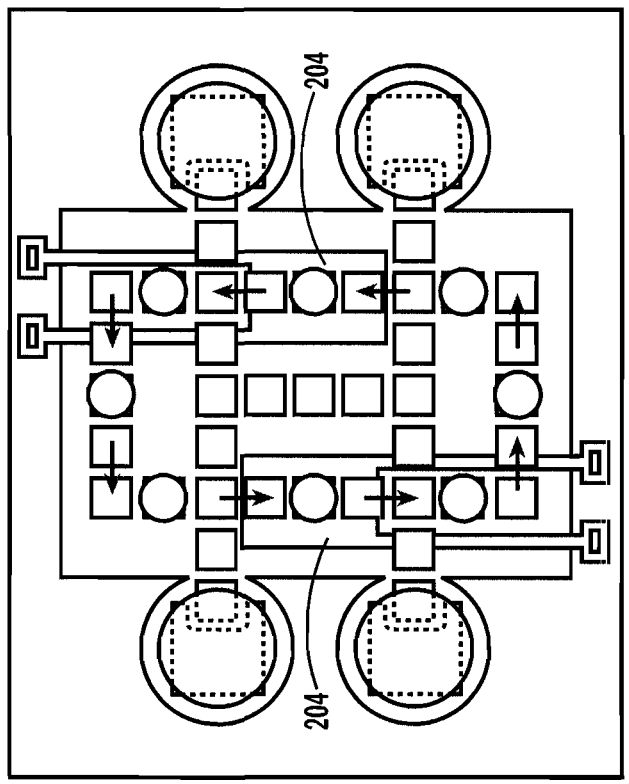
FIGS. 2A and 2B are top plan views of a droplet microactuator with a single integrated heater and a plurality of integrated heaters, respectively, in accordance with various embodiments of the present invention.
Figure 2A:
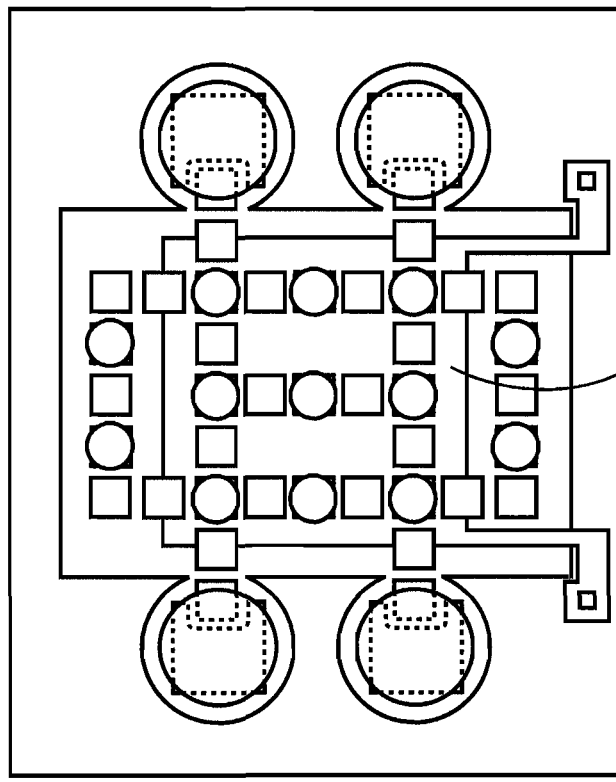

In one embodiment, this approach is conducted using a droplet microactuator with a single integrated heater 202, as illustrated in FIG. 2A.

In another embodiment, regions of the droplet microactuator may be maintained at the required temperatures, and the droplets may be transported through the appropriate temperature regions in order to accomplish the thermal cycling. This approach generally involves the following steps:

(1) transporting an amplification-ready droplet to a region of the droplet microactuator that is maintained at a temperature appropriate to cause denaturation of double-stranded DNA in the droplet into single-stranded DNA;
(2) transporting the amplification-ready droplet to a region of the droplet microactuator that is maintained at a temperature sufficient to permit primers in the droplet to anneal to their complementary sequences on the nucleic acid template strands; and
(3) optionally, transporting an amplification-ready droplet to a region of the droplet microactuator that is maintained at a temperature sufficient to facilitate or optimize extension of the double-stranded segment of the nucleic acid in the droplet by incorporation of additional nucleotides.

In this embodiment, thermal cycling is accomplished by repeating the transporting steps to move the droplets from zone to zone. In one embodiment, the droplet microactuator includes only one thermal zone for each required temperature, and thermal cycling is accomplished by rotating each droplet through the appropriate thermal zones. In another embodiment, the droplet microactuator includes two or more of each of the thermal zones. In yet another embodiment, the droplet microactuator includes two or more of one or more of the thermal zones. Further, the droplet microactuator may include 2, 3 or more thermal zones, each of which may be heated to a different specified temperature. In one embodiment, this approach is conducted using a droplet microactuator with a plurality of integrated heaters 204, as illustrated in FIG. 2B.

Further, one or more heaters may be used to establish a continuous thermal gradient across a region of the droplet microactuator. In this embodiment, an electrode matrix, electrode path or series of electrode paths may be employed to locate the droplet in the appropriate temperature zone to effect the required thermal cycling steps. Thermal cycling may thus be accomplished by transporting the droplet to an electrode at the appropriate position within the thermal gradient to achieve the target temperature. Variations in temperature, e.g., to optimize any of the various denaturing, annealing and/or extension steps, may be effected by simply varying the location of the droplet within the thermal zone.

Thermal cycling may involve the use of various heating and/or cooling modalities to establish target temperature zones for denaturation, annealing and/or extension. These heating and cooling modalities may be arranged to facilitate a suitable temperature ramp between the target temperature zones. The ramp may be controlled by changing the temperature of a specific heating and/or cooling modality and/or by selecting heating and cooling modalities at distances selected to effect target temperature zones with suitable temperature ramps. The droplet microactuator may have heating and/or cooling modalities with temperature ranges and spacing selected to create a predetermined set of potential target temperature zones and temperature ramps. Various heating and/or cooling modalities may be included between target temperature zones to adjust the ramp between zones.

In one embodiment, the droplet microactuator includes a series of independently adjustable heating elements. The temperature of each heating element may be adjusted to provide for an appropriate heating ramp as droplets pass from one target temperature zone to the next. Further, distance between heating elements at target temperatures may be selected to facilitate an appropriate temperature ramp and/or to prevent overheating caused by interaction between closely situated heating elements. Such approaches provide flexibility in working with a variety of protocols each requiring different target temperature zones and ramp profiles. For example, in a series or matrix of heating elements, target temperature zones may be at adjacent heating elements and/or may be separated by one or more heating elements such that they are separated by a greater distance. In this way, distances may be varied to account for temperature requirements of a variety of protocol requirements. A system of the invention may select optimal heating elements for establishing target temperature zones with appropriate or optimal temperature ramps between the heating zones.

The methods of the invention may include a temperature optimization step or protocol for optimizing temperatures and/or times for the denaturation, annealing, and/or extension phases of the thermal cycle. As an example, the methods may include an optimization step or protocol for optimization of annealing temperature. A series of heating zones may be established in which amplification-ready droplets are cycled through different annealing temperatures to determine which annealing temperature produces optimum results. Subsequent thermal cycling can be conducted at the optimum temperature. Similarly a series of amplification-ready droplets may be cycled using a protocol in which the time of the annealing phase is systematically varied to determine which time period produces optimum results at a given temperature. Subsequent thermal cycling can be conducted using the optimum time period. Further, such protocols can be executed sequentially or simultaneously in order to determine both the optimum temperature and the optimum time period. Similar protocols may be executed for optimizing denaturation and/or extension steps. Optimization protocols my run sequentially or in parallel.

Similarly, the methods of the invention may include a temperature optimization step or protocol using multiple independently heated thermal zones for optimizing temperatures and/or times for denaturation, annealing, and/or extension. For example, a series of heating zones may be established through which amplification-ready droplets are transported. The zones may include temperatures targeted to promote denaturation, annealing, and/or extension. In a specific droplet set, the temperature of one of the denaturation, annealing and/or extension zones may be systematically varied for a set of PCR-ready droplets, while the other two temperatures remain constant. Multiple droplet sets can be tested so that each of the temperature parameters may be varied as needed. One or more of the multiple droplet sets may be tested sequentially and/or in parallel. Variations in heating zone temperature may, for example, be controlled by the processor (e.g., controlling the temperature of a heating element and/or controlling a location of a droplet within a heating gradient) via software pre-programmed to execute an optimization protocol and/or via software controlled by a user via a user interface. The timing of each of the phases of the thermal cycle may be optimized in like manner. Optimization protocols my run sequentially or in parallel.

Moreover, the invention includes a method of conducting one or more droplet operations using a PCR-ready droplet on a droplet microactuator at an elevated temperature, e.g., at a temperature which is greater than about 70, 75, 80, 85, 90, 95, or 100° C. For example, the droplet operation may include: loading a droplet into the droplet microactuator; dispensing one or more droplets from a source droplet; splitting, separating or dividing a droplet into two or more droplets; transporting a droplet from one location to another in any direction; merging or combining two or more droplets into a single droplet; diluting a droplet; mixing a droplet; agitating a droplet; deforming a droplet; retaining a droplet in position; incubating a droplet; heating a droplet; vaporizing a droplet; cooling a droplet; disposing of a droplet; transporting a droplet out of a droplet microactuator; other droplet operations described herein; and/or any combination of the foregoing. Still further, the invention includes a method of heating and/or cooling a droplet by transporting the droplet between two or more temperature zones on a droplet microactuator. Further, the invention includes a method of heating and/or cooling a droplet by transporting the droplet between two or more temperature zones on a droplet microactuator when the temperature zones range from about 40° C. to about 120° C. The invention also includes a method of heating and/or cooling a droplet by transporting the droplet between two or more temperature zones on a droplet microactuator when the temperature zones range from about 40° C. to about 120° C. to achieve target temperatures at least some of which are at a temperature which is greater than about 70, 75, 80, 85, 90, 95, or 100° C.

The invention includes a droplet microactuator or droplet microactuator system having one or more input reservoirs loaded with reagents for conducting biochemical reactions, such as the reagents described for use in nucleic acid amplification protocols, affinity-based assay protocols, sequencing protocols, and protocols for analyses of biological fluids. For example, one or more reservoirs may include reagents for providing buffer, primers, nucleotides, polymerases, and other reagents for conducting a PCR reaction. In one embodiment, one or more reservoirs includes a buffer which includes two or more reagents for conducting a PCR reaction, where in the reagents are selected from primers, nucleotides, polymerases, and other PCR reagents. In another embodiment, one or more of the reservoirs includes a droplet including all reagents required for conducting a PCR reaction, such that when combined with a sample droplet including a nucleic acid template, the result is a droplet which is ready for PCR thermal cycling. The invention also includes a droplet microactuator or droplet microactuator system, having one or more input reservoirs loaded with a sample for conducting a PCR reaction.

8.1.4 Amplification Protocols

It will be appreciated by one of skill in the art in light of the present disclosure that many variations are possible within the scope of the invention. In general, the protocols involve combining two or more droplets comprising PCR reagents and template to yield a PCR-ready droplet, and thermal cycling the PCR-ready droplet at temperatures selected to facilitate amplification of a target nucleic acid.

Upstream, the protocol may involve various sample-processing steps in order to provide a nucleic acid template that is ready for PCR amplification. For example, reverse transcription of RNA may be used prior to PCR to provide a stable DNA nucleic acid template for amplification. Thus, in one embodiment, the invention provides a method of preparing a droplet comprising a DNA nucleic acid template, wherein the method includes performing droplet-based reverse transcription of RNA to yield the nucleic acid template.

A "Hot Start" approach can be used to minimize the formation of primer-dimers during reaction preparation. By limiting polymerase activity prior to PCR cycling, non-specific amplification is reduced and target yield is increased. Common methods for Hot Start PCR include chemical modifications, wax-barrier methods, and inhibition by a Taq-directed antibody.

Downstream, the protocol may involve various subsequent steps, such as sequencing of an amplified nucleic acid, e.g., using a pyrosequencing approach or separation of amplified fragments using capillary electrophoresis, Various specialized techniques may also be used during the PCR process. For example, primers with sequences not completely complementary to the nucleic acid template can be used for droplet-based in vitro mutagenesis. Thus, for example, the invention may include a method of accomplishing in vitro mutagenesis in a droplet on a droplet microactuator, when the method involves combining two or more droplets including PCR reagents and primers selected for mutagenesis in quantities sufficient to facilitate amplification of a mutated version of the target nucleic acid. Further, the mutated version of the target nucleic acid may be transported for downstream processing, e.g., sequencing of the mutated version of the target nucleic acid to confirm the desired mutation.

In a medical diagnostic aspect of the invention, molecular tags, such as digoxigenin (DIG) or biotin-labeled dUTP can be used to permit detection of specific sequences. The labeled PCR products may, for example, be used as hybridization probes or detected by use of capture probes.

In many protocols, it will be desirable to simultaneously process one or more control droplets to determine the quality or fidelity of the reaction. Thus, for example, in order to ensure that contamination has not occurred one or more PCR-ready droplets without the sample template may be thermal cycled and otherwise processed in the same manner as droplets including the sample template. Detection of amplified nucleic acid in the control droplets would be indicative of contamination. Other control droplets may include known quantities or concentrations of template material, or known quantities or concentrations of fluorescent dye. Control droplets may be processed on the same droplet microactuator as the sample droplets, simultaneously with, before and/or after, processing of the actual sample droplet.

The system provides the possibility of independent software-based customization of reaction protocols and conditions for each sample or assay. This, combined with the scalability of the platform ensures that the capabilities of the system can be extended to include a wide range of nucleic acid targets.

The invention includes methods of conducting droplet operations on amplification reagents. For example, the invention includes a method of conducting one or more droplet operations on a droplet including buffer, primers, nucleotides, polymerases, and/or other PCR reagents. The invention also includes a method of conducting one or more droplet operations using a buffer droplet on a droplet microactuator including one or more primers. The invention also includes a method of conducting one or more droplet operations using a buffer droplet on a droplet microactuator including one or more nucleotides. The invention also includes a method of conducting one or more droplet operations using a buffer droplet on a droplet microactuator including one or more polymerases, e.g., DNA polymerases. The invention also includes a method of conducting one or more droplet operations using a buffer droplet on a droplet microactuator including one of more reverse transcriptases. In another embodiment, the invention includes a method of conducting one or more droplet operations using a buffer droplet on a droplet microactuator which includes 2, 3, 4 or more PCR reagents selected from the categories including primers, nucleotides, polymerases, and other PCR reagents. Further, the invention includes a method of conducting one or more droplet operations using a PCR-ready droplet including one or more buffers, primers, nucleotides, polymerases, and nucleic acid templates including a target nucleic acid sequence.

The droplet-based amplification protocols are also useful for analyzing RNA content. In some embodiments, RNA will be the initial target nucleic acid. A two buffer system may be used to provide one buffer for the reverse transcription (RT) step that creates cDNA from the viral RNA, and a different buffer selected to facilitate the DNA amplification step. In a related embodiment, a single buffer method is used in which a buffer is provided that is compatible for both reactions but not necessarily optimal for either.

In one embodiment, a droplet-based PCR can be executed on a droplet microactuator to quantitate the changes in gene expression levels for relevant cancer biomarkers, e.g., vascular endothelial growth factor (VEGF) and the cyclin-dependent kinase inhibitors p21(Cip1) and p27(Kip1). For example, cells in a droplet, whether suspended or bound to a surface, can be lysed. Freed poly(A) mRNA can be captured in droplets using beads, such as oligo (dT) magnetically responsive beads. Reagents are available from Dynal Biotech in its mRNA DIRECT Micro Kit. Mixing or agitation of droplets may be used to enhance cell lysis and enhance capture of poly (A) mRNA onto beads. mRNA from oligo (dT) magnetically responsive beads can be eluted by thermally melting the RNA-DNA duplex. The appropriate temperature depends on the length of the strand. Beads can be washed using droplet-based washing protocols as described elsewhere herein. PCR (e.g., qRT-PCR) can be performed using a droplet-based protocol on the droplet microactuator with the appropriate primers for the gene targets (e.g., VEGF, p21 (Cip1) and p27(Kip1)). Droplet-based RNA amplification may also be accomplished using the Van Gelder and Eberwine technique.

The invention provides droplet-based rolling circle amplification for DNA. In the rolling circle approach, a buffer droplet including a dsDNA his heated on a droplet microactuator to a temperature sufficient to result in denaturation of the dsDNA (typically about 95° C.). Incubation time may in some instances range from about 1 to about 10 minutes. A droplet including a circularizable probe is combined with the droplet including the denatured DNA to anneal and ligate the circularizable probe to the target dsDNA at an effective temperature (e.g., about 60° C.) in buffer with a polymerase (e.g., *T. flavus* DNA polymerase) and an appropriate ligase (e.g., Ampligase DNA ligase). Incubation may in some cases be less than about 45 minutes. The resulting droplet is combined with rolling circle primer, buffer, Ø29 DNA polymerase, at a decreased temperature (e.g., about 31° C.). Incubation time may in some cases range from about 2 to about 30 minutes. Biotin may be incorporated with the Ø29 DNA polymerase to capture the amplicon on a streptavidin bead or surface and visualized with a fluorescent probe.

The invention provides droplet-based strand displacement amplification (SDA) for DNA. In this embodiment, a buffer droplet including a dsDNA fragment with target specific amplification primers is heated on a droplet microactuator to a temperature sufficient to result in denaturation of the dsDNA (typically about 95° C.). Incubation time may in some instances be for less than about 4 minutes. The droplet is then cooled to an annealing temperature (e.g., about 37° C.) to result in annealing. Annealing time may in some cases be for less than about 4 minutes. The droplet is combined using droplet operations with a droplet including a restriction endonuclease and exo(minus) Klenow polymerase. The resulting droplet is isothermally incubated on the droplet microactuator at a temperature sufficient to result in DNA amplification (e.g., about 37° C.). Incubation time may in some cases be from about 1 to about 5 hours. Amplification can be detected using, for example, a fluorescent probe or a strand specific molecular beacon The invention provides droplet-based transcription mediated amplification or NASBA for RNA. In this embodiment, a droplet including a target nucleic acid is heated on the droplet microactuator to a temperature sufficient to denature the target (e.g., about 95° C.). Denaturation time may in some cases be less than about 4, 3, or 2 minutes. The droplet is then cooled to an appropriate temperature (e.g., about 41° C.), and combined using droplet operations with a droplet including add T7 RNA polymerase promoter-target primer 1 and target primer 2. The resulting droplet is combined using droplet operations with a droplet including reverse transcriptase, RNAse H and T7 RNA polymerase. The droplet temperature is then adjusted to a temperature sufficient to result in amplification of RNA amplicons. Amplification time may in some cases last for about 60 minutes.

One aspect of the invention is a droplet microactuator having a substrate for immobilization of a nucleic acid. In one aspect, the substrate is a gold substrate. Another aspect is a droplet microactuator including a substrate for immobilization of a nucleic acid and reagents for immobilizing the nucleic acid to the substrate. Yet another aspect is a droplet microactuator including a substrate for immobilization of a nucleic acid, reagents for immobilizing the nucleic acid to the substrate, and a nucleic acid sample. These reagents and samples, may for example, be stored in reservoirs on the droplet microactuator and/or in reservoirs or other containers off the droplet microactuator (e.g., in a cartridge). In yet another aspect, the invention involves a method of immobilizing a nucleic acid sample on a substrate comprising executing droplet operations to bring a droplet comprising the nucleic acid sample into contact with the substrate and thereby deposit in the nucleic acid sample on the substrate.

8.1.5 Downstream Analysis

In some embodiments, a droplet comprising amplified target nucleic acid may be transported downstream for further analysis. For example, the droplet may be transported and stream for analysis by micro gel electrophoresis. The micro gel electrophoresis may take place on or off the droplet microactuator.

In one embodiment, a two dimensional micro gel electrophoresis device, such as the device described by Mohanty et al. and the American Electrophoresis Society Annual Meeting (see http://aiche.confex.com/aiche/2005/techprogram/P30621.HTM).

In some embodiments, droplets including amplified nucleic acids are contacted with droplets including reagents sufficient to clone the amplified nucleic acids into suitable vectors. Vectors may be selected, for example, for use in gene libraries, and/or expression in cells.

8.2 Nucleic Acid Sequence Analysis

The invention provides methods, devices and systems for droplet-based nucleic acid sequence analysis on a droplet microactuator system which, among other things, avoids problems associated with the increasingly complex mixtures required by the approaches of the prior art.

Figure 3:
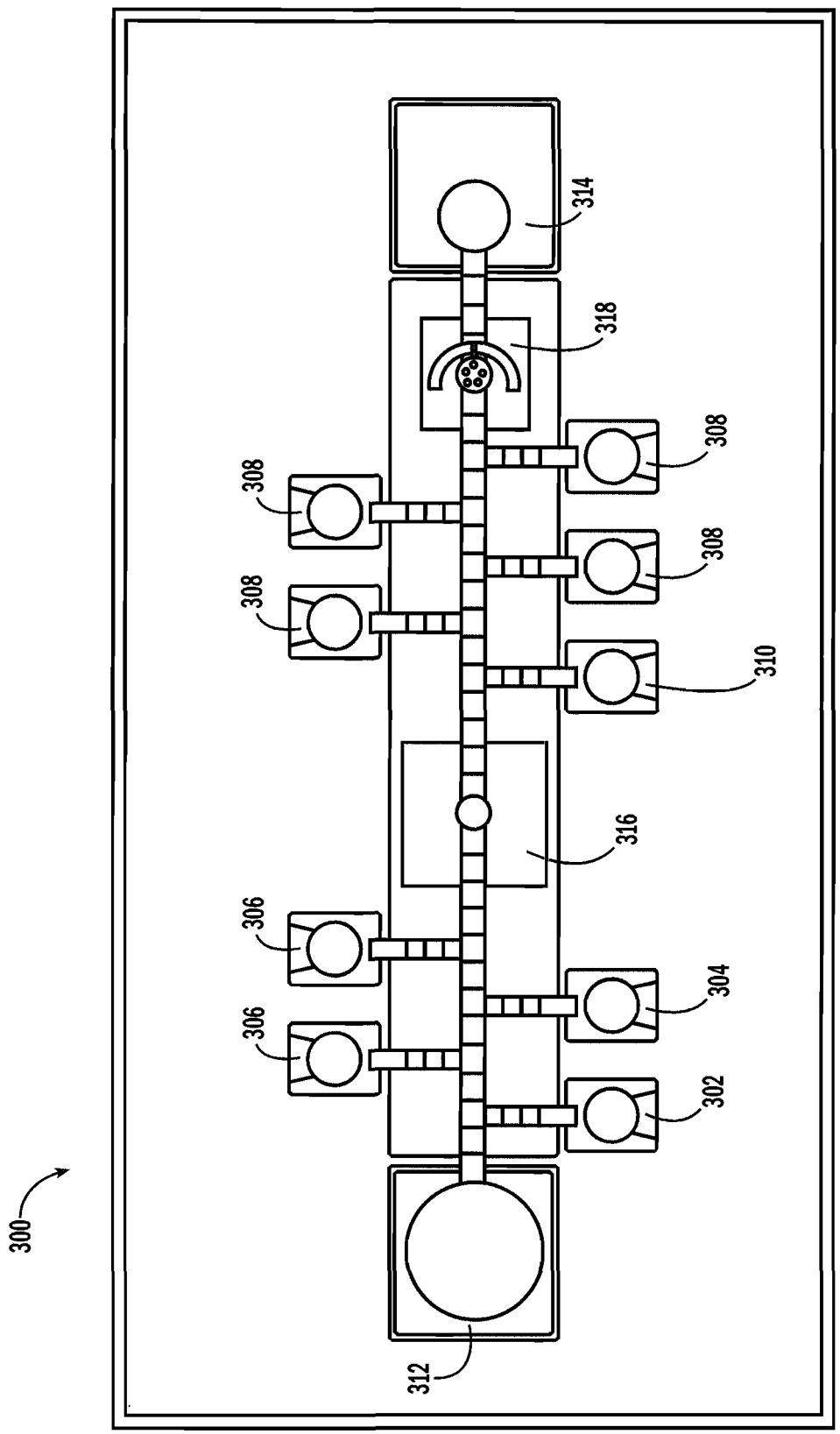
FIG. 3 is a top plan view of a droplet microactuator for use in nucleic acid sequence analysis in accordance with an embodiment of the present invention.

FIG. 3 illustrates an illustrative droplet microactuator 300 suitable for nucleic acid sequence analysis. In this embodiment, multiple fluid ports or reservoirs may be provided such as DNA input reservoir 302, DNA reagents reservoir 304, primer set reservoirs 306, nucleotide (e.g., dA, dC, dG, and dT) reservoirs 308, and pyrosequencing primer reservoir 310. Wash buffer reservoir 312 may also be provided, as well as waste area 314, thermal cycling area 316, and imaging area 318. Various thermal cycling area embodiments may employ a variety of heater configurations such as those described elsewhere herein. Imaging area 318 may utilize, for example, a photomultiplier tube (PMT).

Figure 4:
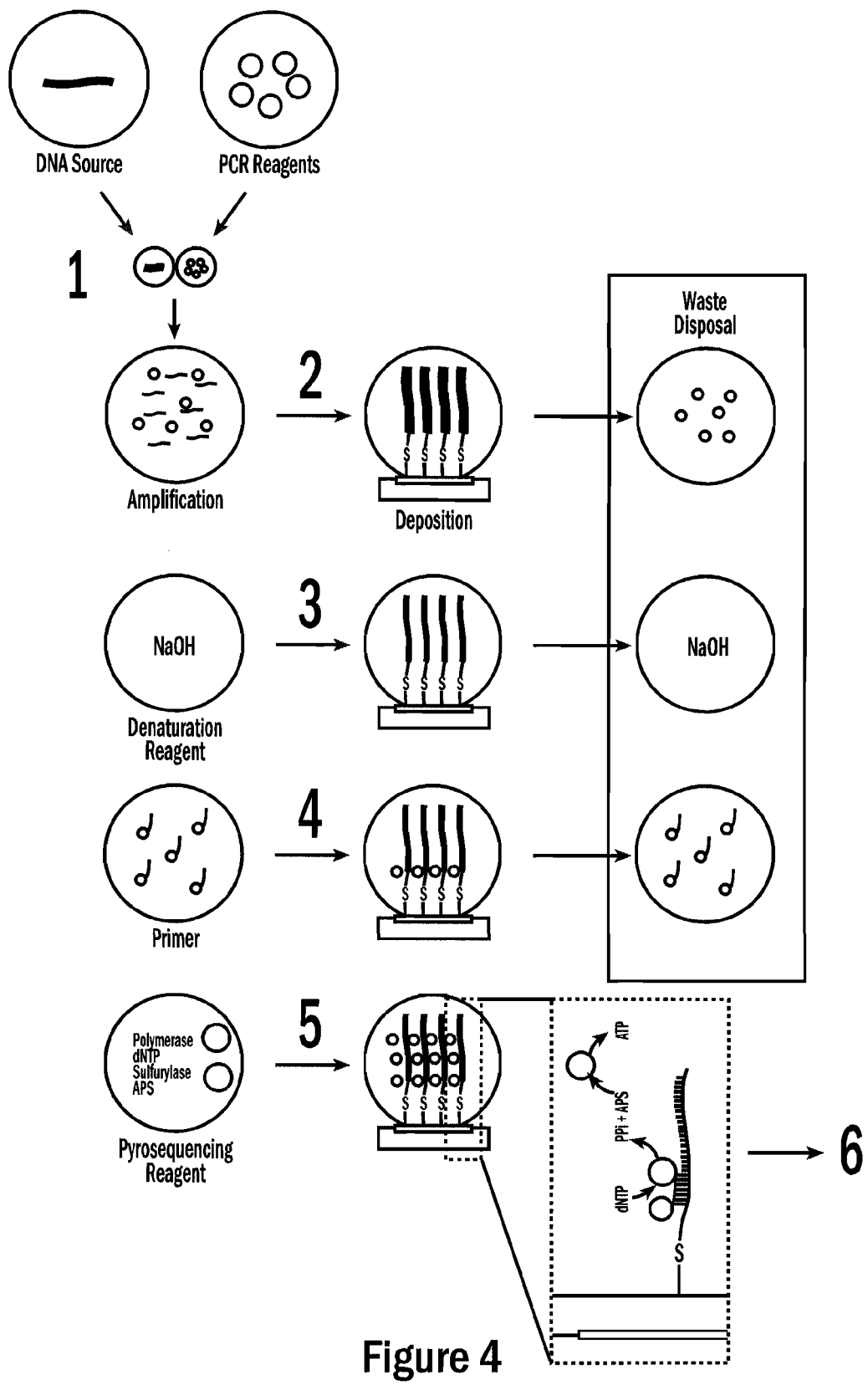
FIGS. 4 and 5 are illustrations showing reaction steps and droplet operations of an illustrative embodiment in accordance with the present invention.
Figure 5:
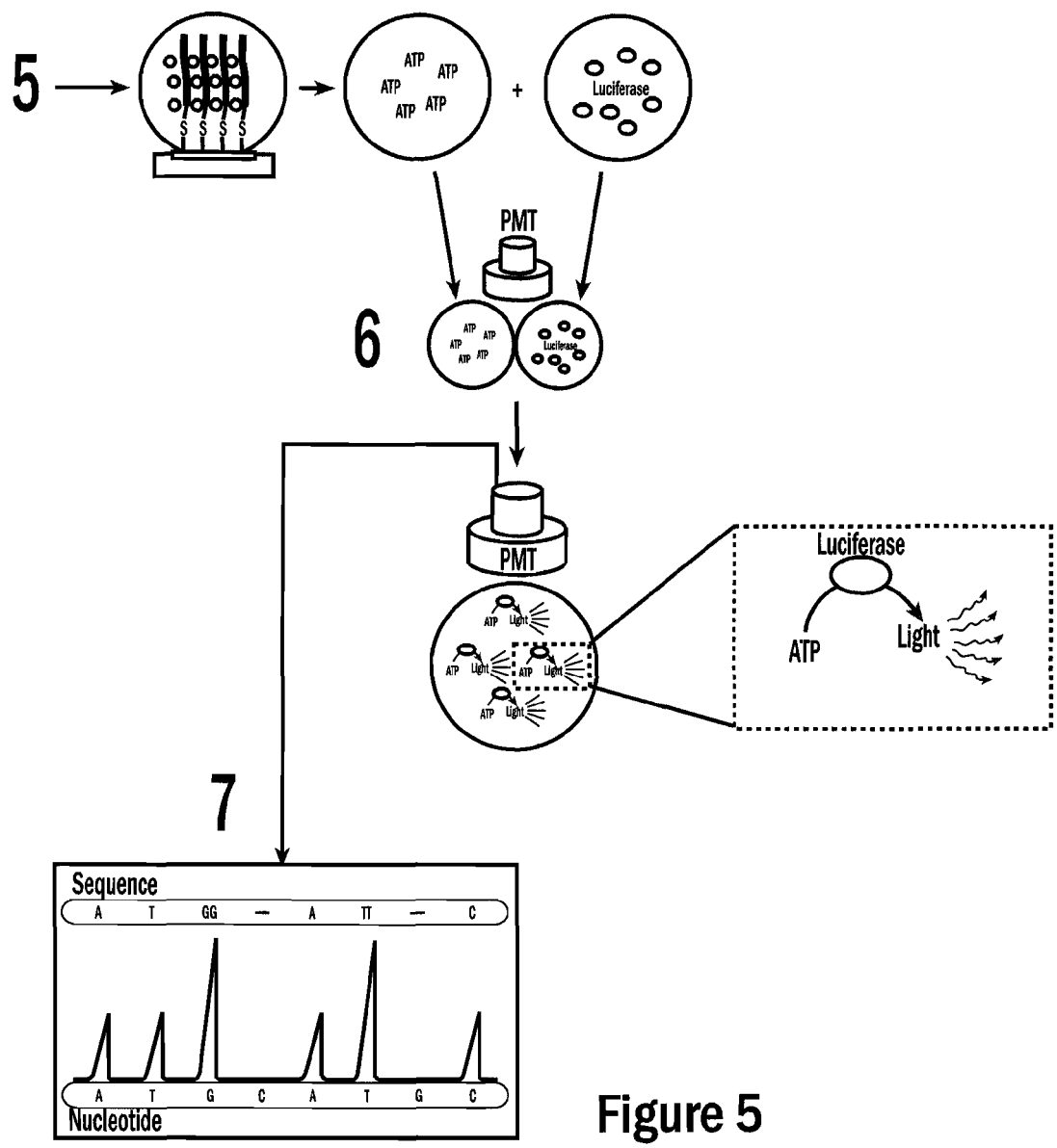

FIGS. 4 and 5 illustrate reaction steps and droplet operations of an illustrative embodiment of the invention. A nucleic acid sample may be amplified as needed (on or off the droplet microactuator) to obtain a sufficient concentration of nucleic acid for analysis. The nucleic acid sample may be introduced to a droplet microactuator where it is immobilized on a solid support. Reagents for denaturing the nucleic acid to single strand, priming and stepwise extension of the double stranded portion, may be transported to the immobilized nucleic acid using droplet microactuation techniques. Importantly, droplets including reaction products may be transported away from the immobilized nucleic acid, e.g., for further processing, analysis, and/or waste disposal. Importantly, detection may in some embodiments be conducted separately in time and space relative to the extension synthesis reactions. Among other things, this capability reduces or eliminates the build-up of certain degradation byproducts caused by existing methods. A further advantage of the invention is that detection can occur in proximity to a sensor to improve the efficiency of light collection and thus the sensitivity of the analysis.

The invention may include a droplet microactuator or droplet microactuator system having one or more input reservoirs loaded with reagents for conducting sequencing protocols. For example, one or more reservoirs may include reagents for conducting a pyrosequencing protocol. The invention also may include a droplet microactuator or droplet microactuator system, having one or more input reservoirs loaded with a sample for conducting a pyrosequencing protocol.

It will be appreciated that an important aspect of the invention involves the ability to conduct droplet operations using each of the sequence analysis reagents and/or samples on a droplet microactuator. For example, the invention may include:

(1) a droplet microactuator comprising thereon a droplet comprising any one or more of the reagents and/or samples described herein for conducting sequence analyses;
(2) a device or system of the invention comprising such droplet microactuator;
(3) a method of conducting droplet operations on or otherwise manipulating a droplet making use of such droplet microactuator or system; and/or
(4) a method of conducting an droplet-based sequence analysis protocol making use of such droplet microactuator or system.

For example, the droplet operations may include one or more of the following: loading a droplet into the droplet microactuator; dispensing one or more droplets from a source droplet; splitting, separating or dividing a droplet into two or more droplets; transporting a droplet from one location to another in any direction; merging or combining two or more droplets into a single droplet; diluting a droplet; mixing a droplet; agitating a droplet; deforming a droplet; retaining a droplet in position; incubating a droplet; heating a droplet; vaporizing a droplet; cooling a droplet; disposing of a droplet; transporting a droplet out of a droplet microactuator; other droplet operations described herein; and/or any combination of the foregoing. Various other methods, devices, systems, and other aspects of the invention will be apparent from the ensuing discussion.

8.2.1 Sample Amplification

Nucleic acid sequence analysis typically begins with a sample including an amplified nucleic acid analyte or with a sample that includes a nucleic acid analyte for amplification. For the latter, amplification can be performed using standard techniques and/or using droplet-based amplification on a droplet microactuator as described in Section 8.1. Amplification may be conducted on the same droplet microactuator used to conduct sequence analysis protocols and/or on a separate droplet microactuator. In some embodiments, a second droplet microactuator and is coupled in fluid communication with a sequence analysis droplet microactuator.

8.2.2 Nucleic Acid Immobilization

As illustrated in FIG. 4, the amplified nucleic acid sample may be immobilized within the droplet microactuator so that reagent droplets may be brought into contact with the immobilized nucleic acid. Immobilization may be on a surface of the droplet microactuator or on other surfaces within the microactuator, such as beads made from polymers, polymeric resins, and optionally including magnetically responsive materials.

Useful substrates for such attachment include glass, gold, polyacrylamide gels, polypyrrole, Teflon, and optical fibers. Materials may, for example, be provided as films, particles, matrices or beads. In one embodiment, the substrate includes magnetically responsive beads. The droplet microactuator can include a magnet or electromagnet for producing a magnetic field to manipulate (e.g., immobilize, release, or move) the magnetically responsive beads. For example, magnetically responsive beads can be agitated and immobilized on the microactuator using a magnetic field to enhance washing steps (see Section 8.6).

A wide variety of techniques may be used to immobilize molecules, such as DNA, to surfaces. Examples include those chemistries used to attach oligonucleotides to the surface of microarrays and chemistries used in solid phase synthesis techniques.

Nucleic acid samples may be thiolated and adsorbed to a gold substrate. Nucleic acids maybe thiolated, for example, by substituting a non-bridging internucleotide oxygen of a phosphodiester moiety with sulfur, e.g., as described in U.S. Pat. No. 5,472,881, by Beebe et al., entitled "Thiol Labeling of DNA for Attachment to Gold Surfaces," the entire disclosure of which is incorporated herein by reference. One or more droplets including the thiolated nucleic acid can be transported on the droplet microactuator to a gold surface where the thiolated nucleic acid sample will be deposited on the gold surface. The droplet including the thiolated DNA is brought into contact with the gold surface for a sufficient time for covalent bonds to form between the sulfur and the gold. Electroactuation techniques may be employed to increase the surface area of the droplet with the gold surface.

DNA sample can be biotinylated at the 5'-ends using a water soluble biotin ester or using a biotinyl phosphoramidite reagent. Biotinylated DNA can be captured on streptavidin coated substrates. Thus, a droplet including biotinylated DNA sample can be transported into contact with the streptavidin surface where the DNA will be captured and immobilized.

Chemistry has been described for immobilization of single stranded DNA on a substrate (S. Taira et al., "Immobilization of single-stranded DNA by self-assembled polymer on gold substrate for a DNA chip," *Biotechnol Bioeng*. 2005 Mar. 30; 89(7):835-8). In this approach, thioctic acid (TA) is covalently attached to poly(allylamine hydrochloride) (PAH) in sidechains to immobilize the polymer on a gold surface by self-assembly. N-hydroxysuccinimide-ester terminated probe single-stranded (ss) DNA is easily covalently immobilized onto a TA-PAH-coated gold surface. The surface may be covered with polyacrylic acid, which forms ion complexes with the TA-PAH, to reduce the cationic charge.

As illustrated in step 3 of FIG. 4, double stranded nucleic acid is treated with a denaturing reagent, such as NaOH solution, in order to yield single stranded sample. This step is illustrated as occurring after the immobilization step; however, it will be appreciated that denaturation may be effected by transporting a denaturing reagent into contact with the double stranded nucleic acid sample, before, during or after immobilization. Denaturation may also be performed by heating the sample to thermally melt the double-stranded complex.

One aspect of the invention is a droplet microactuator having a substrate for immobilization of a nucleic acid. Another aspect is a droplet microactuator including a substrate for immobilization of a nucleic acid and reagents for immobilizing the nucleic acid to the substrate. Yet another aspect is a droplet microactuator including a substrate for immobilization of a nucleic acid, reagents for immobilizing the nucleic acid to the substrate, and a nucleic acid sample. These reagents and samples, may for example, be stored in reservoirs on the droplet microactuator and/or in reservoirs or other containers off the droplet microactuator (e.g., in a cartridge). In one embodiment of a reservoir loading assembly, reagent and/or sample reservoirs (e.g., in vials or syringes) may be coupled in fluid communication with droplet microactuator reservoirs so that fluid from the vials may flow or be forced directly into the droplet microactuator reservoirs. This aspect of the invention is scalable, such that the number of reservoirs and reservoir loading assemblies may be increased as needed to include slots for as many reagents as required to conduct a desired protocol. Reagent/sample reservoirs and reagent/sample loading are discussed further in Sections 8.8.4 and 8.8.5.1.

8.2.3 Polymerase Facilitated Nucleotide Incorporation

As illustrated in steps 4 and 5 of FIG. 4, the immobilized, single stranded nucleotide sample is primed to yield a double stranded segment. Priming may, for example, be achieved by transporting a droplet comprising primer into contact with the immobilized sample.

The primed sample is reacted with a deoxynucleotide triphosphate (dNTP) in the presence of a polymerase. This reaction may be achieved by transporting one or more droplets including a deoxynucleotide triphosphate (dNTP) and a polymerase into contact with the immobilized sample. If the dNTP is complementary to the first base in the single stranded portion of the nucleic acid sample, the polymerase catalyzes its incorporation into the DNA strand. Each incorporation event is accompanied by release of pyrophosphate (PPi) in a quantity corresponding to the quantity of incorporated nucleotide. Incorporation events can thus be determined by measuring the PPi released. Addition of dNTPs is typically performed one at a time, each in a separate buffer. Nucleotide incorporation proceeds sequentially along each immobilized template as each nucleotide is made available in a preselected or programmed order.

A variety of native and modified polymerases may be used. Modified polymerases include, for example, native sequences with additions, insertions or replacements, that result in a polymerase that retains the capacity to facilitate incorporation of a nucleotide into a primed sample. The polymerase may be an exonuclease deficient polymerase. The large or Klenow fragment of DNA polymerase may also be used.

A dATP or ddATP analogue may be selected which does not interfere in the enzymatic PPi detection reaction but which nonetheless may be incorporated by a polymerase into a growing DNA chain without interfering with proper base pairing. Examples of suitable analogues include [1-thio] triphosphate (or α-thiotriphosphate) analogues of deoxy or dideoxy ATP, e.g., deoxyadenosine [1-thio]triphospate, or deoxyadenosine α-thiotriphosphate (dATPαS) as it is also known. These and other analogues are described in U.S. Pat. No. 6,210,891, by Nyren, et al., entitled "Method of sequencing DNA," the entire disclosure of which is incorporated herein by reference for its teaching concerning such analogues.

Single stranded binding protein may be included to extend the length of sequences that may be sequenced by reducing folding of the single stranded sample. Thus, for example, the invention includes a droplet microactuator including a droplet including single stranded binding protein. The droplet may be an amplification-ready droplet including single stranded binding protein. The invention includes methods of conducting droplet operations on a droplet including single stranded binding protein.

8.2.4 Detection of Nucleotide Incorporation

Determination of whether a specific base has incorporated at the target site may involve quantification of PPi released during the incorporation reaction. As each dNTP is added to a growing nucleic acid strand during a polymerase reaction, a PPi is released. PPi released under these conditions can be detected enzymatically e.g. by the generation of light in the luciferase-luciferin reaction (discussed further below). As the process continues, the complementary strand is assembled, and the nucleotide sequence is determined from the signal peaks. The system may produce a program, as illustrated in FIG. 5.

8.2.4.1 Conversion of PPi to ATP

In some cases, PPi released during an incorporation event may be detected indirectly. PPi quantification may, for example, be accomplished by quantifying ATP produced from APS in the presence of an enzymatic catalyst. ATP sulfurylase quantitatively converts PPi to ATP in the presence of adenosine 5' phosphosulfate (APS). Thus, in one embodiment, PPi can be converted to ATP, and the quantity of ATP can be measured to determine the quantity of dNTP incorporated during the reaction.

8.2.4.2 Ouantification of ATP

Once PPi is converted to ATP, the ATP can be quantified to measure the incorporation of dNTP. As illustrated in FIG. 5, ATP drives the luciferase-mediated conversion of luciferin to oxyluciferin that generates visible light in quantities that are proportional to the quantity of ATP. The light produced in the luciferase-catalyzed reaction may be detected, e.g., by a charge coupled device (CCD) camera, photodiode and/or photomultiplier tube (PMT). Light signals are proportional to the number of nucleotides incorporated. Detected signal can be translated into a system output corresponding to the results which is viewable by a user.

Luciferin-luciferase reactions to detect the release of PPi have been described. For example, a method for continuous monitoring of PPi release based on the enzymes ATP sulphurylase and luciferase referred to as Enzymatic Luminometric Inorganic Pyrophosphate Detection Assay ("ELIDA") has been described by Nyren and Lundin (Anal. Biochem., 151, 504-509, 1985, the entire disclosure of which is incorporated herein by reference.) The use of the ELIDA method to detect PPi in a droplet on a droplet microactuator is one aspect of the present invention. The method may however be modified, for example by the use of a more thermostable luciferase (Kaliyama et al., 1994, Biosci. Biotech. Biochem., 58, 1170-1171, the entire disclosure of which is incorporated herein by reference). Examples of suitable detection enzymes for the PPi detection reaction are ATP sulphurylase and luciferase.

In certain prior art applications, a nucleotide degrading enzyme, such as apyrase, is used to degrade unincorporated dNTPs and excess ATP. When degradation is complete, another dNTP is added. Since the reaction takes place in a single solution, waste products continue to build up as sequencing proceeds. An important aspect of the present invention is that it avoids the requirement for a nucleotide degrading step. Thus, while in some aspects of the invention, a nucleotide degrading step may be included, in other aspects, the systems and methods of the invention specifically omit a nucleotide degrading step. Thus, for example, the analysis may be accomplished in the absence of a substantial amount of nucleotide degrading enzyme, e.g., in the absence of a substantial amount of apyrase.

Further, the inventors believe that conducting the incorporation/conversion/detection reactions in the absence of substantial build-up of byproducts will produce a more predictable result. Thus, for example, where single nucleotide stretches are present in the sample, it is traditionally difficult to distinguish the specific number of incorporations as the length of the single nucleotide stretch increases. The inventors believe that the clean nature of the reaction of the present invention will lead to greater accuracy and reproducibility for longer single nucleotide stretches. Thus, for example, the inventors believe that the method of the invention can accurately detect single nucleotide stretches having 6, 7, 8, 9 10, 11, 12, 13, 14, 15 or more nucleic acids with 90, 95, 99 or 99.9% accuracy.

8.2.5 Droplet Operation Protocols

It will be appreciated that, in addition to the protocols described above, a variety of droplet operation protocols may be utilized in order to carry out the sequence analyses of the invention. Thus, for example, conversion to ATP can be accomplished in a single reaction along with the dNTP incorporation reaction, or the reactions can be performed stepwise: (1) incorporation of dNTP to release PPi, followed by (2) conversion of PPi to ATP. Where the incorporation and conversion steps are performed together, the system may transport a single droplet including the required reagents (dNTP, polymerase, ATP sulfurylase, and APS). Thus, all reagents required to incorporate a dNTP into the immobilized sample, release PPi, and react the PPi with APS to yield ATP may be included in a reservoir on the droplet microactuator as a single source reagent for each nucleotide. The source reagent for each nucleotide may be successively brought into contact with the immobilized sample so that the reactions may take place, yielding ATP in the presence of a complimentary dNTP.

Where the incorporation and conversion steps are performed separately, the primer, polymerase, dNTP, sulfurylase, and APS may be provided from separate sources as separate reagent droplets which are merged together to perform the reactions of the invention. Alternatively, some or all of these reagents may be provided from a single source as a pyrosequencing reagent droplet which is brought into contact with the immobilized sample in order to conduct the reactions of the invention. For example, a droplet including the dNTP and polymerase may be brought into contact with the immobilized sample, so that the base will incorporate if complimentary, thereby releasing PPi. The droplet potentially including the PPi may then be transported away from the immobilized sample and combined with a droplet including the ATP sulfurylase and APS to produce ATP. Alternatively, a droplet including the ATP sulfurylase and APS may be combined with the droplet potentially including the PPi in the presence of the immobilized sample to produce ATP.

Further, while FIG. 4 illustrates the priming step 4 and incorporation/conversion steps 5 as occurring sequentially, it will be appreciated that they can be separated out further or they can all be incorporated into a single step. In other words, each specific reagent may be added to the reaction at the appropriate time in one or more droplets or any combination of multiple reagents may be provided together in a single droplet or series of droplets. Thus, in one embodiment, the droplet microactuator transports one or more droplets into contact with the single stranded sample, wherein one or more droplets together include the following reagents (or their functional equivalents) provided together or in separate droplets: primer, polymerase, and dNTP in any combination and in any order producing the result that the primer hybridizes with the sample to form a double stranded portion, the polymerase catalyzes incorporation of any complimentary dNTP into a target site at the first single stranded base position adjacent to the double stranded portion, thereby releasing PPi.

In another embodiment, the droplet microactuator transports one or more droplets into contact with the single stranded sample, and the one or more droplets together include the following reagents (or their functional equivalents): primer, polymerase, dNTP, sulfurylase, and APS, in any combination and in any order producing the result that the primer hybridizes with the sample to form a double stranded portion, the polymerase catalyzes incorporation of any complimentary dNTP into a target site at the first single stranded base position adjacent to the double stranded portion, thereby releasing PPi, and the ATP sulfurylase converts any PPi to ATP in the presence of APS. Base incorporation is determined by quantifying the quantity of PPi released.

The droplet potentially comprising ATP may be merged via droplet microactuation techniques with a droplet comprising reagents, such as luciferase and luciferin, for facilitating detection of any ATP. Similarly, a droplet including luciferin and potentially comprising ATP may be merged via droplet microactuation techniques with a droplet including luciferase for detection of any ATP. Further, a droplet including luciferase and potentially comprising ATP may be merged via droplet microactuation techniques with a droplet including luciferin for detection of any ATP.

Droplets for the detection reaction may be merged in the presence of or apart from the immobilized sample. For example, a luciferase/luciferin droplet may be merged with the droplet potentially including ATP in the presence of the immobilized sample. Alternatively, the droplet potentially including ATP may be separated from the immobilized sample to be merged with a luciferase/luciferin droplet. In either case, the merging of droplets including reagents that produce a light signal may be accomplished in proximity to the sensor in order to maximize the amount of light detected.

When the droplet potentially including ATP is transported away from the immobilized sample to be merged with a luciferase droplet, the transport step may include an incubation step in order to maximize the production of ATP for detection in the fluorescence reaction. In other words, this incubation may be accomplished during transport, or the droplet may be temporarily stored for incubation prior to the fluorescence reaction. The droplet microactuator may include an incubation zone for this purpose. The incubation zone may or may not include a heating element to control temperature in the zone. The incubation zone may or may not include a wall separating the zone from the remainder of the droplet microactuator. The incubation zone may include an array of electrodes to facilitate transport of droplets into and out of the zone. The zone is scalable and may include electrodes for transporting and storing tens, hundreds or more droplets within the incubation zone.

In the practice of the invention, one or more detection reagents may be specifically excluded from the polymerase reaction step so that any signal will not be emitted during the polymerase reaction. For example, in one embodiment, a detection enzyme is not added to the reaction mix for the polymerase step. Instead, the droplet used to conduct the polymerase step is transported away from the immobilized sample, then merged with a droplet including the detection enzyme in range of a sensor for detecting signal from any resulting reaction.

The reaction mix for the polymerase reaction may thus include at least one dNTP, polymerase, APS, and ATP sulfurylase, and may optionally include luciferin, while lacking any significant amount of luciferase. In this way, the dNTP incorporation reaction may be separated from the detection reaction. The detection reaction may thus be conducted in the presence of the sensor, e.g., as illustrated in FIG. 5, in order to maximize the detection signal. For example, where the detection signal includes light, the detection reaction may be completed in range of a sensor for detecting light emitted from any resulting light-producing reaction.

Further, a detection reaction and a subsequent incorporation reaction may be conducted in parallel, thereby expediting sequencing speed. Similarly, an incorporation reaction may be conducted, the output of a previous incorporation reaction may be incubated, and the output of a previous incubation may be subjected to detection all in parallel in separate droplets, thereby expediting sequencing speed.

Unlike certain processes of the prior art, the droplet microactuator approach of the present invention avoids mass transport effects. Reagents may be brought directly into contact with each sample, without requiring a flow of reagents across multiple samples. Where magnetically responsive beads are used, they may be maintained in place using a magnetic field and/or they may be transported from place-to-place in droplets. Reagents may be transported from a reagent source directly to a sample without coming into contact with other samples and potentially causing cross-contamination. Diffusion of byproducts is avoided by isolation of droplets in the filler fluid. Wells packed with beads, e.g., stabilizing beads, which may interfere with light detection may also be avoided. A wash containing apyrase may be used between applications of nucleotides, but its use is not necessary in the practice of the invention, and in some embodiments, it is specifically avoided.

Between applications of each new set of reagents to the immobilized sample, it may be washed, e.g., with a buffer solution. Various surface washing protocols are described in Section 8.6.

8.2.6 Applications

The nucleic acid amplification and sequencing methods, devices and systems of the invention are useful in a wide variety of settings, such as scientific research, medical and veterinary diagnostics, pharmacogenomics, genomic sequencing, gene expression profiling, detection of sequence variation, forensics, and environmental testing. Due to the portable size enabled by the droplet microactuator of the invention, sequencing for the applications described herein can, if desirable, be accomplished at the point-of-sample collection.

In one embodiment, the invention may provide an influenza test panel. In this embodiment, the system may accept a biological sample as input, process the sample to prepare target influenza virus nucleic acids for amplification, conduct amplification using the protocols of the invention, and detect the presence of target influenza nucleic acids. The biological sample may, for example, be collected from a nasopharyngeal swab.

In another embodiment, the invention may provide a respiratory infection panel. In this embodiment, the system may accept a biological sample as input, process the sample to prepare nucleic acids from common respiratory pathogens, such as bacteria, viruses and/or fungi, for amplification, conduct amplification using the protocols of the invention, and detect the presence of target respiratory pathogen nucleic acids. In an extended version of the respiratory infection panel, the panel may include testing for atypical infections such as those affecting immuno-compromised patients. The biological sample may, for example, be provided by or obtained from a nasopharyngeal swab. Examples of respiratory pathogens suitable for detection using a respiratory infection panel of the invention include *S. pneumoniae, H. influenzae, Legionella, Chlamydia, Mycoplasma*; viruses such as influenza, RSV, coronavirus, parainfluenzae, adenovirus, metapneumovirus, bocavirus, hantavirus; and fungi such as *Pneumocystis, Aspergillus, Cryptococcus*.

For sequencing lengthy nucleic acids, e.g., whole genomes, samples may be broken into smaller overlapping fragments (e.g., 100-1000 bp, 200-900 bp or 300-800 bp), e.g., by digestion with restriction enzymes. The smaller fragments may be analyzed using the systems and methods of the invention. Results may be assembled and edited to reconstruct the longer sequence, e.g., by identifying and matching overlaps in the sequenced fragments. Analysis of the fragments may proceed in a parallel manner, in order to expedite the sequencing. Each template may be sequenced multiple times to enhance accuracy. In this way, entire chromosomes or even entire genomes may be accurately sequenced.

Genes transcribed in a given set of tissues can be determined from mRNA extracted from cells or tissue. mRNA may be copied into DNA (cDNA) using reverse transcriptase. The resulting cDNAs may be cloned, and the clone ends from a cDNA library may be sequenced according to the methods of the invention to generate EST, which provide an expression profile for the tissue from which the mRNA was extracted. RNA patterns may in some cases be correlated with disease states and may be sequenced as a diagnostic tool. RNA viruses may also be sequenced.

Once a reference sequence has been obtained for a region of interest (e.g., a gene believed to be involved with a disease), variations of the sequence as found in different individuals or closely related species can be identified by selectively resequencing a small portion of known sequence. Variations may, for example, occur as SNPs; size differences (insertions/deletions); copy number differences (duplications) and rearrangements (inversions, translocations).

Populations of organisms can be sequenced, e.g., from water, soil and/or atmospheric samples. For example, most current knowledge of microbiology still is derived from individual species that either cause disease or grow readily as monocultures under laboratory conditions and are thus easy to study. Sequencing can be used to study the organization, membership, functioning, and relationship of such organisms. Qualitative analysis of sequence and gene diversity can thus be obtained from organisms that cannot be cultured using conventional techniques.

The systems and methods of the invention may also be used to provide genomically specific diagnostics and treatment. For example, the systems may be used to identify genotypic traits that are associated with more or less favorable treatment outcomes. Results may be used to guide treatment decisions. Similarly, the systems and methods of the invention can be used to identify identifying mutations in infectious organisms or genetically damaged or altered cells, such as cancers and other neoplasms, and this information can be used to guide or confirm treatment decisions. Infectious organisms may, for example, include viruses, bacteria, parasites or fungi. The invention provides, for example, a system and method for quick, inexpensive detection of drug resistant strains of bacterial or viruses (e.g., new strains of drug-resistant HIV) which is a critical component of combating these disease causing organisms.

The systems and methods of the invention may be employed for genetic testing, e.g., to identify DNA segments in a subject that play a role in a specific disease or DNA segments which may be predictive of a specific disease. For example, linkage may be demonstrated when, within families, one form of the marker is found in those with the disease more often than in blood relatives in whom the disease is absent. Such methods have proved successful in Huntington disease, cystic fibrosis, breast cancer, and other disorders. Thus, for example, the systems and methods of the invention may be used to identify mutations in a gene that are only present (in gene dosage sufficient to cause disease) in subjects with disease or subjects predisposed to develop the disease. In another embodiment, the systems and methods of the invention are used to identify genetic variations for which (1) there is a statistically significant probability that the sequence will be present in people with the disease, and (2) there is a statistically significant probability that the sequence will not be present in people without the disease. Similarly, the systems and methods of the invention are used to identify genetic variations for which there is a statistically significant probability that people with positive test results will get the disease and that people with negative results will not get the disease. Further, the systems and methods of the invention may be used to sequence a segment of DNA to identify one or more SNPs.

The systems and methods of the invention may be used in a clinical trial setting. For example, nucleic acids from persons participating in a trial may be sequenced, and adverse events may be compared with genetic variation in the trial group to identify a subset of participants with increased susceptibility to one or more adverse events. Depending on the severity of the particular adverse event in question, subjects with the associated genetic variation may, for example, be watched more closely, receive further protective treatment, and/or removed from the trial altogether. Similarly, efficacy may be compared with genetic variation in the trial group to identify a subset of participants with increased likelihood to positive treatment outcomes. Target populations can be defined based on positive outcomes and/or lack of unduly adverse events. Products can be labeled accordingly. Physicians can test their patients for the associated genetic variation and can prescribe products only to the population subset for which treatment is pharmaceutically acceptable.

The invention is also useful for forensic evaluations, such as: identifying potential suspects whose DNA may match evidence left at crime scenes; exonerating persons wrongly accused of crimes; identifying crime and catastrophe victims; establishing paternity and other family relationships; identifying endangered and protected species as an aid to wildlife officials; detecting bacteria and other organisms that may pollute air, water, soil, and food; matching organ donors with recipients in transplant programs; determining pedigree for seed or livestock breeds; and authenticating consumables such as caviar and wine; identifying genetically modified foods.

Other examples of applications include: testing for associations between genetic variations and subject outcomes, e.g., efficacy, side effect profile, pharmacokinetics, and/or pharmacodynamics, in the drug discovery process; analyzing a subject's genetic profile to differentiate between potential drug therapies based on genotypic variation; screening for predisposition for disease so that a subject can take steps to monitor, treat, avoid or lessen the severity of a genetic disease; screening to decrease the number of adverse drug reactions in a patient population; screening to enable the use of a drug which is not safe in a genetically identifiable population subset; and monitoring of gene therapies.

8.3 Affinity-Based Assays

The invention provides methods, devices and systems for conducting droplet-based, affinity-based assays, such as affinity-based assays. These assays include any assay in which a compound having a binding affinity for an analyte is contacted with the analyte or a sample potentially including the analyte using droplet operations. For example, the compound having a binding affinity for an analyte may be provided in a droplet and transported into contact with an analyte which is present in another droplet on a droplet microactuator or is immobilized on a surface of a droplet microactuator. As another example, the compound having binding affinity for the analyte may itself be immobilized on the surface of a droplet microactuator and/or on the surface of beads included on a droplet microactuator, and a droplet including the analyte or potentially including the analyte may be brought into contact with the immobilized antibody.

It will be appreciated that a wide variety of affinity-based assay protocols are possible within the scope of the invention. Examples of affinity-based assay formats include direct affinity-based assays, indirect affinity-based assays, and competitive affinity-based assays. The assays may be employed to detect the presence of a target analyte, and may also in some cases be used to quantify the target analyte present in a sample. In a competitive assay, a droplet including a sample antibody and labeled antibody is contacted with a surface. The sample antibody competes with labeled antibody for binding to antigen adsorbed onto the surface. A variant of this approach involves linking the antigen to the surface via an intermediary linker. For example, the linker may be an antibody. The capture bridge assay uses a droplet including a sample antibody to link antigen adsorbed to the surface with antigen in solution. Another approach involves the use of biotinylated antigen and a streptavidin coated solid phase. Another approach involves binding the sample antibody to antigen immobilized on the solid phase. The bound antibody may be detected with isotype specific labeled second antibody. Excess antibody can be washed off using the droplet protocols of the invention.

It will be appreciated that an important aspect of the invention involves the ability to conduct droplet operations using each of the required affinity-based assay reagents and/or samples on a droplet microactuator. For example, the invention includes:

(1) a droplet microactuator comprising thereon a droplet comprising any one or more of the reagents and/or samples described herein for conducting affinity-based assays;
(2) a device or system of the invention comprising such droplet microactuator;
(3) a method of conducting droplet operations on or otherwise manipulating a droplet making use of such droplet microactuator or system; and/or
(4) a method of conducting an droplet-based affinity-based assay making use of such droplet microactuator or system.

For example, the droplet operations may include one or more of the following: loading a droplet into the droplet microactuator; dispensing one or more droplets from a source droplet; splitting, separating or dividing a droplet into two or more droplets; transporting a droplet from one location to another in any direction; merging or combining two or more droplets into a single droplet; diluting a droplet; mixing a droplet; agitating a droplet; deforming a droplet; retaining a droplet in position; incubating a droplet; heating a droplet; vaporizing a droplet; cooling a droplet; disposing of a droplet; transporting a droplet out of a droplet microactuator; other droplet operations described herein; and/or any combination of the foregoing. Various other methods, devices, systems, and other aspects of the invention will be apparent from the ensuing discussion.

8.3.1 Samples and Sample Preparation

The invention provides droplet-based affinity-based assays which are useful for detection of a wide variety of analytes. For example, any analyte that can bind with specificity to an affinity molecule, such as an antibody, is suitable for detection using the systems of the invention. A single sample may be analyzed for one or more target analytes. Analytes may, for example, be biological analytes or synthetic analytes. Examples include analytes in the following categories: analytes from human sources, analytes from animal sources, analytes from plant sources, analytes from bacterial sources, analytes from viral sources, and analytes from spore sources. Analytes may, for example, include proteins, peptides, small molecules, and various biomolecules, such as carbohydrates, lipids, and the like. In one embodiment, samples are contacted with immobilized antibody (e.g., antibody immobilized on beads), prior to introduction of the immobilized antibody onto the droplet microactuator.

Figure 6:
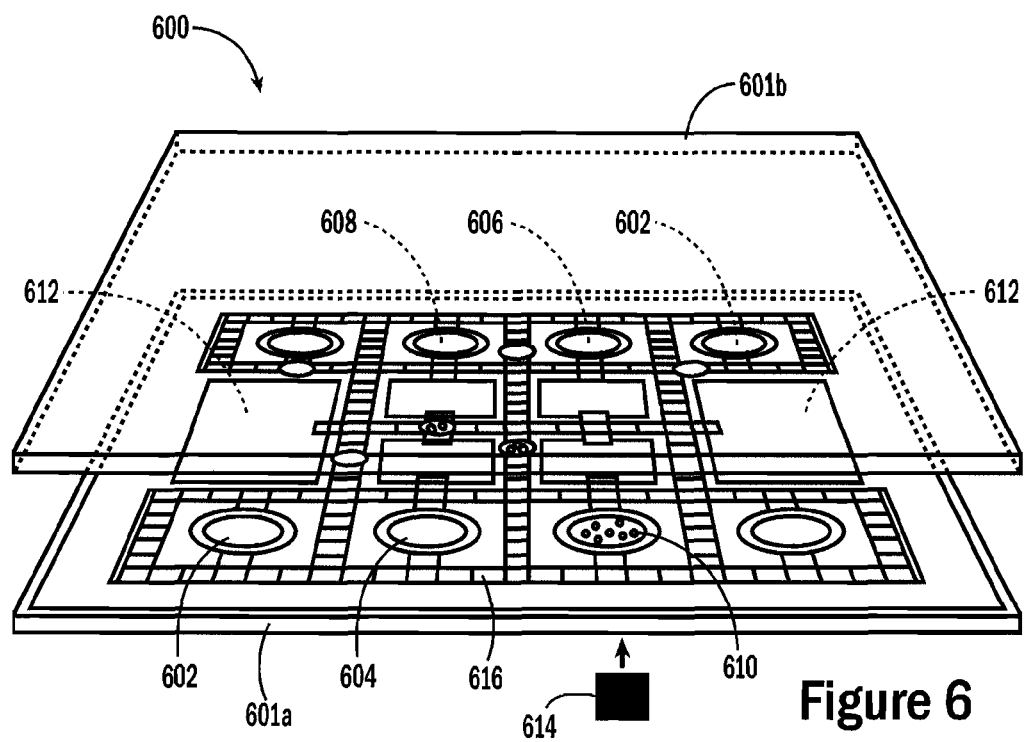
FIG. 6 is a perspective view of a droplet microactuator for use in conducting immunoassays in accordance with an embodiment of the present invention.

An illustrative droplet microactuator 600 suitable for conducting immunoassays is illustrated in FIG. 6. This embodiment may employ two substrates, a first substrate 601$a$ and a second substrate 601$b$ spaced apart in a substantially parallel fashion to provide an intervening space. Multiple fluid ports or reservoirs may be provided in the intervening space, such as wash buffer reservoirs 602, sample reservoir 604, primary antibody reservoir 606, secondary antibody reservoir 608, and immobilized antibody (e.g., antibody immobilized on beads) reservoir 610. Waste areas 612 may also be provided, as well as a magnet 614 positioned in a manner which permits interaction between the magnet's magnetic field and magnetically responsive components located in the intervening space. In this particular embodiment, transport electrodes 616 are provided on the first substrate.

8.3.2 Sandwich Affinity-Based Assay

Figure 7:
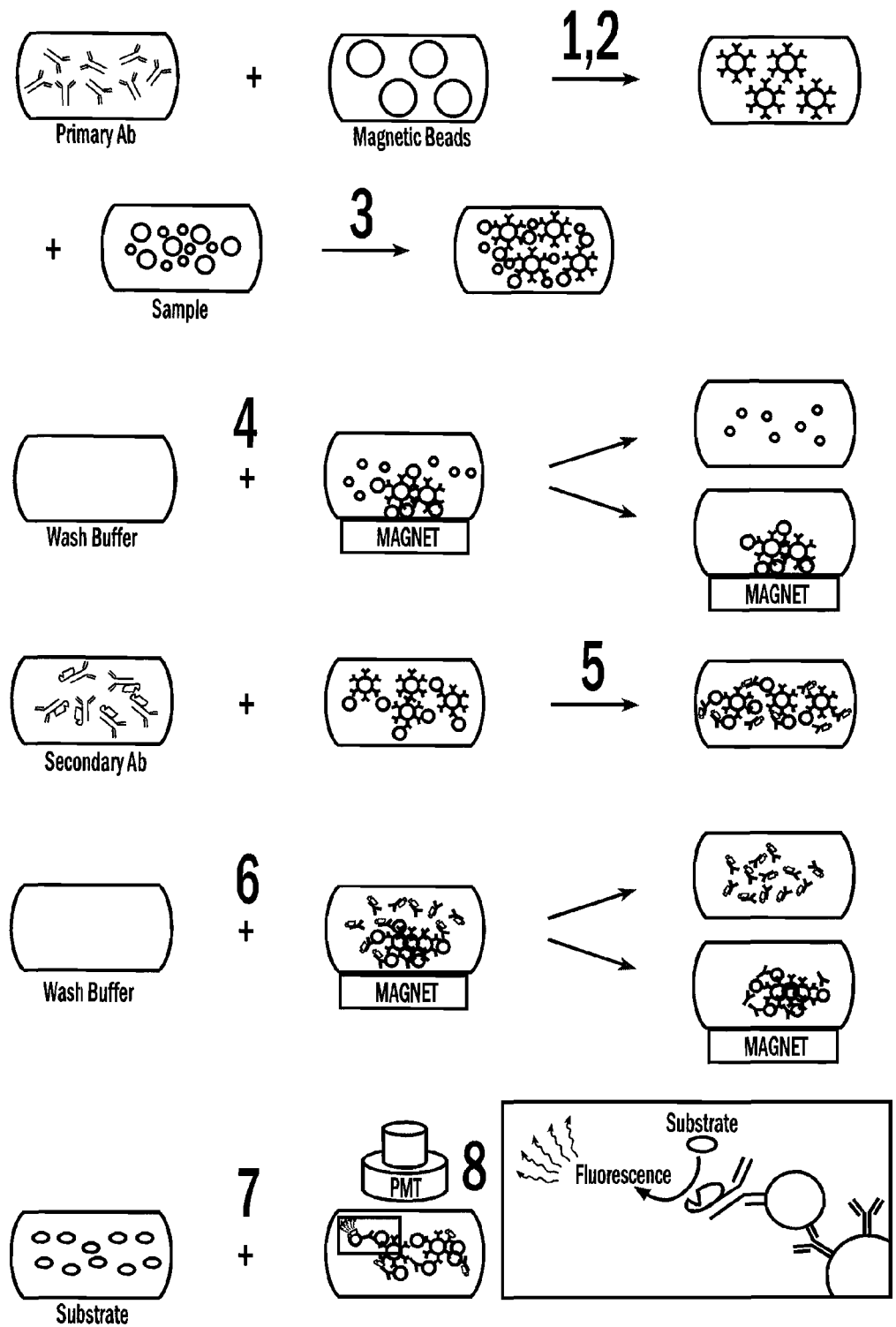
FIG. 7 is an illustration showing steps for conducting a droplet-based sandwich affinity-based assay performed on a droplet microactuator in accordance with an embodiment of the present invention.

In one embodiment, the invention provides a droplet-based sandwich affinity-based assay performed on a droplet microactuator. It will be appreciated that a wide variety of protocols are possible within the scope of the invention for conducting sandwich affinity-based assays. The following droplet-based protocol, which is based on the FIG. 7 illustration, is provided as one example only and is not intended to be limiting of the scope of the invention:

(1) immobilizing on a surface an antibody (primary) with specificity for a target analyte;
(2) washing the immobilized antibody, e.g., using a droplet-based washing protocol, to remove excess antibody;
(3) using droplet operations to expose the immobilized antibody to a sample droplet potentially including the target analyte with binding affinity for the immobilized antibody;
(4) washing the immobilized antibody-target analyte complex, e.g., using a droplet-based washing protocol, to remove unbound components of the sample droplet;
(5) exposing the immobilized antibody (now potentially including the target analyte bound thereto) to a droplet including a reporter (secondary) antibody;
(6) washing away excess reporter antibody, e.g., using a droplet-based washing protocol;
(7) optionally, performing additional steps to provide a measurable parameter or signal;
(8) measuring the measurable parameter or signal; and
(9) providing an output indicative of the signal.

Any one or more of the foregoing steps can be performed using droplet operations on a droplet microactuator as described herein.

8.3.2.1 Immobilizing Antibody

A primary antibody is immobilized on a surface. The surface may, for example, be a surface of the droplet microactuator, or the surface of beads, such as magnetically responsive beads, non-magnetically responsive beads, or particles, such as nanoparticles.

Immobilization of the antibody to the surface can be accomplished on the droplet microactuator using droplet-based protocols. For example, reagents for immobilizing an antibody to a surface may be introduced to the droplet microactuator, dispensed as discrete droplets and transported into contact with the surface for deposition. Where the surface in question is the surface of one or more beads, the beads may be introduced to the droplet microactuator, dispensed as buffer droplets, transported on the droplet microactuator, and merged with one or more droplets including reagents for immobilizing the droplets on the surface of the beads.

Alternatively, the antibodies may be immobilized off the droplet microactuator. For example, antibodies may be immobilized on beads prior to introduction to the droplet microactuator. A variety of protein-coated (e.g., streptavidin) and antibody-coated beads are commercially available. In another embodiment, antibodies may be immobilized on a surface of the droplet microactuator, e.g., during manufacture of the droplet microactuator.

Further, surfaces may be prepared for immobilization of antibodies. For example, a surface may be provided including moieties which have an affinity for an antibody or a binding moiety coupled to an antibody. The antibody, optionally including the binding moiety, may be brought into contact with the surface thereby immobilizing the antibody on the surface. For example, beads pre-coated with streptavadin may be introduced to the droplet microactuator. Droplet operations may be conducted with droplets including the streptavadin-coated beads, and may be employed to bring such bead-containing droplets into contact with one or more droplets including biotinylated antibody to thereby couple the antibody to the beads. As another example, the droplet microactuator may include a streptavidin coated surface on a droplet microactuation path, such that droplet operations may be employed to bring a droplet including biotinylated antibody into contact with the streptavidin coated surface and thereby immobilize the antibody on the surface. In a yet another example, capture antibodies can be selectively immobilized onto the surface of the droplet microactuator, e.g., by patterning the surface to enable immobilization of antibodies or by coupling photoactive species directly to the antibodies or to streptavidin and then immobilizing the antibody selectively by using a direct-write light system or using an optical mask or using other means to selectively expose light.

A wide variety of techniques are available for binding antibodies to surfaces. For example, the surface may be activated with Protein G to enable the binding of antibody molecules via their Fc domain, leaving the variable region available for target capture. Antibody may be covalently bound to latex surfaces by reaction of activated antibody with 1,3-diaminopropane coupled, polystyrene aldehyde/sulfate latex. Surfactant-free sulfate white polystyrene latex beads may be coated with antibody by incubation with antibody and conjugation buffer (30 mM $Na_2CO_3$, 70 mM $NaHCO_3$, pH 9.5). Biotinylated antibodies can be captured on streptavidin coated substrates. Antibodies may be covalently bound to a modified surface of the droplet microactuator such as a silane or thiolated layer. Antibodies may be covalently bound to a modified surface of the droplet microactuator (e.g., during assembly or using droplet operations to deposit the antibodies on the surface), such as a surface modified with silane or a thiolated surface.

8.3.2.2 Binding Target Analyte to Immobilized Antibody

A sample droplet is contacted with the immobilized antibody to permit any target analyte present in the sample to bind with the immobilized antibody. This step may be accomplished using droplet operations to transport a sample droplet into contact with the surface on which the antibody is attached, e.g., a droplet including antibody coated beads or a surface of the droplet microactuator on which the antibody is immobilized. In an alternative embodiment, the surface is a beads surface, and the bead is contacted with the sample prior to introduction into the droplet microactuator. The bead may also be washed prior to introduction into the droplet microactuator. The antibody binds to analyte from the sample droplet. The binding process may be expedited by increasing the speed of mass-transport. A few examples of accelerating mass transport include transport of the droplets at a high speed to enable thorough mixing of the beads with antibodies and the target analyte or to replenish the surface of immobilized antibody with target analytes. Other means include agitating the incubated droplet in-place by electrically manipulating the droplet or by a number of external means such as piezoelectric methods of actuation. In absence of any means of mass transport, the binding events occur based on diffusion and it could take longer times thereby prolonging the assay times. The immobilized antibody (e.g., the beads or the surface) may in some embodiments be subjected to a washing protocol on the droplet microactuator, e.g., as described in Section 8.6, to remove excess sample or other materials.

8.3.2.3 Binding Reporter Antibody to Target Analyte

After washing (e.g., the beads or the surface), a droplet comprising a reporter antibody having affinity for a different epitope on the analyte may be brought into contact with the washed immobilized antibody potentially having the captured analyte. The labeled antibody conjugate includes an antibody coupled to a reporter molecule, such as a radioactive molecule, an enzyme capable of catalyzing a detectable reaction (e.g., a color change, chemiluminescence, fluorescence, chemiluminescence, or electrochemical), a chemiluminescent molecule, or a fluorescent molecule. Depending on the reporter used, the immobilized antibody (e.g., beads or other surface) including the analyte and reporter antibody may then be subjected to a washing protocol, e.g., as described in Section 8.6, to remove excess reporter antibody.

8.3.2.4 Producing and Detecting Measurable Parameter

Bound reporter antibody may be quantified by detecting a signal facilitated by the reporter antibody. For example, the signal may be radioactivity, color change, luminescence, fluorescence, luminescence, Raman spectra, light scattering approaches, particle/bead aggregation, surface plasmon resonance, Raman spectroscopic effect and the like. The detection may be direct or indirect, by detecting the quantity of antibody coupled to the analyte or by detecting the quantity of unbound antibody.

For approaches requiring further reaction to produce a signal, e.g., conversion of a non-fluorescent product to a fluorescent product, a droplet including the additional required reactants can be brought into contact with antibody-antigen-antibody complex in order to facilitate the further reaction.

Once the reporter antibody has been permitted to bind to the analyte, excess reporter antibody can be washed away using a washing protocol, and droplet operations can be used to bring a droplet including the required reporter reactants into contact with the immobilized antibody. In one embodiment, the reporter antibody is labeled with an enzyme (e.g., horseradish peroxidase (HRP) or alkaline phosphatase (ALP)) capable of catalyzing a reaction which produces a measurable parameter. For example, HRP can be used to catalyze hydrogen peroxide to generate an electrochemical signal which can be detected by measuring the current or voltage. Detection of bound antibody can be achieved by a fluorescence reaction catalyzed by the HRP using Amplex Red and hydrogen peroxide as substrates. Another example employs an alkaline phosphatase mediated conversion of NBT to violet formazan, which can be detected in a droplet colorimetrically. In another approach, a chemiluminescence substrate such as luminol or Ps-atto from Lumigen could be catalyzed by HRP to generate a chemiluminescence signal. Other examples of suitable detection approaches are discussed elsewhere herein (e.g., see 8.3.5).

In one embodiment, the detection step is performed in a droplet on the droplet microactuator in the presence of a sensor in order to enhance or maximize capture of signal from the reaction. In another embodiment, the reaction is performed away from a sensor, and the droplet is transported using droplet operations into the presence of a sensor for detection purposes.

8.3.2.5 Alternative Sandwich Assay Approaches

It will be appreciated that a variety of alternative approaches are possible. For example the steps need not be performed in the order described above, e.g., the reporter antibody may be bound to the analyte prior to or at the same time the analyte is exposed to the immobilized antibody. In another approach, binding of capture antibody, analyte, and reporter antibody can all be performed simultaneously and then presented to a capture site and then washed. In some approaches, such as surface enhanced resonance Raman scattering, washing may not be required.

8.3.3 Competitive Affinity-Based Assay

Figure 8:
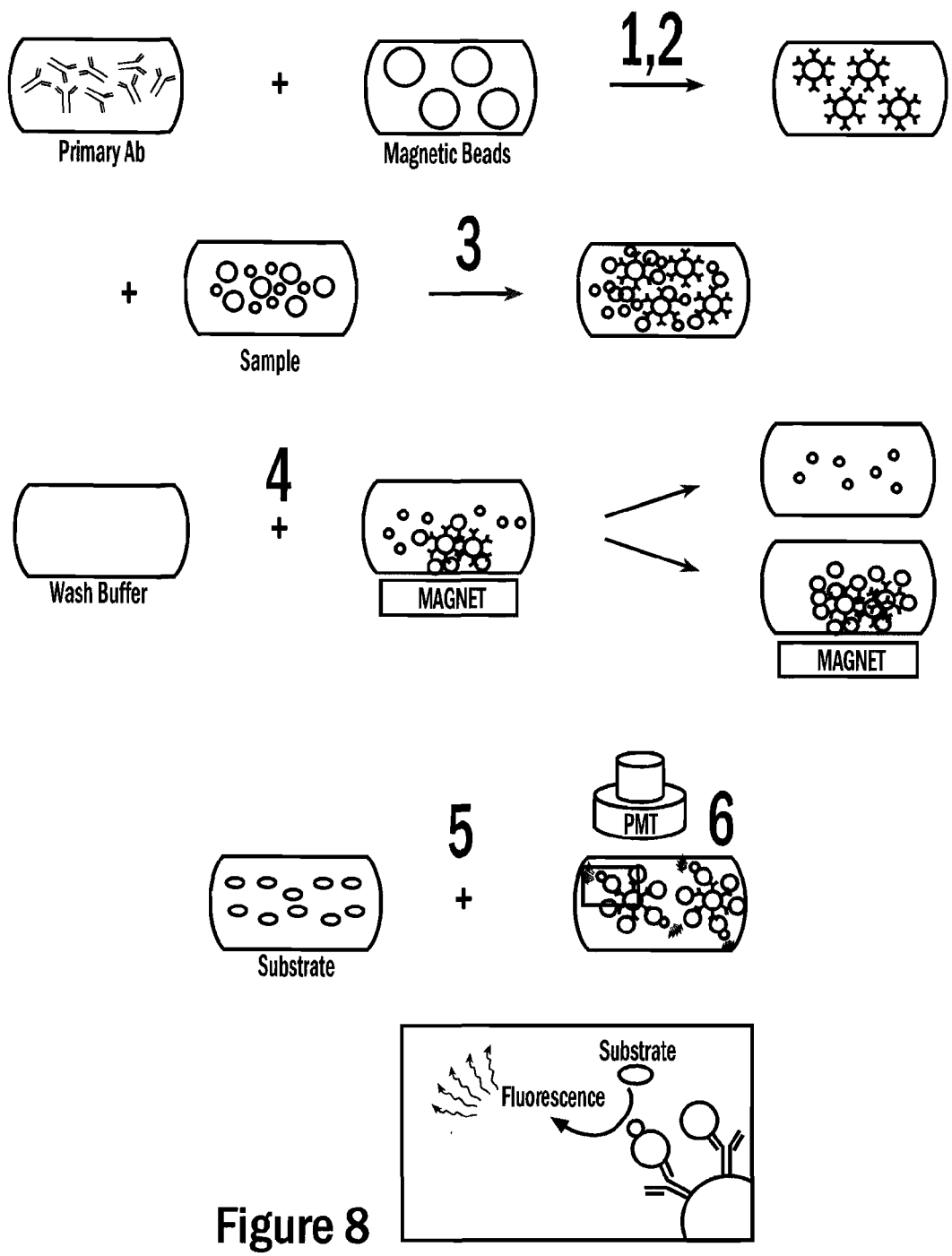
FIG. 8 is an illustration showing steps for conducting a competitive affinity-based assay performed on a droplet microactuator in accordance with an embodiment of the present invention.

In one embodiment, the invention provides a competitive affinity-based assay performed on a droplet microactuator. Analytes for detection by competitive affinity-based assay are typically those that are too small for binding two antibodies as required by a sandwich assay. It will be appreciated that a wide variety of protocols are possible within the scope of the invention for conducting competitive affinity-based assays. The following droplet-based protocol, which is based on the FIG. 8 illustration, is provided for illustration only and is not intended to be limiting of the scope of the invention:

(1) immobilizing on a surface an antibody with specificity for a target analyte;
(2) washing the immobilized antibody, e.g., using a droplet-based washing protocol, to remove excess antibody;
(3) providing a sample droplet potentially including target analyte and including a reporter analyte;
(4) exposing the immobilized antibody to the combined target analyte/reporter analyte droplet so that the reporter analyte competes with any target analyte for binding sites;
(5) washing the substrate to remove unbound analyte and reporter analyte;
(6) optionally, performing additional steps to yield a measurable parameter or signal; and
(7) quantifying bound reporter analyte, wherein the quantity of reporter analyte is inversely proportional to the quantity of target analyte.

Any one or more of the foregoing steps can be performed using droplet manipulation techniques on a droplet microactuator as described herein. Each of the steps is discussed in further detail in the ensuing sections.

8.3.3.1 Immobilizing Antibody

The antibody may be immobilized as described below in Section 8.4.1.1.

8.3.3.2 Competitive Binding

A droplet including the sample potentially including a target analyte is combined with a droplet including the reporter analyte, and the combined droplet is brought into contact with the immobilized antibody. Alternatively, the mixture of target and reporter is accomplished during loading of the droplet microactuator.

The reporter analyte may be made by coupling the reporter nucleic acid to the analyte using any of a variety of conjugation methods. In one embodiment, the analyte portion is modified with a molecule, such as biotin, which generates a secondary capture site for immobilizing a streptavidin sensor DNA complex. The coupling of biotin to the analyte must not unduly interfere with its binding to the capture antibody. The biotinylated material may in some cases compete equally with the analyte from the test sample. Coupling of the biotinylated analyte to a reporter molecule can occur before or after the biotinylated analyte is captured by the immobilized antibody.

For example, in one embodiment, the assay is performed by mixing a droplet with a known quantity of biotinylated analyte with the sample droplet potentially containing an unknown quantity of unmodified analyte. A droplet including the biotinylated analyte is combined with a droplet potentially including the target analyte. The combined droplet is contacted with the immobilized antibody so that the biotinylated analyte and the target analyte (if any) compete for binding to the immobilized antibody. The quantity of biotinylated analyte bound is inversely proportional to the quantity of analyte in the test droplet. The immobilized antibody (e.g., the beads or the surface) may then be subjected to a washing protocol, e.g., as described in Section 8.6, to remove excess reporter analyte.

8.3.3.3 Detecting the Reporter Analyte

After washing, a droplet with a streptavidin-biotin-reporter complex is added to a droplet including the washed beads or otherwise brought into contact with a surface including the immobilized antibody. The streptavidin-biotin-reporter complex binds to any biotinylated analyte that was captured by the antibody on the bead.

8.3.3.4 Alternative Competitive Assay Approaches

The competitive affinity-based assay described here is only one example of a droplet microactuator protocol suitable for execution on the droplet microactuator of the invention. A variety of alternatives are possible within the scope of the invention. For example, the steps are not limited to the order given. The antibody can be bound to the target analyte/reporter analyte before it is immobilized by combining a droplet including the free antibody with one or more droplets including the target analyte/reporter analyte, after which the antibody may be brought into contact with the surface for immobilization. The reporter analyte may be conjugated with the reporter nucleic acid on the droplet microactuator by combining droplets including the two reagents. A droplet including the reporter analyte may be combined with a droplet including the reporter nucleic acid to affect conjugation before or after the reporter analyte is exposed to the captured antibody.

In another embodiment, a competitive assay is performed by mixing a droplet with a known amount of enzyme-labeled analyte with a sample droplet containing the target analyte which is then further mixed with a droplet containing antibodies. Competition ensues for binding sites between the labeled and target analytes. The activity of the enzyme is reduced upon binding of the enzyme-labeled analyte with the antibody and this can be monitored through a number of different types of transduction events, e.g., absorbance, in order quantify the concentration of the target analyte in the sample. For example, a droplet containing Vancomycin labeled with glucose-6-phophate dehydrogenase (G6P-DH) can be mixed with a sample droplet containing unlabelled Vancomycin which can be further mixed with a droplet containing antibodies reactive to Vancomycin, glucose-6-phosphate, and nicotinamide adenine dinucleotide (NAD). The activity of G6P-DH is reduced upon binding to an antibody. G6P-DH converts $NAD^+$ to NADH, resulting in an absorbance change that is measured spectrophotometrically at 340 nm. Once a calibration has been performed within the droplet microactuator, the Vancomycin concentration in each unknown sample can be determined using the stored calibration curve and the measured absorbance obtained in the assay of the sample. Other analytes that can be detected using the same method includes Valproic acid, Tobramycin, Gentamicin, and Caffeine.

8.3.4 Other Affinity-Based Assay Protocols

The competitive affinity-based assay described here is only one example of a droplet microactuator protocol suitable for execution on the droplet microactuator of the invention. A variety of alternatives are possible within the scope of the invention. For example, the droplet microactuator system of the invention enables multiple affinity-based assays to be simultaneously performed on a single sample or a single affinity-based assay to be performed on multiple samples or a combination thereof. Further, affinity-based assays may be performed along with other tests, such as PCR and/or immuno-PCR.

A variety of alternative assay types may be executed using droplet-based protocols in light of the instant specification. Examples include immunoprecipitation assays; immunoradiometric assays; heterogeneous enzyme labeled affinity-based assays in which the quantitation of the antibody bound and unbound fractions requires a physical separation of these two fractions; homogeneous (non-separation) enzyme labeled affinity-based assays which do not require a physical separation of these two fractions because the unbound and antibody bound fractions can be distinguished functionally. For immunoprecipitation assays, droplets including reagents for conducting the immunoprecipitation assays are combined on a droplet microactuator to conduct the immunoprecipitation assay. Immunoprecipitation may be detected using a light scattering detector.

While most of the approaches discussed thus far involve immobilization of the antibody or the analyte, immobilization is not required in all droplet-based immunoassays of the invention. For example, the invention includes a homogenous droplet-based enzyme-multiplied immunoassay in which the labeled antibody includes an enzyme that is inactivated when bound to the primary antibody. Enzymatic activity is approximately proportionate to the analyte concentration. The approach generally includes combining on a droplet microactuator droplets for conducting the droplet-based enzyme-multiplied immunoassay and measuring the resulting enzymatic activity.

In another method, the light scattering properties of the antigen/antibody complex will be altered upon a binding event, and this change can be monitored by detecting light scattering changes in the reaction droplet on the droplet microactuator, such as turbidity measurements, to identify and/or quantitate the capture events. For example, a physiological sample droplet on the droplet microactuator containing immunoglobulins such as IgA, IgG, and IgM (after sample preparation including dilution and addition of polymers) or apolipoproteins such as ApoA1, ApoB (after sample preparation including dilution and addition of polymers or surfactants) can be combined using droplet operations with a droplet containing respective antibodies that, upon occurrence of binding events, results in a change in the turbidity of the combined droplet which can be monitored spectrophotometrically. A few examples of other analytes that can be measured using this technique include $\alpha_1$-antitrypsin (AAT), transferrin, prealbumin, haptoglobin, complement C3, and complement C4.

Another class of immunoassays suitable for use in the present invention include agglutination assays which can also be performed in the droplet format. A droplet containing the analyte is mixed with a droplet containing particles, for example latex particles, with the capture antibody or antigen bound to the particles. If the target analyte is present in the sample, the latex particles start to agglutinate together and it can be quantified by measuring the absorbance.

The system provides multiplexed affinity-based assays. In one embodiment, the system has the ability to detect 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more analytes using immunoassays. In some high throughput settings, the system provides for multiplexed detection of 96, 384, 1536, or higher number of analyses either in serial fashion on in parallel fashion. The analytes may, for example, include analytes from natural or non-natural sources. In another embodiment, the invention has the ability to execute affinity-based assay protocols for detecting one or more analytes from any 2, 3, 4 or 5 the following categories: analytes from bacterial sources, analytes from viral sources, analytes from fungal sources, protein toxin analytes, and small molecule toxin analytes.

The system may be programmed to repeat assays as needed to increase confidence for a single target result. Importantly, the droplet microactuator system can be programmed to effect confirmatory re-testing of positives to reduce the possibility of false positives. The system may also be programmed and configured to permit storage of tested samples on the droplet microactuator for subsequent additional laboratory testing.

An important advantage of the invention is the capability of the droplet microactuator to quickly and accurately produce calibration curves. The droplet microactuator can accurately and reproducibly dispense droplets of a solution of known concentration of control analyte and can dilute such droplets by combining them with buffer droplets to provide a series of control droplets having varied concentrations of control analyte. These control droplets can be taken through the same protocol as sample droplets to produce a calibration curve. The calibration curve can be used to determine quantities of analyte in sample droplets.

8.3.5 Other Detection Approaches for Affinity-Based Assays

A wide variety of detecting approaches are available for use in the droplet-based affinity-based assays of the invention. The selected approach will be capable of directly or indirectly producing a signal in a droplet-based affinity-based assay. The signal may be detectable by a sensor positioned in contact with or in close proximity with the droplet. Examples of signals suitable for use in the affinity-based assays include signals produced from radioisotopic labels, fluorescent labels, luminescent labels, electroluminescent labels microparticles, nanoparticles, enzymatic reactions, aggregation compounds, Raman-active dyes, electroactive labels, and labels affecting conductivity. Examples of suitable radioisotopic labels include $^{57}Co$, $^{3}H$, $^{35}P$, $^{35}S$, and $^{125}I$. In one embodiment, radioisotopic labels are used in a scintillation proximity assay (SPA) on a droplet microactuator. SPA's enable detection of binding events without requiring a washing step. The radiolabel may, for example, be incorporated into a competitive analyte in a competition assay or in a secondary antibody in a sandwich assay. Radiolabels that emit alpha or weak beta particles are preferred. The SPA is conducted in proximity to a fluorophore that emits light upon exposure to a radiolabel. For example, the fluorophore may be provided in a bead, in a surface of the droplet microactuator to which an antigen or primary antibody is bound, or in nanoparticle coupled to an antigen or primary antibody. Examples of suitable luminescent labels include acridinium ester, rhodamine, dioxetanes, acridiniums, phenanthridiniums and various isoluminol derivatives. Examples of suitable fluorescent labels include fluorescein and $Eu^{3+}$. Examples of suitable enzymatic labels include those which produce visible, colored, fluorescent and/or luminescent products from suitable substrates. For example, suitable enzymes may include penicillinase, horseradish peroxidase, β-galactosidase, urease, deaminases and alkaline phosphatase. Examples of suitable nanoparticles include metal nanoparticles. Further information about detection approaches suitable for affinity-based assays of the invention is provided in Section 8.11.

8.3.6 Sample Size and Assay Speed

Implementation on a digital microfluidic platform will dramatically reduce the equipment size and cost, primarily by miniaturizing all liquid handling functions. Assays can, in some embodiments, be performed on less than $100^{th}$ or $1000^{th}$ of the sample and reagent volumes currently used with equal sensitivity and specificity. In one embodiment, the system will typically perform affinity-based assays using samples at droplet volumes of 1 µL or less, or 100 nanoliters or less.

Other advantages include reduced time to results due to faster kinetics in the miniaturized format for the assays and higher throughput due to multiplexing. For example, in one embodiment, the system executes affinity-based assay protocols for detecting 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more analytes in less than about 60, 50, 40, 30, 20, 15, 10, 5 or 2 minutes.

8.3.7 Applications of Droplet-Based, Affinity-Based Assays

As noted above, the affinity-based assays of the invention are useful for detecting a wide variety of molecules. Any molecule which binds with affinity to an affinity molecule, such as an antibody, is a suitable analyte. Analytes may, for example, include biological molecules or synthetic molecules. Biological molecules may, for example, include molecules from plants, animals, microbes, and viruses. Synthetic molecules may, for example, include industrial byproducts, pollutants, and pharmaceuticals. Analytes may include toxins or analytes indicative of the presence of specific biological organisms, e.g., infectious diseases, or toxins that are employed in bioterrorism or biological warfare. Examples of such organisms include anthrax, avian influenza, botulism, hantavirus, legionnaires' disease, pneumonic plague, smallpox, tularemia, and viral hemorrhagic fevers (VHFs). Other examples include analytes associated with monitoring the immunogenicity of vaccines targeting cancer, chronic infectious diseases (e.g., HIV, malaria, hepatitis C, candidemia), immunology (e.g., allergy, autoimmunity), endocrinology (thyroid, non-thyroid), drug testing (e.g., drugs of abuse, therapeutic drugs) and detection of bioterrorism agents (e.g., anthrax, smallpox).

In one embodiment, immunoassay technique is used to test a sample for the presence of a biological organism, such as a bacteria or a virus. In some embodiments, the system can achieve extremely sensitive detections even down to a single cell. Further, some embodiments may include PCR bacterial typing or variance.

The affinity-based assays of the invention are also useful for detecting chemical, biological or explosive threats. For example, antibody to explosives can be used to detect the presence of trace amounts of explosive in a sample. Thus, the invention also provides a method of screening an area for chemical or biological analytes indicative of the presence of biological, chemical, or explosive weapons.

In one embodiment, the invention provides the capability of detecting multiple analytes in a single droplet. One way to achieve this result according to the invention involves the use of different antibodies for different analytes at spatially separated locations on the droplet microactuator. For example, the droplet microactuator may include multiple surfaces, each comprising a specific antibody. A single sample droplet may be manipulated to come into contact with these antibodies all at once, or sequentially, as the droplet is transported across the antibody regions. Affinity-based assay protocols of the invention may be employed to detect the presence of analyte bound to the antibody in any of the various regions. Similarly, multiple analytes can be detected in a single droplet by using different labels to simultaneously detect different analytes in the same spatial area. In another embodiment, the droplet microactuator includes spatially separated beads, each bead or set of beads having a unique antibody or set of antibodies. Sample droplets and/or bead containing droplets may be manipulated using droplet operations in order to contact a sample droplet with each of the beads or sets of beads.

8.4 Immuno PCR

The invention provides a droplet-based immuno PCR (pick) for sensitively detecting analytes that are available only at trace levels. This invention combines the various means of affinity-based assays using a detector antibody on a droplet-based platform and utilizes a nucleic acid strand as a label. This nucleic acid strand is amplified using amplification techniques (e.g., see Section 8.1).

It will be appreciated that an important aspect of the invention involves the ability to conduct droplet operations using each of the required iPCR reagents and/or samples on a droplet microactuator. For example, the invention includes:

(1) a droplet microactuator comprising thereon a droplet comprising any one or more of the reagents and/or samples described herein for conducting iPCR protocols;
(2) a device or system of the invention comprising such droplet microactuator;
(3) a method of conducting droplet operations on or otherwise manipulating a droplet making use of such droplet microactuator or system; and/or
(4) a method of conducting an droplet-based affinity-based assay making use of such droplet microactuator or system.

For example, the droplet operations may include one or more of the following: loading a droplet into the droplet microactuator; dispensing one or more droplets from a source droplet; splitting, separating or dividing a droplet into two or more droplets; transporting a droplet from one location to another in any direction; merging or combining two or more droplets into a single droplet; diluting a droplet; mixing a droplet; agitating a droplet; deforming a droplet; retaining a droplet in position; incubating a droplet; heating a droplet; vaporizing a droplet; cooling a droplet; disposing of a droplet; transporting a droplet out of a droplet microactuator; other droplet operations described herein; and/or any combination of the foregoing. Various other methods, devices, systems, and other aspects of the invention will be apparent from the ensuing discussion.

8.4.1 Sandwich iPCR

In one embodiment, the invention provides a droplet-based sandwich iPCR performed on a droplet microactuator. In general, the sandwich iPCR involves:

(1) immobilizing on a surface an antibody with specificity for a target analyte;
(2) washing the immobilized antibody, e.g., using a droplet-based washing protocol;
(3) exposing the immobilized antibody to a sample droplet potentially including the target analyte;
(4) washing the immobilized antibody, e.g., using a droplet-based washing protocol;
(5) exposing the immobilized antibody (now potentially including the target analyte bound thereto) to a droplet including a second antibody conjugated to a nucleic acid molecule;
(6) washing the immobilized antibody, e.g., using a droplet-based washing protocol;
(7) amplifying the nucleic acid and detecting the amplification (if any) to determine the presence and quantity of captured target analyte.

Any one or more of the foregoing steps can be performed using droplet manipulation techniques on a droplet microactuator as described herein. Each of the steps is discussed in further detail in the ensuing sections.

8.4.1.1 Immobilizing Antibody

A primary antibody is immobilized on a surface. The surface may, for example be a surface of the droplet microactuator, or the surface of beads, such as magnetically responsive beads. Immobilization of the antibody to the surface can be accomplished on the droplet microactuator using droplet-based protocols. For example, reagents for immobilizing an antibody to a surface may be introduced to the droplet microactuator, dispensed as discrete droplets and transported into contact with the surface for deposition. Where the surface in question is the surface of one or more beads, the beads may be introduced to the droplet microactuator, dispensed as droplets in a buffer, transported, and merged with one or more droplets including reagents for immobilizing the droplets on the surface of the beads.

A wide variety of techniques are available for binding antibody to surfaces. For example, the surface may be activated with Protein G to enable the binding of antibody molecules via their Fc domain, leaving the variable region available for target capture. Antibody may be covalently bound to latex surfaces by reaction of activated antibody with 1,3-diaminopropane coupled, polystyrene aldehyde/sulfate latex. Surfactant-free sulfate white polystyrene latex beads may be coated with antibody by incubation with antibody and conjugation buffer (30 mM $Na_2CO_3$, 70 mM $NaHCO_3$, pH 9.5). Biotinylated antibody can be captured on streptavidin coated substrates. Light-directed immobilization can also be performed, e.g., as described elsewhere in the present disclosure.

8.4.1.2 Binding Target Analyte to Immobilized Antibody

A sample droplet is contacted with the immobilized antibody to permit any target analyte present in the sample to bind with the immobilized antibody. This step may be accomplished by transporting a sample droplet into contact with a surface of the droplet microactuator on which the antibody is immobilized. In another embodiment, the step may be accomplished by merging a sample droplet with a droplet including beads on which the antibody has been immobilized. The antibody binds to the analyte from the sample droplet. The immobilized antibody (e.g., the beads or the surface) may be subjected to a washing protocol, e.g., as described in Section 8.6.

8.4.1.3 Binding Antibody-NA to Target Analyte

After washing (e.g., the beads or the surface), a droplet comprising an antibody-NA conjugate having affinity for a different epitope on the analyte may be brought into contact with the washed immobilized antibody potentially having the captured analyte. The antibody-NA conjugate includes a nucleic acid molecule coupled to the antibody. The nucleic acid molecule serves as the nucleic acid template for amplification. The immobilized antibody (e.g., the beads or the surface) are then subjected to a washing protocol, e.g., as described in Section 8.6.

8.4.1.4 Amplifying the Nucleic Acid

The nucleic acid is amplified, e.g, as described in Section 8.1. The quantity of amplified product produced is measured, e.g., using real time fluorescence detection, electrochemical and/or electrochemiluminescent detection. The quantity of PCR product produced correlates with the quantity of bound antibody-DNA, which depends in turn on the quantity of analyte present in the sample droplet.

8.4.1.5 Alternative Approach

In an alternative embodiment, the order of these steps is generally reversed to perform nucleic acid amplification followed by an affinity-based assay that results in an optical or electrical signal. In this sequence, an immunoassay would be performed to monitor nucleic acid amplification.

8.4.2 Competitive iPCR

In one embodiment, the invention provides a competitive iPCR performed on a droplet microactuator. Analytes for detection by competitive iPCR are typically those that are too small for binding two antibodies as required by a sandwich assay. In general, the competitive iPCR involves:

(1) immobilizing on a surface an antibody with specificity for a target analyte;
(2) combining a sample droplet potentially including target analyte with a droplet including a reporter analyte;
(3) exposing the immobilized antibody to the combined target analyte/reporter analyte droplet so that the reporter analyte competes with any target analyte for binding sites;
(4) washing the substrate to remove unbound analyte;
(5) coupling the bound reporter analyte to a reporter nucleic acid; and
(6) amplifying the reporter nucleic acid and monitoring the progress of the amplification to determine the quantity of unbound reporter analyte, which for the bound reporter analyte is inversely proportional to the quantity of target analyte in the sample.

Any one or more of the foregoing steps can be performed using droplet manipulation techniques on a droplet microactuator as described herein. Each of the steps is discussed in further detail in the ensuing sections.

8.4.2.1 Immobilizing Antibody

The antibody may be immobilized as described above in Section 8.4.1.1.

8.4.2.2 Competitive Binding

A droplet including the sample potentially including a target analyte is combined with a droplet including the reporter analyte, and the combined droplet is brought into contact with the immobilized antibody.

The reporter analyte may be made by coupling the reporter nucleic acid to the analyte using any of a variety of conjugation methods. In one embodiment, the analyte portion is modified with a molecule, such as biotin, which generates a secondary capture site for immobilizing a streptavidin-DNA complex. The coupling of biotin to the analyte must not unduly interfere with its binding to the primary capture antibody. The biotinylated material may in some cases compete equally with the analyte from the sample. Coupling of the biotinylated analyte to the reporter nucleic acid can occur before or after the biotinylated analyte is captured by the immobilized antibody.

For example, in one embodiment, the assay is performed by mixing a droplet with a known quantity of biotinylated analyte with the sample droplet potentially containing an unknown quantity of unmodified analyte. A droplet including the biotinylated analyte is combined with a droplet potentially including the target analyte. The combined droplet is contacted with the immobilized antibody so that the biotinylated analyte and the target analyte (if any) compete for binding to the immobilized antibody. The quantity of biotinylated analyte bound is inversely proportional to the quantity of analyte in the sample droplet.

8.4.2.3 Coupling the Nucleic Acid Reporter

After washing, a droplet with a streptavidin-biotin-reporter nucleic acid complex is added to a droplet including the washed beads or surface. The streptavidin-biotin-reporter nucleic acid complex binds to any biotinylated analyte that was captured by the antibody on the bead.

8.4.2.4 Amplifying the Nucleic Acid

After washing, the quantity of a streptavidin-biotin-reporter nucleic acid complex immobilized is determined by amplification of the reporter nucleic acid. The amplification signal is an inverse measure of the quantity of analyte in the original sample. Amplification may proceed as described in Section 8.1. The presence and quantity of amplified product produced is measured, e.g., using real time fluorescence detection. The quantity of reporter analyte that was displaced is proportional to the quantity of target analyte in the sample.

8.4.2.5 Alternative Approaches

The steps are not limited to the order given. For example, the antibody can be bound to the target analyte/reporter analyte before it is immobilized by combining a droplet including the free antibody with one or more droplets including the target analyte/reporter analyte, after which the antibody may be brought into contact with the surface for immobilization. The reporter analyte may be conjugated with the reporter nucleic acid on the droplet microactuator by combining droplets including the two reagents. A droplet including the reporter analyte may be combined with a droplet including the reporter nucleic acid to affect conjugation before or after the reporter analyte is exposed to the captured antibody. A variety of alternatives is possible within the scope of the invention.

8.4.3 Samples and Sample Preparation

A wide variety of analytes may be detected using droplet-based iPCR protocols of the invention. A single sample may be analyzed for one or more target analytes. Analytes may, for example, be biological analytes or synthetic analytes. For example, in one embodiment, the analytes are selected from following categories: analytes from bacterial sources, analytes from viral sources, analytes from spore sources, protein toxin analytes, and small molecule toxin analytes. In one embodiment, the target analytes include toxins or analytes indicative of the presence of specific biological organisms, e.g., infectious diseases, or toxins that are employed in bioterrorism or biological warfare. Examples of such organisms include anthrax, avian influenza, botulism, hantavirus, legionnaires' disease, pneumonic plague, smallpox, tularemia, and viral hemorrhagic fevers (VHFs).

8.4.4 Immuno-PCR Protocols

The system of the invention enables multiple immuno-PCR tests to be simultaneously performed on a single sample. Further, immuno-PCR tests may be performed along with other tests, such as PCR and/or affinity-based assays.

The system provides multiplexed detection. In one embodiment, the system has the ability to detect 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more analytes. The analytes may, for example, include analytes from natural or non-natural sources. In another embodiment, the invention has the ability to detect one or more analytes from any 2, 3, 4 or 5 the following categories: analytes from bacterial sources, analytes from viral sources, analytes from spore sources, protein toxin analytes, and small molecule toxin analytes.

The system may be programmed to implement additional tests as needed to increase confidence for a single target result. Importantly, the droplet microactuator system can be programmed to effect confirmatory re-testing of positives to reduce the possibility of false positives. The system may also be programmed and configured to permit storage of tested samples on the droplet microactuator for subsequent additional laboratory testing.

In operation, the system performs analysis and provides results extremely quickly. For example, in one embodiment, the system has the ability to detect 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more analytes in less than about 60, 50, 40, 30, 20, 15 or 10 minutes. In another embodiment, the system has the ability to detect 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more analytes from any 2, 3, 4 or 5 the following categories: analytes from bacterial sources, analytes from viral sources, analytes from spore sources, protein toxin analytes, and small molecule toxin analytes, and all tests are completed in less than about 60, 50, 40, 30, 20, 15 or 10 minutes.

8.4.5 Applications

The iPCR assays provided by the invention are useful for detecting a wide variety of molecules present in extremely small quantities. Among other things, the system is useful for surveillance for a chemical, biological or explosive threat. For example, antibody to explosives can be used to detect the presence of trace amounts of explosive in a sample. Thus, the invention also provides a method of screening an area for chemical or biological analytes indicative of the presence of biological, chemical, or explosive weapons.

In one embodiment, iPCR technique is used to test a sample for the presence of a biological organism, such as a bacteria or a virus. In some embodiments, the system can achieve even single-organism detection. Further, some embodiments may include PCR bacterial typing or variance.

8.5 Analysis of Biological Fluids

The invention provides methods, devices and systems for analysis of blood, various components of blood, and other biological fluids. Illustrative designs for a biological fluid analyzer are shown in FIGS. 9 and 17.

Figure 9:
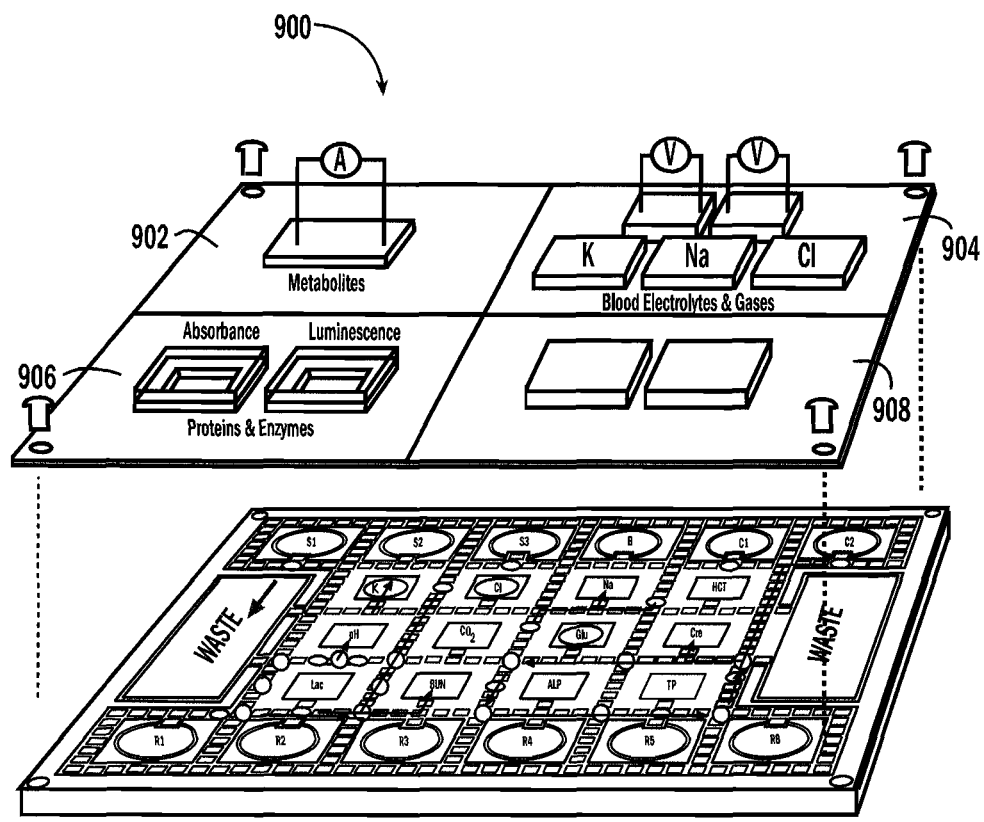
FIG. 9 is a perspective view of a biological fluid analyzer in accordance with an embodiment of the present invention.

FIG. 9 illustrates one embodiment of a biological fluid analyzer 900. In this embodiment, various modules may be provided for conducting biological fluid analysis, such as, for example, detection of metabolites (e.g., glucose, lactate, blood urea nitrogen, and creatinine), electrolytes (e.g., $K^+$, $Cl^-$, and $Na^+$), proteins, and enzymes. These various modules may include amperometric module 902, potentiometric module 904, optical module 906, and conductometric module 908.

Figure 17:
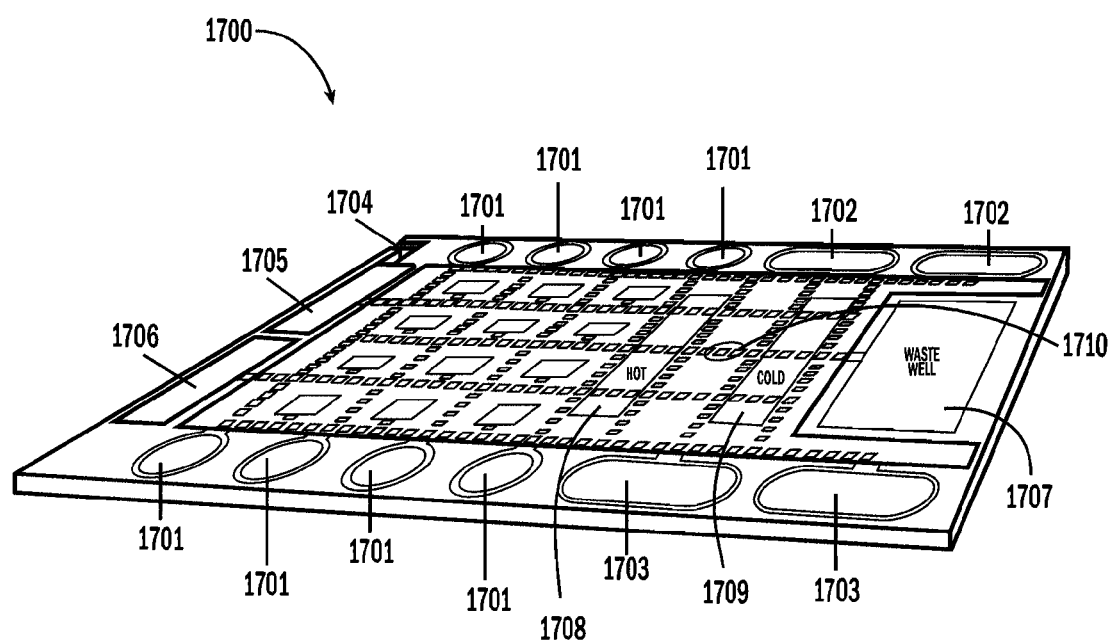
FIG. 17 is a perspective view of a biological fluid analyzer in accordance with an embodiment of the present invention.

Another embodiment of a biological fluid analyzer 1700 is illustrated in FIG. 17. In this embodiment, multiple fluid ports or reservoirs may be provided such as antibody reservoirs 1701 (such as for bacteria antibodies, spore antibodies, bacteria AB-DNA, spore AB-DNA, protein toxin antibodies, small molecule antibodies, protein AB-DNA, and small molecule SB-A DNA), PCR primer reservoirs 1702, and PCR reagents reservoirs 1703. Sample port 1704 may also be provided, as well as sample reservoir 1705, wash solution area 1706, and waste reservoir 1707. Other areas that may be provided include hot temperature area 1708, cold temperature area 1709, and detector area 1710.

It will be appreciated that an important aspect of the invention involves the ability to conduct droplet operations using each of the required biological fluid analysis samples and reagents on a droplet microactuator. For example, the invention includes:
(1) a droplet microactuator comprising thereon a droplet comprising any one or more of the reagents and/or samples described herein for conducting such biological fluid analysis;
(2) a device or system of the invention comprising such droplet microactuator;
(3) a method of conducting droplet operations on or otherwise manipulating a droplet making use of such droplet microactuator or system; and/or
(4) a method of conducting an droplet-based affinity-based assay making use of such droplet microactuator or system.

For example, the droplet operations may include one or more of the following: loading a droplet into the droplet microactuator; dispensing one or more droplets from a source droplet; splitting, separating or dividing a droplet into two or more droplets; transporting a droplet from one location to another in any direction; merging or combining two or more droplets into a single droplet; diluting a droplet; mixing a droplet; agitating a droplet; deforming a droplet; retaining a droplet in position; incubating a droplet; heating a droplet; vaporizing a droplet; cooling a droplet; disposing of a droplet; transporting a droplet out of a droplet microactuator; other droplet operations described herein; and/or any combination of the foregoing. Various other methods, devices, systems, and other aspects of the invention will be apparent from the ensuing discussion.

8.5.1 Sample and Sample Preparation

Examples of suitable samples for use with the droplet microactuator of the invention include whole blood, serum, and plasma, and various components thereof. Venous, arterial, or capillary blood can be used. Examples of other samples usefully analyzed according to the present invention include cerebrospinal fluid (CSF), urine, saliva, sweat, tears, amniotic fluid, pleural fluid, milk, cystic fluid, synovial fluid, stool, and semen.

Figure 10:
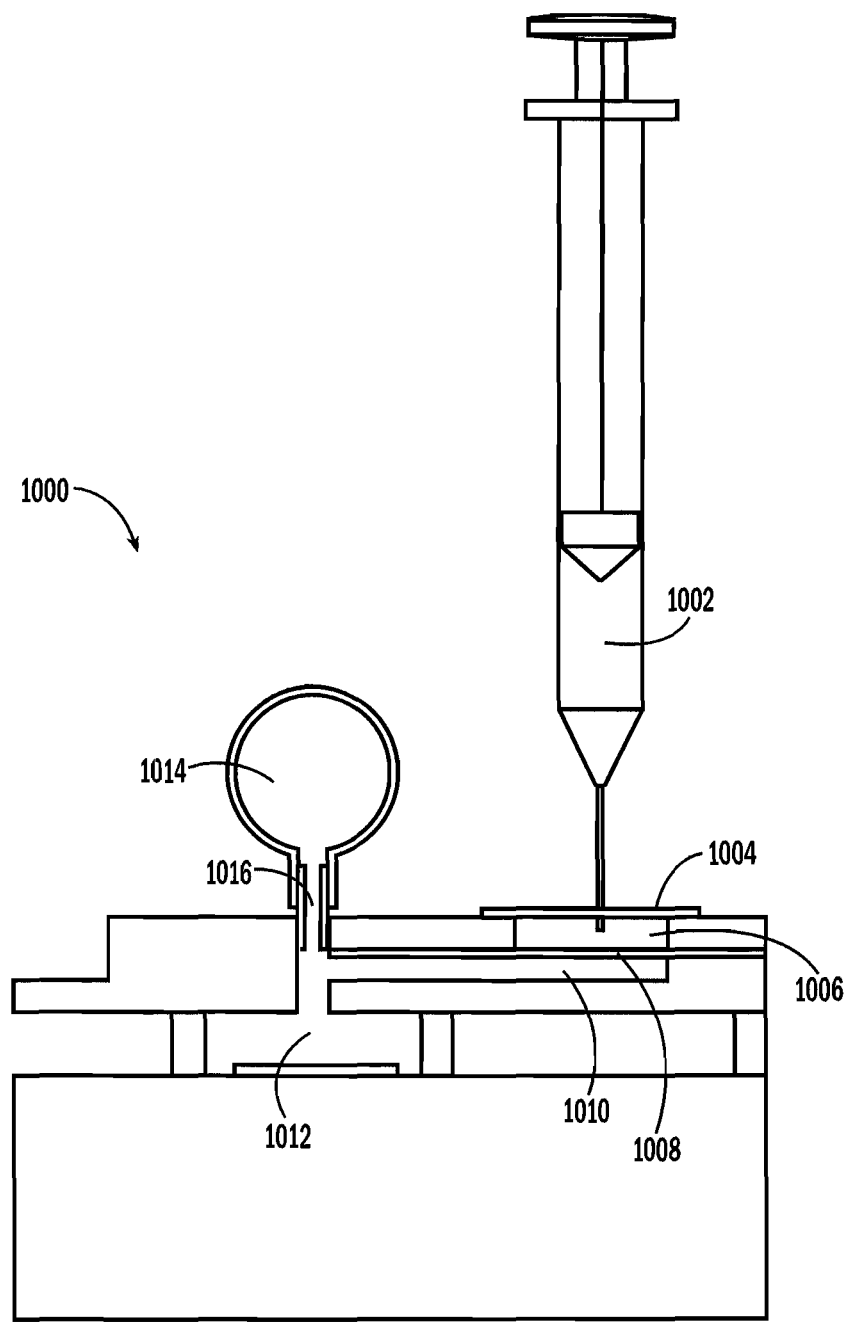
FIG. 10 is a side profile view of a droplet microactuator loading structure in accordance with an embodiment of the present invention.

Serum and/or plasma may be extracted from whole blood on the droplet microactuator and/or prior to introduction into the droplet microactuator. An example of a loading structure 1000 provided for this purpose is provided in FIG. 10. In this embodiment, fluid is flowed from a reservoir 1002 through a sealing means 1004 into a loading chamber 1006 where it comes into contact with a membrane 1008. Permeate passes into a permeate flow channel 1010 through which it flows into droplet microactuator reservoir 1012, assisted by pressure source 1014 which applies pressure via channel 1016.

The small size of the device dramatically reduces the volume of sample required for routine testing, which is an important concern in many settings. For example, typical sample sizes will have a volume which is in one embodiment from about 1 nL to about 100mL, or about 10 nL to about 10 mL, or about 1 μL to about 10 μL.

8.5.2 Analytes

The invention provides a versatile droplet microactuator system capable of performing an array of tests on a single sub-microliter droplet of blood or any physiological sample of about ~0.5 μL. Examples of suitable tests include metabolites (e.g., glucose, creatinine, lactate, blood urea nitrogen), electrolytes/elements (e.g., K+, Na+, Cl−, P, Mg, Li, Ca, Fe), gases (e.g., pH, $pCO_2$, $NH_3$), enzymes (alkaline phosphatase (ALP), aspartate aminotransferase (AST), alanine aminotransferase (ALT), lactate dehydrogenase (LDH), Lipase, Creatine Kinase, Creatine Kinase MB), proteins (albumin, c-reactive protein (CRP), urine microalbumin, urine protein, cerebrospinal fluid protein, serum total protein), and hematocrit. Other analytes include glycated hemoglobin (Alc), hemoglobin, uric acid, triglycerides, cholesterol, high density lipoprotein (HDL) and low density lipoprotein (LDL).

8.5.2.1 Metabolites

The invention is useful in conducting a variety of enzyme-coupled assays, such as for glucose, blood urea nitrogen, creatinine, and lactate based on electrochemical or optical detection. In some embodiments, glucose, lactate, and creatinine are measured through the amperometric detection of $H_2O_2$ in an enzyme-coupled assay performed on the droplet microactuator.

In some embodiments, the invention includes an electrochemistry module with electrodes for amperometric and/or potentiometric detection of metabolites (e.g., glucose, lactate, blood urea nitrogen, creatinine).

8.5.2.2 Electrolytes

For quantifying various ions (e.g., ammonia, bromide, cadmium, calcium, chloride, copper, cyanide, fluoride, fluorborate, iodide, lead, nitrate, perchlorate, potassium, silver/sulfide, magnesium, iron, lithium, phosphorus, sodium, surfactant, thiocyanate) in a sample, such as a processed biological sample, the droplet microactuator may be modified to include an ion-selective electrode (ISE). A sample droplet may be transported into contact with the ISE for detection of the desired ion. Further, prior to detection, standard droplets may be brought into contact with the ISE for the purpose of calibration. In some embodiments, the invention includes an electrochemistry module with electrodes for amperometric, potentiometric, and/or conductometric detection of electrolytes (e.g., $K^+$, $Cl^-$, $Na^+$).

ISEs can be included in the droplet microactuator for detecting electrolytes. ISEs can, for example, be included as components of a top and/or bottom substrate and/or as components exposed to a space between a top and/or bottom substrate or associated with a single substrate droplet microactuator. They can be integrated with transport electrodes. The ISEs are generally arranged so that droplet operations can be employed to bring a droplet on the droplet microactuator into contact with an ISE. Various techniques can be used to make ion selective electrodes on the droplet microactuator. Examples include screen printing, as well as photolithography, etching, and lift-off.

As a specific non-limiting example, Ag/AgCl can be screen printed to provide working and reference electrodes with a KCl salt bridge. Examples of suitable ionophores in PVC for the fabrication of ion-selective membranes include methyl monensin for Na+, valinomycin for K+, quaternary ammonium chloride for Cl−, and tridodecyl amine for pH. The ion-selective membranes can be made by micro dispensing and/or spray-coating (e.g., thermal/ultrasonic printing).

Electrolytes can be detected in any biological sample. Specific non-limiting examples include whole blood, plasma and serum, as well as the examples provided elsewhere in this disclosure.

8.5.2.3 Gases

For quantifying the presence of gasses (e.g., $pCO_2$, $pO_2$) or pH, various specialized electrodes may be used. As a non-limiting example, a carbon dioxide microprobe may be incorporated into a droplet microactuator of the invention for detection and/or quantification of carbon dioxide. The microprobe may be arranged so that droplet operations can be employed to bring a droplet on the droplet microactuator into contact with the microprobe. Further, prior to detection, standard droplets may be brought into contact with the carbon dioxide microprobe, using droplet operations, for the purpose of calibration. Corresponding approaches are suitable for detecting oxygen and/or determining pH. In some embodiments, the droplet microactuator may include electrodes for amperometric, potentiometric, and/or conductometric detection of blood gases (e.g., $pCO_2$, $pO_2$, pH).

As a specific non-limiting example, a Severinghaus-type $CO_2$ sensor can be made with the pH electrode made of gold-quinhydrone electrode immersed with the internal solid electrolyte made of $NaHCO_3$, NaCl, and a sucrose binder. A gas permeable membrane of polydimethylsiloxane can be deposited thereon. Digital conditioning electronics (e.g., high input impedance amplifiers) can be used to interface with the potentiometric electrodes.

Gasses can be detected in any droplet on the droplet microactuator. Specific non-limiting examples include droplets including whole blood, plasma, and/or serum, as well as the biological samples described elsewhere in this disclosure.

8.5.2.4 Enzyme

In some embodiments, the invention includes chemiluminescence assays for detection of enzymes, such as liver enzymes. Using a series of droplet-based multiple enzymatic steps, the ALT and AST assays can be reduced to a final step that produces hydrogen peroxide which can be measured quantitatively by absorbance, luminescence, fluorescence, or electrochemically.

8.5.2.5 Serum Protein

A colorimetric assay may be utilized for detection of total protein in a sample. Examples of suitable colorimetric methods include: the Biuret method, the Lowry method, the bicinchoninic acid (BCA) assay, and Bradford assay. The Biuret method generally involves contacting a sample droplet with a droplet comprising cupric ions. The cupric ions form a colored complex with proteins. The Lowry reaction approach is based on the amplification of the biuret reaction by combining with a Folin reagent droplet. A variation of the Lowry assay uses a Bicinchoninic acid (BCA) droplet to permit detection of the cuprous ions generated from cupric ions by reaction with protein in a droplet under alkaline conditions. The Bradford assay approach involves combining the sample with a droplet comprising Coomassie Blue dye to form a colored complex. In each case, an LED/photodiode setup, e.g., as shown in FIG. 21A, can be used for monitoring the absorbance. Total protein can be detected in any sample droplet using techniques described herein, including optical sensing methods based on fluorescence and/or chemiluminescence, as well as using the affinity-based assay techniques disclosed herein. Specific non-limiting examples of useful samples for determining total proteins include biological samples, such as whole blood, plasma and serum, as well as the samples described elsewhere in this disclosure.

8.5.2.6 Hematocrit

Red blood cells can be quantified in a sample droplet using a variety of techniques. For example, the hemoglobin content can be calculated by measuring absorbance at 805 nm. Oxyhemoglobin can then be calculated by measuring the absorbance at 650 nm. Results may be obtained by comparing the absorbance measurements for samples to the absorbance measurements for a series of known standards.

In some embodiments, the invention includes an electrochemistry module with electrodes for amperometric, potentiometric, and/or conductometric detection of hematocrit. The droplet microactuator may include a conductometric cell with a pair of electrodes for AC conductometric measurement of hematocrit. For a two-substrate droplet microactuator, the electrodes may be located on one or both substrates. The electrodes are arranged so that arranged so that droplet operations can be employed to bring a droplet on the droplet microactuator into contact with the electrodes.

8.5.3 Multi-Analyte Analyzer

Examples of suitable analytes are glucose, creatinine, lactate, BUN, $K^+$, $Na^+$, $Cl^-$, pH, $pCO_2$, ALP, total protein, and hematocrit. In one embodiment, 2, 3, 4, 5, 6, 7, 8, 9, 10, 11, 12 or more analytes are analyzed on a single droplet microactuator. Preferably, these analytes are selected from glucose, creatinine, lactate, BUN, $K^+$, $Na^+$, $Cl^-$, pH, $pCO_2$, ALP, total protein, and hematocrit. In one embodiment, glucose, creatinine, lactate, BUN, $K^+$, $Na^+$, $Cl^-$, pH, $pCO_2$, ALP, total protein, and hematocrit are analyzed on a single droplet microactuator. Other examples of suitable analytes include calcium, bilirubin, albumin, clotting time, ALT, and AST.

In some embodiments, assays 2, 3, 4, 5, 6, 7, 8, 9, 10, 11, 12 or more analytes are processed in parallel on a droplet microactuator system of the invention, i.e., one or more processing and/or detecting steps for such analyte are accomplished simultaneously with one or more processing and/or detecting steps for another analyte on a single droplet microactuator. A droplet microactuator system may execute 2, 3, 4, 5, 6, 7, 8, 9, 10, 11, 12 or more colorimetric assays for detection of the same or different analyte types in parallel. The droplet microactuator system may execute 2, 3, 4, 5, 6, 7, 8, 9, 10, 11, 12 or more chemiluminescence assays for detection of the same or different analyte types in parallel. The droplet microactuator may execute 2, 3, 4, 5, 6, 7, 8, 9, 10, 11, 12 or more amperometric assays for detection of the same or different analyte types in parallel. The droplet microactuator may execute 2, 3, 4, 5, 6, 7, 8, 9, 10, 11, 12 or more potentiometric assays for detection of the same or different analyte types in parallel. The droplet microactuator may execute 2, 3, 4, 5, 6, 7, 8, 9, 10, 11, 12 or more fluorescence assays for detection of the same or different analyte types in parallel. The droplet microactuator may include 2, 3, 4, 5, 6, 7, 8, 9, 10, 11, 12 or more conductometric assays for detection of the same or different analyte types run in parallel. The droplet microactuator will include droplets or reservoirs including reagents for executing each of the protocols. The droplet microactuator device and/or system will include detection components as needed for executing detection steps of the protocols.

Moreover, the droplet microactuator may include 2, 3, 4, 5, 6, 7, 8, 9, 10, 11, 12 or more analytes that are processed in parallel, and the system may execute 1, 2, 3, 4, 5, 6 or more assay protocols on these analytes. The droplet microactuator may include 2, 3, 4, 5, 6, 7, 8, 9, 10, 11, 12 or more analytes that are processed in parallel, and execute 1, 2, 3, 4, 5, 6 or more assay protocols on these analytes, where the assays are selected from colorimetric assays, chemiluminescence assays, fluorescence assays, amperometric assays, potentiometric assays and conductometric assays. The droplet microactuator will include droplets or reservoirs including reagents for executing each of the protocols. The droplet microactuator device and/or system will include detection components as needed for executing detection steps of the protocols.

Furthermore, various protocols for nucleic acid amplification, nucleic acid sequencing, affinity-based assays, cell handling, bead handling and washing, and analyte detection protocols may also be readily integrated into a single droplet microactuator system. In one embodiment, a single droplet microactuator includes reagents and detection components for conducting nucleic acid amplification and nucleic acid sequencing. In another embodiment, a single droplet microactuator includes reagents and detection components to conduct nucleic acid amplification for detection of a blood-borne pathogen and reagents and detection components for conducting one or more other assays from those assay types and/or for analyte types as described herein. In another embodiment, a droplet microactuator includes components for manipulating cells along with components and reagents for conducting affinity-based assays.

In short, the invention enables a droplet-microactuator system that not only performs the routine operations of a central lab-based chemistry analyzer at higher throughput with dramatically lower sample volumes, but also offers better functionality by integrating hematology, pathology, molecular diagnostics, cytology, microbiology, and serology onto the same platform.

In one embodiment, the invention provides a droplet manipulation module integrated with an optical detection module and an electrochemical detection module for analyzing blood gases, electrolytes, enzymes, proteins, and metabolites.

One embodiment of the invention employs a modular design to partition independently optimized fabrication processes. For example, all the electrochemical components can be fabricated on a substrate, all the microfluidic electrodes can be fabricated on another substrate, and all the electronics can be fabricated on yet another substrate. A disposable sandwich droplet microactuator can be formed between the electrochemical module and the droplet manipulation module which can be coupled to a reusable electronics module for data acquisition and analysis. Optical detection modules can be constructed in the analyzer.

8.5.4 Biological Fluid Analysis Detection

The biological fluid analyses described herein make use of a variety of detection approaches, e.g., as described in Sections 8.1, 8.2, 8.3, 8.4, 8.5, and 8.11.

8.6 Surfaces and Surface Washing Protocols

Various protocols of the invention require surfaces for immobilization of reactants. For example, surfaces may be used to capture or immobilize target components of a droplet, such as cells, other beads, microparticles, nanoparticles, antibodies, proteins, peptides, nucleic acids, small molecules and/or other chemical components. Surfaces used for such purposes may, for example, include surfaces of beads, microparticles, nanoparticles, membranes, physical objects, and/or droplet microactuator surfaces. Various protocols require washing step in which unbound materials are removed from one or more surfaces.

A sample droplet including one or more target components for capture may, using droplet operations, be contacted with a surface having affinity for such targets. Washing protocols of the invention may be used to remove from the surface unbound components of the sample droplet. For example, a droplet protocol may be used to bring one or more droplets including one or more target components into contact with one or more surfaces so that the one or more target components may be immobilized or captured on the one or more surfaces. A washing protocol may be executed to remove unbound substances from the one or more surfaces. Similarly, a droplet protocol may be used to bring one or more droplets including one or more target components into contact with one or more beads so that the one or more target components may be immobilized or captured on the one or more beads. A washing protocol may be executed to separate unbound substances from the one or more beads.

Washing generally involves bringing one or more washing droplets into contact with the immobilized surface. Washing may involve agitation of the droplets while in contact with the surface. Washing droplets may, for example, include water, deionized water, saline solutions, acidic solutions, basic solutions, detergent solutions and/or buffers.

Washing protocols of the invention result in highly efficient removal of unbound substances from the surface. In one embodiment, the invention provides method of providing a droplet in contact with a surface with a reduced concentration of a substance. This method may generally include providing a surface in contact with a droplet comprising a starting concentration of the substance and having a starting volume; conducting one or more droplet operations to merge a wash droplet with the droplet to yield a combined droplet; and conducting one or more droplet operations to divide the combined droplet to yield a set of droplets including: (i) a droplet in contact with the surface having a decreased concentration and decreased quantity of the substance relative to the starting concentration; and (ii) a droplet which is separated from the surface.

The method of the invention may yield a droplet in contact with the surface having a decreased quantity or substantially decreased quantity of the substance relative to the starting concentration. The resulting droplet may in some embodiments have a volume which is approximately the same as the starting volume. In some embodiments, the washing steps may be repeated until a predetermined maximum quantity of the one or more components is met or exceeded in the resulting droplet. The predetermined amount may represent a substantial reduction relative to the starting concentration. In some cases, the resulting droplet may be substantially free of the components. For example, in some embodiments, the reduction in amount exceeds 99, 99.9, 99.99, 99.999, 99.9999, 99.99999, 99.999999 percent on a molar basis.

The method of the invention may yield a droplet in contact with the surface having a decreased concentration or substantially decreased concentration of the substance relative to the starting concentration. The resulting droplet may in some embodiments have a volume which is approximately the same as the starting volume. In some embodiments, the washing steps may be repeated until a predetermined maximum concentration of the one or more components is met or exceeded in the resulting droplet. The predetermined concentration limit may represent a substantial reduction relative to the starting concentration. In some cases, the resulting droplet may be substantially free of the components. For example, in some embodiments, the reduction in concentration exceeds 99, 99.9, 99.99, 99.999, 99.9999, 99.99999, 99.999999 percent.

8.6.1 Washing Beads

For protocols making use of beads, droplet with beads can be combined using droplet operations with one or more wash droplets. Then, while retaining the beads (e.g., physically or magnetically), the merged droplet may be divided using droplet operations it into two or more droplets: one or more droplets with beads and one or more droplets without a substantial amount of beads. In one embodiment, the merged droplet is divided using droplet operations into one droplet with beads and one droplet without a substantial amount of beads.

Generally, each execution of a washing protocol results in retention of sufficient beads for conducting the intended assay without unduly detrimental effects on the results of the assay. In certain embodiments, each division of the merged droplet results in retention of more than 90, 95, 97, 98, 99, 99.1, 99.2, 99.3, 99.4, 99.5, 99.6, 99.7, 99.8, 99, 99.9, 99.99, 99.999, 99.9999, 99.99999, or 99.999999 percent of beads. In other embodiments, each execution of a washing protocol to achieve a predetermined reduction in the concentration and/or amount of removed substance results in retention of more than 99, 99.1, 99.2, 99.3, 99.4, 99.5, 99.6, 99.7, 99.8, 99, 99.9, 99.99, 99.999, 99.9999, 99.99999, or 99.999999 percent of beads. In still other embodiments, the amount of retained beads is calculated and the results are adjusted accordingly.

In some embodiments, beads can be washed in reservoirs in which the bead-containing droplet and wash droplets are combined, beads are retained (for example by a magnet, by physical structures, electrostatic forces), and droplets lacking beads are dispensed from the reservoir using droplet operations. For example, beads can be washed by dilute-and-dispense strategy whereby a wash buffer is added to the reservoir to dilute the contents, magnetically responsive beads are localized within the reservoir with a magnet and most of the solution is dispensed from the reservoir, and this cycle is repeated till acceptable levels of washing are achieved.

8.6.1.1 Washing Magnetically Responsive Beads

Figure 11:
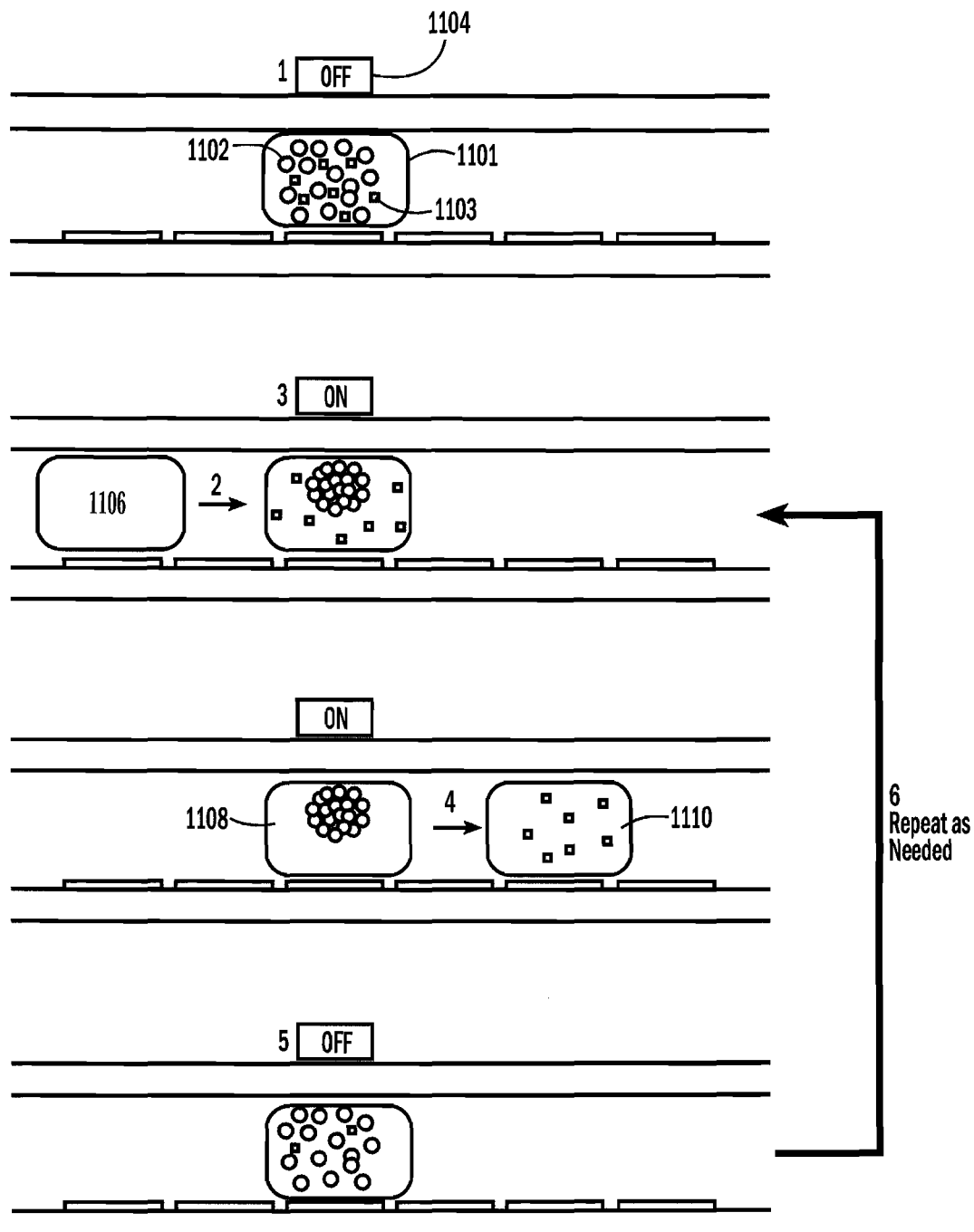
FIGS. 11-13 are illustrations showing steps for immobilizing and freeing magnetically responsive beads using a magnetic field in accordance with various embodiments of the present invention.

A non-limiting example, illustrated in FIG. 11, involves immobilizing magnetically responsive beads using a magnetic field. Immobilized magnetically responsive beads may be freed by reduction or elimination of the magnetic field. Washing magnetically responsive beads may generally include the following steps:

(1) using droplet operations to position a droplet 1101 comprising magnetically responsive beads 1102 and unbound substances 1103 in proximity with a magnet 1104;
(2) using droplet operations to combine a wash droplet 1106 with the droplet 1101 comprising the magnetically responsive beads 1102;
(3) immobilizing the beads 1102 by application of a magnetic field;
(4) using droplet operations to remove some or all of the droplet surrounding the beads to yield a droplet 1108 comprising the beads with a reduced concentration of unbound target substance and a droplet 1110 comprising unbound target substance;
(5) releasing the beads 1102 by removing the magnetic field;
(6) repeating steps (2) to (3) or (2) to (4) until a predetermined degree of purification is achieved.

In this manner, unbound substances, such as contaminants, byproducts or excess reagents, can be separated from the beads. Each cycle produces a droplet including the beads but with a decreased level of the unwanted substances. Step (5) is not required in each washing cycle; however, it may be useful to enhance washing by freeing contaminants which may be trapped in the immobilized beads. Steps may be performed in a different order, e.g., steps (2) and (3) may be reversed. Steps in the washing protocol may be accomplished on a droplet microactuator using droplet operations as described herein.

Figure 12:
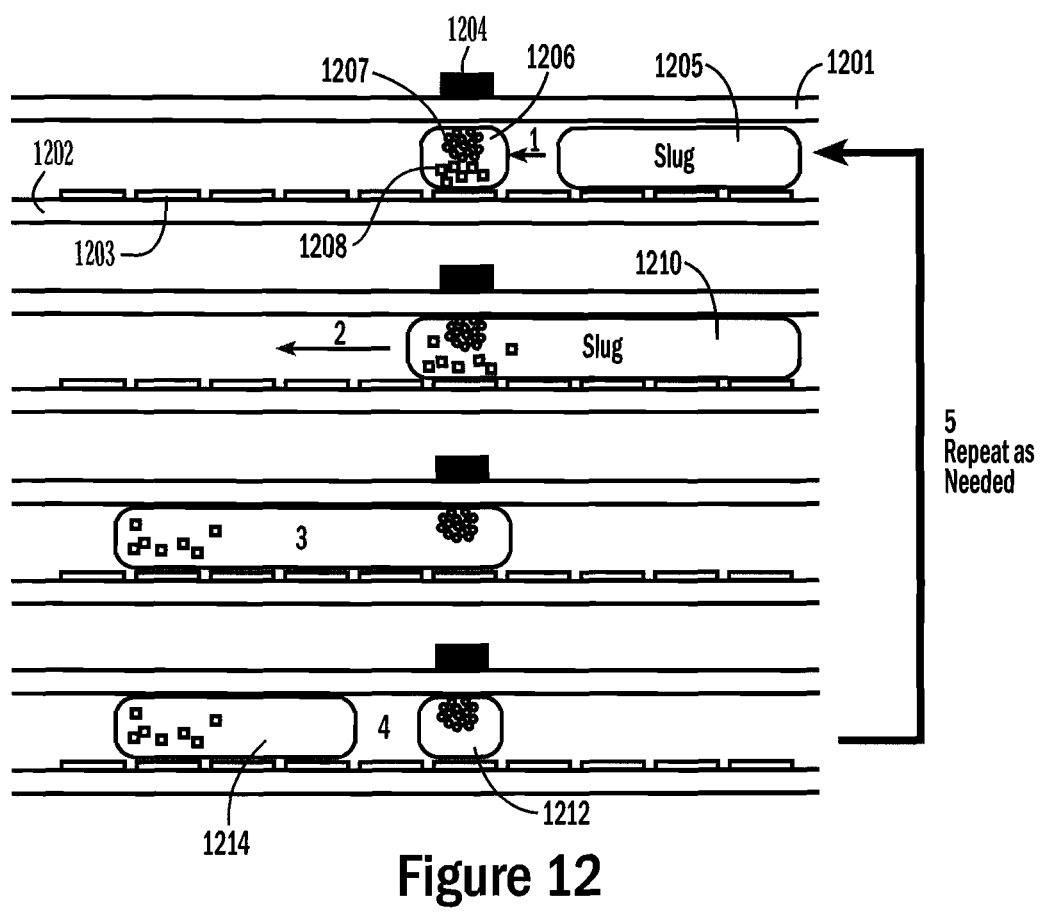

Another embodiment is illustrated in FIG. 12 and may comprise a top plate 1201, bottom plate 1202, electrodes 1203, and a magnet 1204. The embodiment steps generally may include:

(1) using droplet operations to combine a slug 1205 with a droplet 1206 comprising magnetically responsive beads 1207 and unbound material 1208 in proximity with magnet 1204;
(2,3) with the beads 1207 immobilized, using droplet operations to transport the resulting combined slug 1210 across the beads 1207 to separate unbound material 1208 from the beads 1207;
(4) using droplet operations to separate off a portion of the combined slug 1210 to yield a portion 1212 comprising the beads with a reduced concentration of unbound target substance and a portion 1214 comprising unbound target substance;
(5) repeating steps (1)-(4) as needed to achieve the desired reduction in unbound material.

In a related approach, the slug may be continuously supplemented by adding additional wash droplets and/or slugs as the slug is being transported across the immobilized beads. The process may continue until the desired reduction in unbound material is achieved.

Figure 13:
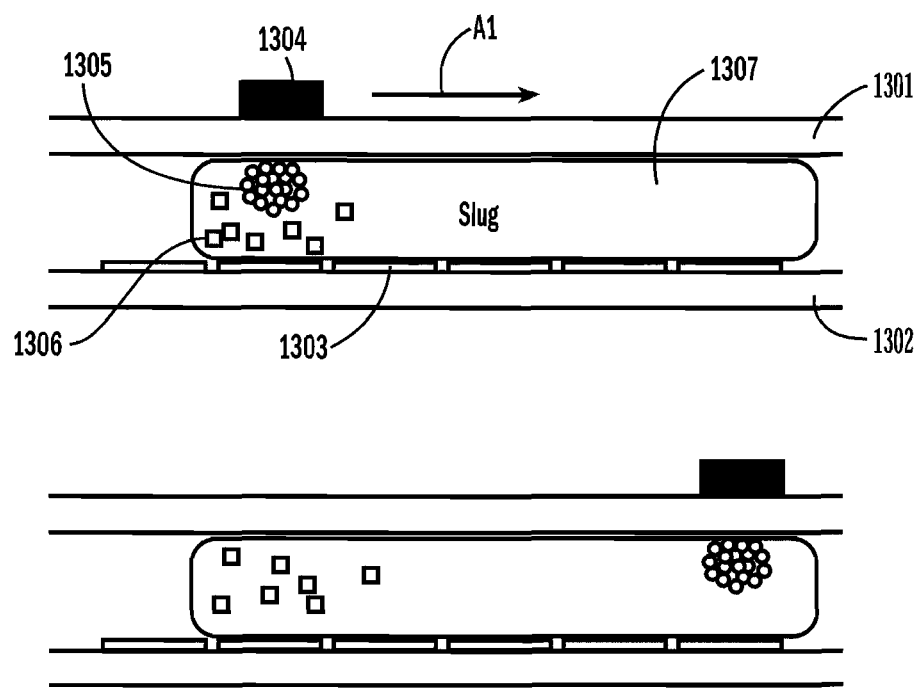

FIG. 13 illustrates an alternative embodiment which may also comprise a top plate 1301, bottom plate 1302, electrodes 1303, and a magnet 1304. In this embodiment, the magnet 1304 is moved, such as in the direction of A1, to separate beads 1305 from unbound material 1306 in a combined slug 1307 rather than moving the slug 1307. A similar approach involves movement of both the magnet and the slug to achieve separation (not shown). Yet another approach involves using multiple magnets to move the beads (not shown).

In embodiments in which magnetically responsive beads are used, the inventors have found that application of a magnetic field though useful for temporarily immobilizing beads, moving beads and/or positioning beads, sometimes results in unwanted aggregation of the beads. In one embodiment, a surfactant is included to prevent or reduce bead aggregation. Examples of surfactants suitable for this purpose include: Tween® 20, Tween® 80, Triton X-100. Surfactants should be selected and used in amounts which reduce or eliminate bead aggregation and minimize non-specific adsorption while at the same time not resulting in significant loss of target analytes or reagents from the droplet.

Another approach to eliminating or reducing clumping aggregation of beads involves the use of smaller numbers of larger beads. Any number of beads which can be contained in a droplet during one or more droplet operations may be used. In some embodiments, the number of magnetically responsive beads can range from 1 to several 100,000's. For example, in one embodiment, the invention makes use of one to 100 magnetically responsive beads per droplet. For example, the invention may make use of 1, 2, 3, 4, 5, 6, 7, 8, 9, 10 . . . 100 magnetically responsive beads per droplet. In one embodiment, the number of magnetically responsive beads is from one to 10. Use of smaller numbers of magnetically responsive beads permits larger beads to be used. For example, in one embodiment, the invention makes use of one to 100 magnetically responsive beads per droplet, where the beads have an average diameter of about 25 to about 100 microns. In another embodiment the invention makes use of one to 10 magnetically responsive beads per droplet, where the beads have an average diameter of about 50 to about 100 microns.

8.6.1.2 Washing Non-Magnetically Responsive Beads

Figure 14:
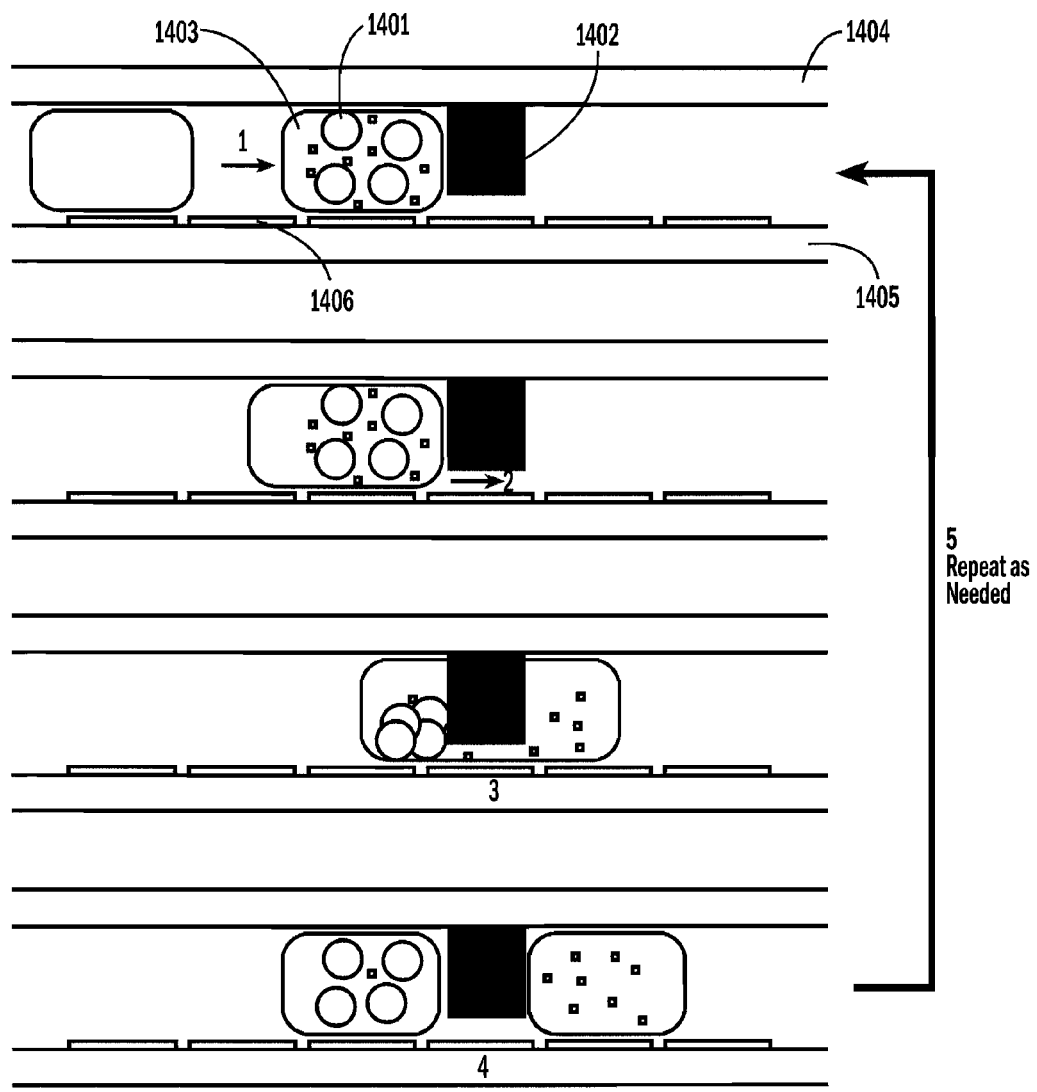
FIG. 14 is an illustration showing steps for immobilizing and freeing beads using a physical obstacle in accordance with an embodiment of the present invention.

A similar approach may be used with beads that are not magnetically responsive or not significantly magnetically responsive. As illustrated in FIG. 14, instead of using a magnetic field to immobilize beads 1401, a physical obstacle 1402 may be used to permit removal of some or all of droplet 1403 surrounding the beads 1401. The physical obstacle 1402 may, for example, include a membrane, sieve, and/or projection from the droplet microactuator (e.g., from the top plate 1404 and/or bottom plate 1405). Where a physical obstacle 1402 (projection or object) attached to the top plate 1404 and/or bottom plate 1405 is employed, it should be arranged so as to permit transport using one or more adjacent electrodes 1406 while preventing the beads 1401 from following, e.g., using a projection from the top plate that leaves sufficient space for droplet transport and/or a projection with one or more openings that permits the droplet to be transported through the opening while preventing the beads from following.

8.6.2 Washing Droplet Microactuator Surfaces

Figure 15:
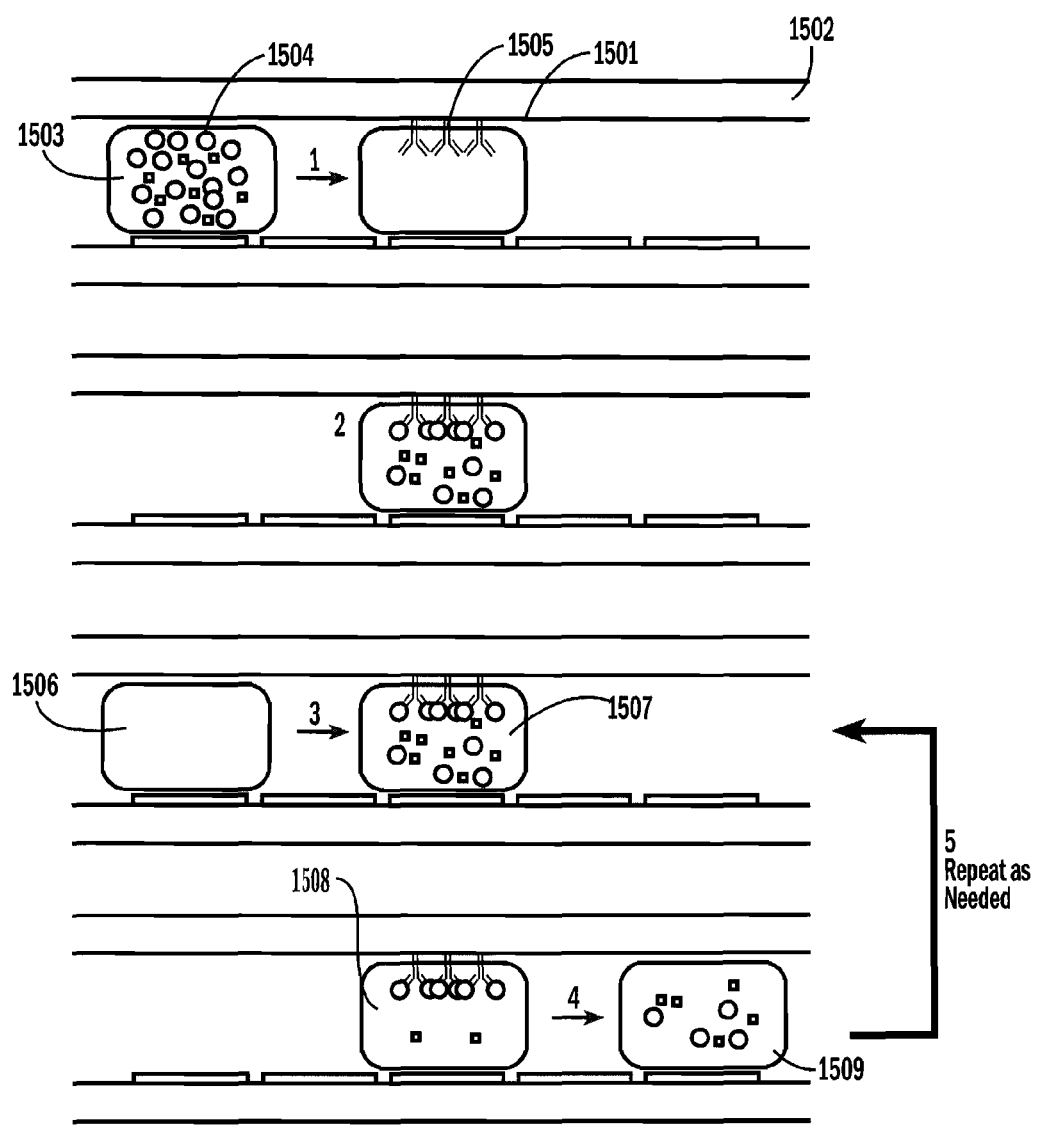
FIG. 15 is an illustration showing steps for washing a droplet microactuator surface in accordance with an embodiment of the present invention.

FIG. 15 illustrates an example of an approach for washing a droplet microactuator surface. In this non-limiting example, a surface 1501 is located on the interior of the top plate 1502. In this approach, (1) a sample droplet 1503 including a target substance 1504 having affinity for a surface component 1505 is (using droplet operations) brought into contact with the surface 1501, causing (2) some portion or all of the target substance to be immobilized. (3) A wash droplet 1506 and the sample droplet 1503 are combined using droplet operations to yield a combined wash-sample droplet 1507. (4) The combined wash-sample droplet is then divided using droplet operations to yield a portion 1508 in contact with the surface and comprising a reduced concentration of unbound target substance and a portion 1509 separated from the surface comprising unbound target substance. Steps (3) and (4) may be repeated as needed to achieve the desired reduction in unbound material.

8.7 Cell Handling

Various protocols of the invention may make use of droplets including cells. The droplets may include culture media for maintaining cell viability and/or growing cell cultures.

In some cases, the invention makes use of droplets having predetermined numbers of cells. For example, in some embodiments, the invention may make use of droplets including single cells. For example, droplets with single cells may be useful to product clonally pure cell populations and/or to conduct experiments studying the reaction of single cells to specific stimuli. Droplets with predetermined numbers of cells may be provided by dispensing droplets from a cell suspension onto a droplet transport pathway or network from a suspension of cells and/or by dividing droplets with multiple cells into one or more subdroplets. The suspension may be supplied from an external source or may be stored in a droplet microactuator reservoir. Droplets can be analyzed to determine the number of cells in each droplet, and droplets with a preselected number of cells can be routed downstream for further processing. Dispensed droplets with multiple cells may themselves be combined with one or more buffer droplets and divided into two or more sub-droplets and analyzed for the presence of single cells.

Sort decisions can be based on droplet analysis. For example, light transmission may be used to identify droplets with a predetermined number of cells. Sort decisions may be made based on the measurement of transmitted light. Other embodiments may employ automated image analysis and/or or multi-color fluorescence and/or scattering analysis. Droplets not meeting specifications can be reintroduced into the sample reservoir for another attempt or transported to a waste reservoir.

Figure 16A:
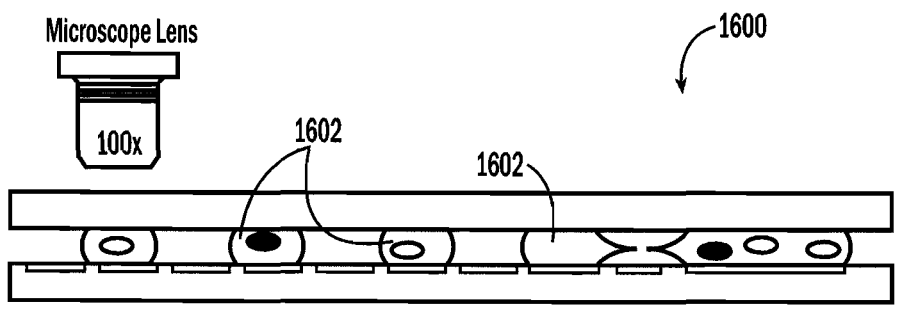
FIG. 16A is a side profile view and FIG. 16B is a top plan view of a droplet microactuator for transporting droplets in accordance with an embodiment of the present invention.
Figure 16B:
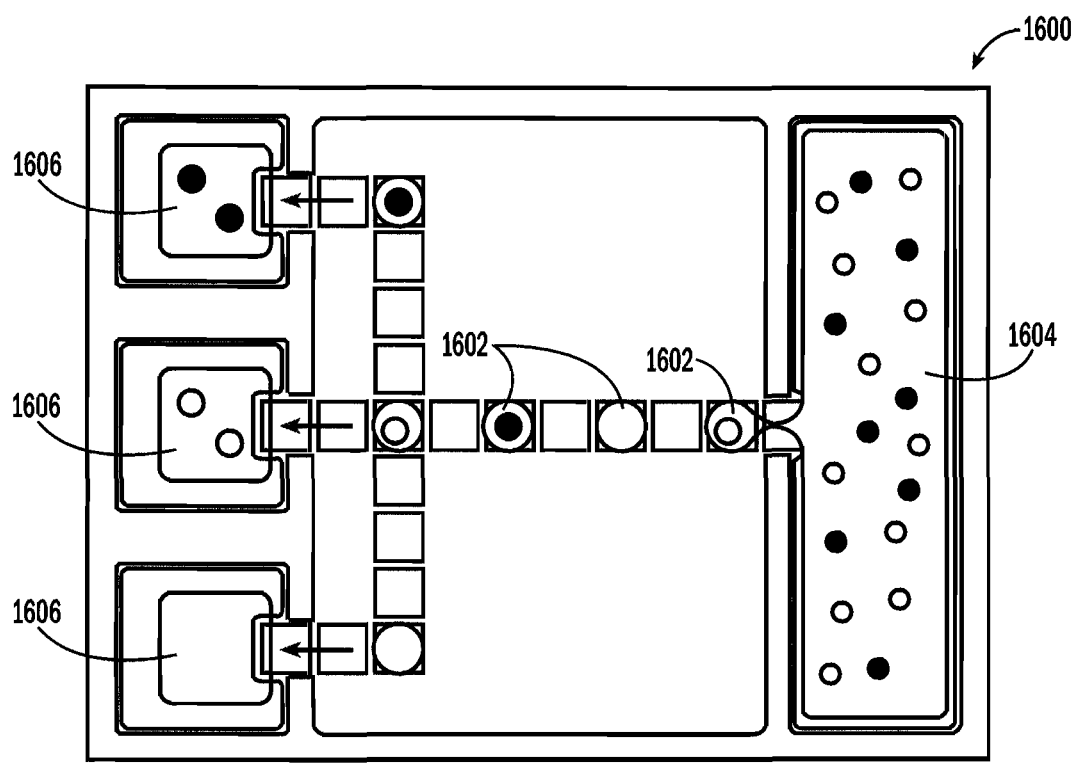

Droplets meeting cell count specifications may be transported to droplet microactuator reservoirs and/or transported for sorting and/or enrichment. One approach to providing reservoirs with enriched cell content is illustrated in FIGS. 16A and 16B. In this embodiment, droplets 1602 are dispensed from a cell suspension 1604 and transported based on their characteristics to reservoirs 1606 on droplet microactuator 1600.

In other embodiments, droplets may be further manipulated, e.g., as discrete droplets for analysis of the cells contained within. Droplets including predetermined numbers of cells may be used as inputs for various assay protocols described herein. In some embodiments, gravity is not used as the motive force for transporting droplets.

In one specific embodiment, tumor cells may be isolated on the droplet microactuator. Cells may, for example, be isolated from microliters of fine-needle aspirates (FNA). In another embodiment, samples such as blood stem cells, bone marrow, GI washes, and cryopreserved-thawed samples can be analyzed for cancer cells.

Immunogenic capture of relevant cells can be accomplished using antibody beads, such as anti-cytokeratin beads, may be used to capture relevant cells from a sample prior to introduction into the droplet microactuator and/or from a droplet on a droplet microactuator. Binding may be enhanced or incubation times reduced on the droplet microactuator by actively shuttling the droplet or vortexing the droplet within a reservoir. Beads can be isolated and washed as described elsewhere herein. Target cells can be released into suspension in a droplet on the droplet microactuator.

Uniform numbers of cells per droplet from can be dispensed from an on-chip reservoir using cell dispensing approaches described herein. Droplets with cells can be aliquoted into multiple on-chip reservoirs. Cells can be incubated in on-chip reservoirs. Cell viability can be assessed, e.g., using resazurin as a fluorescent redox indicator. Living cells convert the non-fluorescent resazurin dye into resorufin which fluoresces red. Non viable cells do not fluoresce. Cells can be distributed to on-chip reservoirs and nucleic acid from the cells can be amplified using approaches as described herein.

8.8 Droplet Microactuator Architecture and Operation

The system of the invention generally includes a droplet microactuator controlled by a processor. For example, the processor may, among other things, be programmed to control droplet manipulations on a droplet microactuator. A wide variety of droplet microactuator configurations is possible. Various illustrations are provided in FIGS. 1, 2, 6, 9, and 17. Examples of components which may be configured into a droplet microactuator of the invention include various filler fluids which may be loaded on the droplet microactuator; fluid loading mechanisms for introducing filler fluid, sample and/or reagents onto the droplet microactuator; various reservoirs, such as input reservoirs and/or processing reservoirs; droplet dispensing mechanisms; means for controlling temperature of the droplet microactuator, filler fluid, and/or a droplet on a droplet microactuator; and magnetic field generating components for manipulating magnetically responsive beads on a droplet microactuator. This section discusses these and other aspects of the droplet microactuator and their use in the systems of the invention.

8.8.1 Droplet Microactuator

The systems make use of a droplet microactuator. The droplet microactuator will include a substrate with one or more electrodes arranged for conducting one or more droplet operations. In some embodiments, the droplet microactuator will include one or more arrays, paths or networks of such electrodes. A variety of electrical properties may be employed to effect droplet operations. Examples include electrowetting and electrophoresis.

In one embodiment, the droplet microactuator includes two or more electrodes associated with a substrate, and includes a means for permitting activation/deactivation of the electrodes. For example, the electrodes may be electronically coupled to and controlled by a set of manual switches and/or a controller. The droplet microactuator is thus capable of effecting droplet operations, such as dispensing, splitting, transporting, merging, mixing, agitating, and the like. Droplet manipulation is, in one embodiment, accomplished using electric field mediated actuation. Electrodes will be electronically coupled to a means for controlling electrical connections to the droplet microactuator.

The basic droplet microactuator includes a substrate including a path or array of electrodes. In some embodiments, the droplet microactuator includes two parallel substrates separated by a gap and an array of electrodes on one or both substrates. One or both of the substrates may be a plate. One or both substrates may be fabricated using PCB, glass, and or semiconductor materials as the substrate. Where the substrate is PCB, the following materials are examples of suitable materials: Mitsui BN-300; Arlon 11N; Nelco N4000-6 and N5000-30/32; Isola FR406, especially IS620; fluoropolymer family (suitable for fluorescence detection since it has low background fluorescence); polyimide family. Various materials are also suitable for use as the dielectric component of the substrate. Examples include: vapor deposited dielectric, such as parylene C (especially on Glass), and parylene N; Teflon AF; Cytop; and soldermasks, such as liquid photoimageable soldermasks (e.g., on PCB) like Taiyo PSR4000 series, Taiyo PSR AUS series (good thermal characteristics for applications involving thermal control), and Probimer 8165 (good thermal characteristics for applications involving thermal control); dry film soldermask, such as those in the Dupont Vacrel family; and film dielectrics, such as polyimide film (Kapton), polyethylene, and fluoropolymers like FEP, PTFE. Some or all of the substrate may also include a hydrophobic coating. Suitable examples include Teflon AF; Cytop; coatings in the Fluoropel family; silane coatings; fluorosilane coatings; and 3M Novec electronic coatings.

Where the droplet microactuator includes two plates, droplets may be interposed in the space between the plates. Space surrounding the droplets typically includes a filler fluid. The droplet microactuator can conduct droplet operations using a wide variety of fluid droplets, though conductive fluids are preferred.

Surfaces of the droplet microactuator are typically coated with a hydrophobic coating. For applications involving thermal cycling, a hydrophobic coating should be selected that is resistant to thermal stress during prolonged thermocycling operation. Examples of suitable thermal resistant materials include soldermasks such as Probimer® 8165 which has been developed for use in the automotive industry and has excellent thermal shock resistance, and PCB board materials such as Mitsui BN-300 which is resistant to high temperature and warpage.

Droplet transport occurs along a path or network of control electrodes. The array or path includes electrical connections for electrically coupling electrodes to external circuitry. The array or path may also include electrical connections for electrically coupling certain electrodes together. The electrodes are controlled via the external circuitry by a processor. Droplet operations may be effected by supplying voltage to the electrodes. While the preferred voltage varies depending on the thickness of the dielectric, for a dielectric constant in the range of 2-100 and thickness in the range of 1 nm to 10 mm, the preferred energy per unit area limits are in the range of about 300 microjoule/sq meter to about 300000 microjoule/sq meter. The preferred activation voltage is in the range of about 1 mV to about 50 kV, or about 1V to about 10 kV, or about 5V to about 1000V, or about 10V to about 300V.

Typically, the electrodes are fired via a voltage relay. The droplet microactuator operates by direct manipulation of discrete droplets, e.g., using electrical fields. For example, a droplet adjacent to an energized electrode with surrounding electrodes grounded will transport to align itself with the energized electrode, i.e., the droplet will be transported to the position of that electrode. A series of successive transfers will transport droplets along the path or network of control electrodes. In addition to transport, other operations including merging, splitting, mixing and dispensing of droplets can be accomplished in the same manner by varying the patterns of voltage activation.

It should be noted that electrodes can be activated in a variety of ways. For example, an electrode can be activated by applying a DC potential. Similarly, an electrode can be activated by applying an AC potential, so that the activated electrode has an AC potential an unactivated electrode has a ground or other reference potential. In another aspect, the potential may be applied by repeatedly activating an electrode and then inverting it. An AC mode can be effected by using software to rapidly switch between polarities of the outputs.

In some embodiments the invention employs droplet operation structures and techniques described in U.S. Pat. No. 6,911,132, entitled "Apparatus for Manipulating Droplets by Electrowetting-Based Techniques," issued on Jun. 28, 2005 to Pamula et al.; U.S. patent application Ser. No. 11/343,284, entitled "Apparatuses and Methods for Manipulating Droplets on a Printed Circuit Board," filed on Jan. 30, 2006; U.S. Pat. No. 6,773,566, entitled "Electrostatic Actuators for Microfluidics and Methods for Using Same," issued on Aug. 10, 2004 and U.S. Pat. No. 6,565,727, entitled "Actuators for Microfluidics Without Moving Parts," issued on Jan. 24, 2000, both to Shenderov et al.; U.S. Patent Publication No. 20060254933, entitled "Device for transporting liquid and system for analyzing" published on Nov. 16, 2006 by Adachi et al., the disclosures of which are incorporated herein by reference for their teachings concerning structures and techniques for conducting droplet operations.

Droplet operations can be rapid, typically involving average linear velocities ranging from about 0.01 cm/s to about 100 cm/s, or from about 0.1 cm/s to about 10 cm/s, more preferably from about 0.5 cm/s to about 1.5 cm/s. Moreover, droplets may typically be manipulated at a frequency of manipulation ranging from about 1 Hz to about 100 KHz, preferably from about 10 Hz to about 10 KHz, more preferably from about 25 Hz to about 100 Hz. In addition to being rapid, droplet manipulations using the droplet microactuator are also highly precise, and multiple droplets can be independently and simultaneously manipulated on a single droplet microactuator.

Discrete droplet operations obviate the necessity for continuous-flow architecture and all the various disadvantages that accompany such an architecture. For example, near 100% utilization of sample and reagent is possible, since no fluid is wasted in priming channels or filling reservoirs. Further, as noted above, droplet movement can be extremely rapid. The droplet microactuator may in some cases be supplemented by continuous flow components and such combination approaches involving discrete droplet operations and continuous flow elements are within the scope of the invention. Continuous flow components may be controlled by the controller. Nevertheless, in certain other embodiments, various continuous flow elements are specifically avoided in the droplet microactuator of the invention and/or methods of the invention. For example, in certain embodiments, one or more of the following components is excluded from a droplet microactuator and/or methods of the invention: microchannels; fixed microchannels; networks of microchannels; pumps; external pumps; valves; high-voltage supplies; centrifugal force elements; moving parts.

Electric field mediated actuation also obviates the need for other droplet operations and all the various disadvantages that accompany such techniques. It will be appreciated that the droplet microactuator may nevertheless be complemented or supplemented with other droplet manipulation techniques, such as electrical (e.g., electrostatic actuation, dielectrophoresis), magnetic, thermal (e.g., thermal Marangoni effects, thermocapillary), mechanical (e.g., surface acoustic waves, micropumping, peristaltic), optical (e.g., opto-electrowetting, optical tweezers), and chemical means (e.g., chemical gradients). When these techniques are employed, associated hardware may also electronically coupled to and controlled by the controller. However, in other embodiments, one or more of these droplet operation techniques is specifically excluded from a droplet microactuator of the invention.

The droplet microactuator can be manufactured in a highly compact form and can be driven using a very small apparatus. For example, droplet microactuator and apparatus may together be as small as several cubic inches in size. The droplet microactuator requires only small amounts of electrical power and can, for example, readily be operated using batteries. The droplet microactuator can perform droplet operations using extremely small droplets. Droplets are typically in the range of from about 1 fL to about 1 mL, more preferably from about 100 pL to about 1 µL, still more preferably from about 10 nL to about 1 µL.

The use of discrete droplets for on-chip processing instead of continuous flows provides several important advantages. Since sample fluid need not be expended for priming of channels or pumps virtually all of the sample fluid can be used for analysis and very small volumes of sample (e.g., less than about 100 µL or less than about 50 µL or less than about 25 µL) can be analyzed. The same advantages apply to the use of reagents where reducing the volume of reagents consumed has the advantage of reducing the cost of the analysis. The use of discrete small-volume droplets also permits a large number of reactions to performed in a small footprint (e.g. greater than 10 per $cm^2$ or greater than 100 per $cm^2$ or greater 1,000 per $cm^2$ or greater than 10,000 per $cm^2$).

Various components of the invention may be included as components of the droplet microactuator. In fact, an entire system of the invention may be provided as an integrated droplet microactuator. In some embodiments, the droplet microactuator includes various sensors and means for electronically coupling the sensors to external circuitry. In other embodiments, the droplet microactuator includes heaters and/or magnetic field generating elements and means for coupling such elements to external circuitry. Further, a droplet microactuator including any one or more of the reagents described herein in a reservoir or in droplet form is also an aspect of the invention.

Optical windows can be patterned in the electrodes to enhance the capability of performing optical detection on the chip. Where the electrode is formed in an opaque material on a transparent substrate, a window in the electrode can be created permit light to pass through the substrate. Alternatively, when the electrode material is transparent, a mask can be created to eliminate stray light. Additionally, the opening can be patterned as a diffraction grating. Adaptive optical windows can be created as well, using a second electrowetting layer. For example, opaque oil (e.g. oil dyed black) can be used with a transparent droplet to create an temporary and movable optical window.

8.8.2 Cartridge

In some embodiments, the invention includes a cartridge for coupling to the droplet microactuator. It will be appreciated that a cartridge, while not necessary to the operation of the invention, may be convenient in some circumstances. When present, the cartridge may include a means for electrically coupling the path or network of the droplet microactuator to a processor, e.g., a processor of a droplet microactuator system of the invention. In this embodiment, the electrical connection is: electrodes—cartridge—processor, where there may be additional elements between the three. In another embodiment, the cartridge may include means for physically coupling to the droplet microactuator. In this embodiment, the electrical connection may be: electrodes—processor—cartridge. Alternatively, the cartridge may lack electrical components altogether.

When present, the cartridge may include reservoirs for one or more reagents, e.g., pre-loaded reagents. The droplet microactuator may be configured so that a fluid path may be established between the cartridge reservoirs and the interior of the droplet microactuator for flowing reagents, sample and/or filler fluid from the cartridge onto the droplet microactuator. For example, preloaded cartridge reservoirs may be dispensed into the droplet microactuator prior to, during, or after coupling of the cartridge to the analyzer. The cartridge may be sealed, self-contained and/or disposable. It may be supplied with or without a droplet microactuator. Such cartridges can be used to ensure repeatable assay conditions, permit safe handling and disposal of infectious or hazardous material, and/or reduce cross-contamination between runs. The cartridge may, for example, include a machined plastic part. It may be affixed to and provided in combination with the droplet microactuator.

The cartridge materials are selected to provide storage of reagents without degradation or contamination of the reagents. Moreover, they should be selected to provide reliable operation at elevated temperature and to ensure compatibility with the real-time chemistry. They may, for example, include molded plastic components. In some embodiments, sealed, disposable test cartridges enhance operator safety and facilitate safe disposal.

Various components of the droplet microactuator system may be included on the cartridge. For example, the top-plate, which encloses the interior space of the droplet microactuator, may be provided as a component of the cartridge. Various sensors may also be included as components of the cartridge.

8.8.3 Filler Fluid

The droplet microactuator of the invention includes one or more free (i.e. fluid-fluid) interfaces. Examples include a liquid-liquid or liquid-gas interface. Typically chemistry is performed in the primary (droplet) phase, and the secondary phase serves as a filler fluid separating the droplets from each other. The secondary phase can, for example, be a liquid, gel and/or a gas. Where the secondary phase includes a liquid, the liquid is sufficiently immiscible with the primary liquid phase to permit the droplet microactuator to conduct one of more droplet operations.

It should also be noted that the droplet microactuator may include more than two phases. For example, in one embodiment the droplet microactuator operates based on an aqueous-oil-air three-phase system. In a related environment, the droplet microactuator may operate based on an aqueous-first oil-second oil three-phase system, such as a system including an aqueous droplet surrounded by silicon oil, which is in turn surrounded by a fluorosilicon oil. Generally, three-phase systems will include three components which are mutually immiscible or substantially immiscible.

In another embodiment, oil or another immiscible liquid may be used as a droplet encapsulant for electrowetting. For example, a droplet can be encapsulated in a shell of oil by moving the droplet through an air/oil interface. Each droplet would then have its own local bath of oil with the space between encapsulated droplets filled with either air or a third immiscible liquid. Among other advantages, this approach is useful for minimizing the transfer of material between droplets in the system by partitioning into the oil phase while retaining the advantageous properties of the oil with respect to evaporation and fouling of the surface. This approach may also be used to facilitate electrowetting of non-electrowettable liquids which are immiscible with electrowettable liquids. In a specific embodiment of this concept the immiscible liquid can be chosen to be crosslinkable (by UV, heat, moisture or chemically) to create capsules of liquids with solid shells, for drug delivery synthesis applications.

Further, in some applications it may be desirable or necessary to perform certain operations in an immiscible liquid, such as oil, and others in air. The invention includes hybrid systems in which droplet manipulation is performed both in air and in an immiscible liquid filler fluid such as oil. For example, samples may be processed under oil and then transported into an air-medium portion for evaporation for subsequent analysis by MS. Conversely, a sample could be collected in air and then processed with droplets under oil. Thus, the droplet microactuator may include a transport path for moving droplets from a droplet microactuator surface in a space filled with filler fluid to a droplet microactuator open to the atmosphere or including a gaseous filler fluid.

The filler fluid may be any fluid in which the droplet microactuator can, under the right conditions, conduct one or more droplet operations. It should be noted that certain filler fluids may be solids or highly viscous fluids under certain conditions, e.g., during transport, while they are transformed into fluids for operation, e.g., by heating. The filler fluid may be a liquid or gas during operation of the droplet microactuator. Examples of suitable liquid filler fluids include, without limitation, silicone oils; fluorosilicone oils; hydrocarbons, including for example, alkanes, such as decane, undecane, dodecane, tridecane, tetradecane, pentadecane, hexadecane; aliphatic and aromatic alkanes such as dodecane, hexadecane, and cyclohexane, hydrocarbon oils, mineral oils, paraffin oils; halogenated oils, such as fluorocarbons and perfluorocarbons (e.g. 3M Fluorinert liquids); mixtures of any of the foregoing oils in the same class; mixtures of any of the foregoing oils in different classes. Examples of suitable gas filler fluids include, without limitation, air, argon, nitrogen, carbon dioxide, oxygen, humidified air, any inert gases. In one embodiment, the primary phase is an aqueous solution, and the secondary phase is air or an oil which is relatively immiscible with water. In another embodiment, the filler fluid includes a gas that fills the space between the plates surrounding the droplets. A preferred filler fluid is low-viscosity oil, such as silicone oil. Other suitable fluids are described in U.S. Patent Application No. 60/736,399, entitled "Filler Fluids for Droplet-Based Microfluidics" filed on Nov. 14, 2005, the entire disclosure of which is incorporated herein by reference. The fluid may be selected to prevent any significant evaporation of the droplets.

The phases of the fluids used in the protocols of the invention may be selected to facilitate protocols of the invention without undue formation of bubbles, loss of reagent to the filler fluid, and/or adherence of reagent to the droplet microactuator surface.

In certain embodiments of the invention the filler fluid may be selected to reduce or prevent evaporation of sample, reagent, or other droplets utilized in the protocols of the invention. The filler fluid may be selected to prevent sample, reagent, or other droplets utilized in the protocols of the invention from evaporating and becoming too small for further effective manipulation. Similarly, the filler fluid can be selected to prevent evaporation of sample, reagent, or other droplets utilized in the protocols of the invention from detrimentally concentrating species within the droplets in a manner which results in an unduly adverse affect on the intended use of the droplet. Moreover, the filler fluid may be selected to reduce or prevent transport of material from sample, reagent, or other droplets utilized in the protocols of the invention across the phase boundary to maintain droplet volume and/or ensure reliable microfluidic operation and/or assay results. Miscibility between phases can sometimes result in shrinking (or swelling) of the droplet phase. To prevent or reduce this problem, one or more phases of the system may be saturated with the equilibrium concentration of another phase to reduce shrinking or swelling. Thus, for example, the filler fluid may be saturated with the equilibrium concentration of the solvent for sample, reagent, or other droplets utilized in the protocols of the invention, and/or one or more of the sample, reagent, and/or other droplets utilized in the protocols of the invention may be saturated with the equilibrium concentration of the filler fluid.

In some embodiments, a liquid filler fluid is selected to minimize contact between the droplet and droplet microactuator surfaces. That is, a film of liquid may exist between the droplet and surface which prevents material within the droplet from coming into contact with and adhering to the coated surface. This approach helps to prevent fouling of the surface and related interference with droplet transport. For example, it has been observed that high concentrations of certain proteins in water droplets readily stick to certain hydrophobic surfaces spoiling the hydrophobic nature of these surfaces; whereas, the same droplets can be moved across the same surfaces without appreciable adhesion of proteins if bathed in an oil which minimizes contact between the two surfaces. This approach may also help to avoid cross-contamination between droplets caused by deposition of material from one droplet which is then picked up by a second droplet. In a similar embodiment, a film between the droplet and droplet microactuator surface can be used to lubricate the droplet by preventing friction-like physical interactions between the droplet and surface during droplet operations.

In one embodiment, the invention provides a thin coating of a liquid filler fluid layer in an otherwise gas filled system. For example, the invention provides a microfluidic system including an open or enclosed system including a thin layer of filler fluid, such as oil, layered on a droplet microactuator surface, wherein the system is otherwise filled with a gas. The oil is of sufficient thickness to provide lubrication and contamination of droplet microactuator surfaces and contamination of droplets via droplet microactuator surfaces. Preferably the oil is selected to minimize transport of material between the droplet and oil phases. One advantage of this approach is reduction of carry-over in the droplet microactuator. The surface may in some embodiments be treated by coating it with the filler fluid while operating in air. This approach is also useful for loading operations as a means to retain the lubricating effect of oil while avoiding trapping of oil bubbles in the bulk filler fluid.

Treatment of a Teflon AF surface with silicone oil can provide some of the lubrication benefit of silicone oil filler fluid even when operating in air. This approach can be used to prime the droplet microactuator with a lubricating layer of oil, followed by replacement with air to allow samples to be loaded without introduction of bubbles, followed by re-introduction of oil to prevent evaporation of the samples. Thus the benefits of each kind of system are available depending on the type of microfluidic processing to be carried out.

In another embodiment, the filler fluid can be completely exchanged at different steps within a protocol. For example, a gas filler fluid can be introduced during sample loading to prevent trapping of air bubbles and then a liquid filler fluid can be pumped in to prevent evaporation of the liquid. Different types of filler fluid can be pumped into or out of the system depending on the particular assay steps to be performed.

In yet another embodiment, multiple filler fluids can be used within a single system. For example, a droplet microactuator can be selected to have separate gas filled and liquid filled regions. Operations or certain types of droplets can be segregated between the different filler fluid regions.

The filler fluid may be selected based on its refractive index to either match the droplet to prevent refraction of light passing through or near the droplet. Alternatively the filler fluid may be selected with a refractive index that differs from the droplet to provide contrast for certain types of optical measurements or optical manipulations. A filler fluid may be chosen to have a lower index of refraction than the primary liquid so that light can be transmitted though the primary liquid by total internal reflection. The primary phase can include highly elongated droplets which can serve as "light pipes" to convey light between two locations, e.g. to facilitate optical analyses.

The filler fluid may be selected based on its color to facilitates direct or indirect visualization of the droplet, e.g., by providing contrast between the sample, reagent, and/or other droplets used in the protocols of the invention and the filler fluid. This approach can enhance visualization of the different phases, for example to distinguish droplets from filler fluid or from air bubbles. In optical applications, the differential absorbance of the two phases can be used to modulate the color of light passing through the system. As another example, in applications where fluorescence measurements are made within droplets it may desirable for the oil to include molecules, such as dyes, that absorb the emitted wavelength of light to minimize cross-talk between reactions occurring in adjacent droplets.

The filler fluid may be selected to have particular thermal properties that can either thermally insulate the droplets or conduct heat away from the droplets. For example, in the amplification protocols of the invention, a thermally conductive or low heat capacity filler fluid may be desirable to permit rapid changes in temperature. For applications where a steady temperature is required a thermally insulating or high heat capacity filler fluid can be used to provide temperature stability.

The filler fluid may be selected to undergo a phase change upon presentation of an appropriate stimulus. For example, a wax-like filler fluid (e.g. paraffin wax or octadecane) can be used where the filler fluid is changed from solid to liquid form by application of heat. Lowering the temperature would return the filler fluid to a solid so that droplets would be contained within a solid matrix. Encapsulation of the liquid phase within a solid may facilitate storage and handling of the sample, reagent, and/or other droplets utilized in the protocols of the invention and/or allow for safe and convenient disposal of the materials following use of the droplet microactuator. The filler fluid can be stored as a solid on the droplet microactuator, in a cartridge-based reservoir, or elsewhere, and heated to permit the fluid to flow into and fill the droplet microactuator. Or the immiscible filler fluid can be selected to be crosslinkable (by UV, heat, moisture or chemically) to create capsules of liquids within a solid shell.

The filler fluid may be selected to have particular gas permeability or saturation properties. In certain applications a reaction occurring inside the droplet may consume oxygen or other gas which may need to be replenished by gas contained within or transported through the filler fluid. For example, some fluorinated oils have useful gas permeability properties for such applications. Alternatively, the filler fluid may be selected to exclude certain gases from the droplet, for example to maintain anaerobic conditions within the droplet. The filler fluid may be selected to have a certain degree of miscibility or partitioning into the droplet phase. Usually, complete or substantially complete lack of miscibility between the droplet and filler fluid is desired, but some applications may benefit from some limited degree of miscibility between the phases or partitioning of particular molecules between the phases, e.g., liquid-liquid extraction applications. In certain applications where dissolved gases in the filler fluid may be problematic, a means for degassing the filler fluid prior to or during use may need to be provided. For example, filler fluid may be degassed by incubation under vacuum, heating, sparging or by centrifugation.

The filler fluid may be selected to have a particular surface or interfacial tension with the droplet phase or with the droplet microactuator surfaces. Surfactants can be added to the filler fluid to stabilize liquid films that may be present between the droplet and solid phases. Examples of suitable surfactants include nonionic low HLB (hydrophile-lipophile balanced) surfactant. The HLB preferably less than about 10 or less than about 5. Suitable examples include: Triton X-15 (HLB=4.9); Span 85 (HLB 1.8); Span 65 (2.1); Span 83 (3.7); Span 80 (4.3); Span 60 (4.7); and fluorinated surfactants.

Surfactants are preferably selected and provided in an amount which (1) results in more droplet operations on the droplet microactuator as compared to corresponding droplet microactuator without the surfactant; or (2) makes one or more droplet operations possible on the droplet microactuator as compared to corresponding droplet microactuator without the surfactant; or (3) makes one or more droplet operations more reliable on the droplet microactuator as compared to corresponding droplet microactuator without the surfactant. In a related example, surfactants are preferably selected and provided in an amount which makes one or more droplet operations possible or more reliable for droplets including one or more specific reagents or mixtures on the droplet microactuator as compared to droplet operations for the same droplets including one or more specific reagents or mixtures on a corresponding droplet microactuator without the surfactant. In another related example, surfactants are preferably selected and provided in an amount which makes one or more droplet operations possible or more reliable for one or more droplets including amphiphilic molecules on the droplet microactuator as compared to droplet operations for the same droplets including amphiphilic molecules on a corresponding droplet microactuator without the surfactant.

In a preferred embodiment, the surfactant is added to the filler fluid in an amount which ranges from about 0.001 to about 10% w/w, or about 0.001 to about 1% w/w, or about 0.001 to about 0.1% w/w. For example, in one embodiment the filler fluid is 2 cSt silicone oil and the surfactant is Triton X-15 in an amount which ranges from about 0.001 to about 10% w/w, or about 0.001 to about 1% w/w, or about 0.001 to about 0.1% w/w. The solid-liquid interfacial tension may be adjusted to control the wetting of the filler fluid on the droplet microactuator surfaces, for example, to control the formation, thickness or behavior of thin films of the filler fluid between the droplet and droplet microactuator surfaces or to control the wetting behavior of the fluid when filling or emptying it from the droplet microactuator.

By doping filler fluid with surfactant, the inventors have discovered that it is possible to increase the concentrations of compatible protein solutions by more than 3 orders of magnitude, from mg/L to mg/mL. The inventors were able to reliably dispense and transport 25 nL droplets of 75 mg/mL lysozyme solution using the new filler fluid. For example, the filler fluid may be a silicone oil doped with a surfactant, such as Triton X-15. Preferably the surfactant is a lipophilic surfactant. In one embodiment, we added 0.1% (w/w) Triton X-15, a lipophilic surfactant, to the oil so that high concentrations protein droplets could be formed or dispensed from on-chip reservoirs. Droplet transport for all compatible fluids is fast (typically about 3-10 cm/sec) and reliable (>25,000 operations). In one embodiment, the filler fluid includes a surfactant dopant in an amount which results in an increase in the concentration of a protein that can be reliably dispensed on the droplet microactuator.

The filler fluid may be selected to have a particular viscosity or volatility. For example, a low viscosity liquid (e.g. 0.65 cSt. Silicone oil) facilitates transport of droplets while a low volatility filler fluid (e.g., 2, 5 or 10 cSt. Silicone oil) may be desirable to prevent loss of filler fluid by evaporation, particularly in nucleic acid amplification applications performed at elevated temperature. In some applications, evaporation of the filler fluid can be desired, so a low volatility filter fluid may be selected. The filler fluid may be selected to have a particular viscosity dependence on temperature, since the viscosity of the filler fluid affects the fluid dynamics and the temperature on the droplet microactuator may vary. In nucleic acid amplification protocols of the invention, the filler fluid is selected so that any viscosity changes resulting from thermal cycling are not unduly detrimental to conducting droplet operations required for effecting the amplification protocols.

The filler fluid may be selected to have particular electrical properties. For example, certain applications including electrowetting favor the use of a filler fluid that is non-conductive (e.g., silicone oil). Or the dielectric permittivity can be selected to control the coupling of electrical energy into the system from external electrodes. In certain applications a non-conductive filler fluid can be employed as an electrical insulator or dielectric in which the droplet floats just above the electrodes without physically contacting them. For example, in an electrowetting system a layer of filler fluid (e.g., silicone oil) between the droplet and electrode can be used to provide electrostatic control of the droplet. Filler fluids may be deionized to reduce conductivity.

The filler fluid may be selected to have a particular density relative to the droplet phase. A difference in density between the two phases can be used to control or exploit buoyancy forces acting upon the droplets. Examples of two-phase systems useful in this aspect of the invention include water/silicone oil, water/flourinert, and water/fluorosilicone oil. When one phase is buoyant, then that effect can be exploited in a vertical configuration as a means to transport one phase through the other. For example, a waste or collection well can exist at the top or bottom of the droplet microactuator where droplets are delivered to that reservoir by simply releasing them at an appropriate point and allowing them to float or sink to the target destination. Such an approach may be suitable for use in removing reactant from a droplet microactuator, e.g. removing fluid containing amplified nucleic acid for use in other processes. Density differences can also be used as a means to control or engineer contact between the droplets and droplet microactuator surfaces. For example, a droplet not normally contacting a top-plate can be released to sink or float to that surface to contact it. Density differences and buoyancy effects can also be exploited for sensing applications in which the movement of droplets is detected and related to a change in position, orientation or acceleration.

The filler fluid is selected for material compatibility with the droplet microactuator surfaces. For example, certain filler fluids can etch, dissolve, contaminate, absorb into or otherwise be incompatible with certain droplet microactuator materials. For example, fluorinated hydrocarbons, such as Fluorinert, may be incompatible with Teflon AF or Cytop surfaces because of their tendency to dissolve these materials, while silicone oils may be incompatible with PDMS surfaces due to the tendency of these materials to dissolve each other.

The filler fluid is selected for biochemical compatibility with sample and reagents used in the protocols of the invention.

The invention may include means for controlling the introduction or circulation of the filler fluid within the droplet microactuator, cartridge and/or system. In one mode of operation the filler fluid is injected once during the initialization of droplet microactuator operation. The filler fluid may be provided from an external source using a syringe, dropper, pipettor, capillary, tube or other means. Alternatively, the filler fluid may be provided from a reservoir internal to the droplet microactuator assembly or cartridge. As an example, the fluid can be contained within a sealed pouch which is punctured or compressed to transfer the liquid into the droplet microactuator.

In another mode of operation a means can be provided for multiple introductions or recirculation of one or more filler fluids within the droplet microactuator. A secondary fluid-handling system can be provided to inject and to remove fluid from within the droplet microactuator. Pressure, gravity or other means such as the use of thermal gradients can be used to transport the filler fluid into or out of the droplet microactuator. Such a system can be used for the following purposes:
(1) To replenish filler fluid lost to evaporation or leakage over time. A slow steady flow or periodic injection of filler fluid can be employed to make up for any loss of filler fluid volume.
(2) To provide "clean" filler fluid either continually or periodically to reduce contamination between droplets. The filler fluid can be cleaned either by completely replacing it or by circulating it through a filter or bed of absorbent material selected to remove contaminants.
(3) To provide a means for transporting droplets to waste. For example, at the end of an assay, droplets can be released and allowed to flow with the filler fluid to the outlet providing a means to "flush" the droplet microactuator. Flushing the droplet microactuator can be performed to reset the status of the droplet microactuator in preparation to perform additional assays.
(4) To exchange the filler fluid when different fluids may be desired for certain steps, for example to replace oil with air to allow drying of droplets, or to replace one oil with a different oil.
(5) To provide a means of controlling the temperature of the droplets by heating or cooling the fluid as it is circulated through the droplet microactuator. For example, PCR can be performed in droplets containing the appropriate PCR reagents (e.g., primers, nucleotides, and polymerase) by circulating temperature controlled filler fluid through the droplet microactuator to perform thermocycling. The temperature of the filler fluid entering and leaving the droplet microactuator can be directly measured and the temperature and flow rate of the filler fluid can be adjusted to provide optimal temperature control inside the droplet microactuator.

Local regions of filler fluid or even individual units of filler fluid for each droplet can be used. For example aqueous droplets can be encapsulated in an individual shell of fluid, such as oil, which moves along with that droplet. Each such droplet would then have its own local fluid bath with the space between encapsulated droplets filled with third immiscible liquid such as air or fluorosilicone oil. This approach can be used to minimize the transfer of material between droplets in the system by partitioning into the oil phase while retaining the advantageous properties of the oil with respect to evaporation and fouling of the surface. The shells of oil can be created by simply moving the droplet through an oil interface, pinching off a unit of oil as the droplet creates a bulge along the interface.

Hybrid systems can be implemented in which different regions of the droplet microactuator are filled with different fluids. For example, samples can be processed under oil and then transported into an air portion to be evaporated for subsequent analysis by MS. Conversely, a sample can be collected in air and then processed under oil.

Magnetically responsive beads can be used to move material between oil and water phases on a droplet microactuator. Generally, water-soluble compounds or materials tend to remain within the droplets, unable to cross the oil-water meniscus in significant quantities, and oil-soluble compounds or materials remain in the lipophilic filler fluid. When the material is attached to magnetically responsive beads, a magnetic field may be used to move the beads and attached material across the oil-water boundary. The beads need to be selected such that they have sufficient affinity for oil and water so that they can readily cross the meniscus. This operation is useful for drying or concentrating materials and can also be used to facilitate washing and/or dilution. For example, material bound to a magnetically responsive bead can be removed from one droplet and transferred by way of the filler fluid to another droplet.

Filler fluid can be circulated through the droplet microactuator to reduce contamination during and/or between runs. Filler fluid can be continually or periodically flowed through the droplet microactuator, so that fresh filler fluid is constantly supplied to the droplet microactuator. In addition to removing contaminates contaminated oil, this technique could be used at the end of a run to clear droplets from the array by removing the voltage so that droplets are released and flow with the oil to an exterior of the droplet microactuator and/or into a waste reservoir.

8.8.4 Droplet Microactuator Loading

The droplet microactuator generally includes one or more input ports for the introduction of one or more filler fluids, reagents and/or samples (e.g., reagents and/or samples for conducting protocols and/or assays as described elsewhere herein, e.g., in Sections 8.1, 8.2, 8.3, 8.4 and/or 8.5) into the droplet microactuator. In some embodiments, samples or reagents are loaded via the input ports using conventional robotics. In one alternative embodiment, droplets of sample or reagent are separated by plugs of oil in a long pre-loaded glass capillary which when connected to the droplet microactuator allows droplets of sample or reagent to be captured and routed on the droplet microactuator as they are pumped out of the capillary into the input port. Another loading technique involves pre-stamping reagents onto the droplet microactuator and allowing them to dry, e.g., using a high-speed reagent stamping or printing process. Yet another approach involves the use of a direct plate-to-droplet microactuator interface in which the contents of plates, e.g., 1536 or 384 or 96 well plates, are transported onto the droplet microactuator in parallel by using pressure to force the contents through input ports aligned with wells. Loading hardware may in some embodiments be electronically coupled to and controlled by the controller.

8.8.5 Reservoirs

The droplet microactuator includes various reservoirs, such as input reservoirs and/or processing reservoirs.

8.8.5.1 Input Reservoirs

In some embodiments, the droplet microactuator includes one or more input reservoirs in fluid communication with one or more input ports, typically in direct fluid communication with the input ports. The input reservoir(s) serve as reservoirs for storage of bulk source material (e.g. reagents or samples) for dispensing droplets (e.g. reagent droplets or sample droplets). Thus, the input reservoir(s) may, for example, serve as sample wells or reagent wells.

The input reservoirs generally include one or more well walls defining an interior space and an opening. The interior space defined by the well walls is at least partially isolated by the well walls from the remainder of the interior of the droplet microactuator. The well may be adjacent (in any direction, e.g., vertically or laterally) to a port suitable for introduction of fluid from an exterior of the droplet microactuator into the input reservoir. One or more openings in the well walls may be provided to enable fluid communication with the interior volume of the droplet microactuator for dispensing of droplets into this interior volume. The opening(s) may permit fluid to flow or be transported into the interior volume of the droplet microactuator onto the path or network of electrodes. Input reservoirs may also include one or more vents for permitting displacement of filler fluid from the input reservoir as fluid is introduced into or removed from the well via the port or the opening.

The input reservoirs may further include one or more planar control electrodes in a top or bottom plate adjacent to or within the space defined by the well walls. The planar electrodes are electronically coupled to and controlled by the controller. In a preferred embodiment, the planar electrode has two or more branches or rays, such that activation of the control electrode during droplet dispensing in the presence of a fluid exerts a "pull" on the fluid in a direction which is generally opposite to the direction of droplet dispensing. In some cases, the shape of the electrode results in a multi-vector pull having a mean vector which has a direction generally opposite to the direction of the droplet being dispensed.

Well walls may, for example, be formed by protrusions from the top or bottom plates, and/or may be formed by deposition of a wall-forming material on a surface of the top or bottom plate. For example, well walls may be formed from a soldermask material or polymeric gasket material deposited and patterned on the surface. In some embodiments a source of continuous or semi-continuous sample or reagent flow is coupled in fluid communication with one or more of the input ports.

It should be noted that while droplet dispensing may be conducted from defined reservoirs, in some embodiments, droplet dispensing is conducted without the use of physically defined reservoirs. Dispensing may proceed from source droplet which is confined during droplet dispensing, e.g., by electrowetting forces or by hydrophilic surfaces.

8.8.5.2 Processing Reservoirs

The droplet microactuator may also include one or more processing areas or reservoirs. These areas or reservoirs serve as a location for executing various droplet processing steps, such as mixing, heating, incubating, cooling, diluting, titrating, and the like. The droplet microactuator includes one or more paths or networks of control electrodes sufficient to transport droplets from the one or more input ports to the one or more processing areas or reservoirs. In some cases the processing areas are simply components or sections of these paths or networks. In other embodiments, the processing areas are defined processing reservoirs. Such reservoirs may, for example, be structured generally in the same manner as the input reservoirs described above. However, the processing reservoirs are typically not in direct fluid communication with the input ports, i.e., droplet transport along the one or more paths or networks of control electrodes is required add reagent or sample to the processing reservoir(s). In some cases, the processing reservoirs include a path or network of reservoirs therein to permit droplet operations within the processing reservoirs.

8.8.5.3 Droplet Operations

The droplet microactuator may conduct various droplet operations with respect to a droplet. Examples include: loading a droplet into the droplet microactuator; dispensing one or more droplets from a source droplet; splitting, separating or dividing a droplet into two or more droplets; transporting a droplet from one location to another in any direction; merging or combining two or more droplets into a single droplet; diluting a droplet; mixing a droplet; agitating a droplet; deforming a droplet; retaining a droplet in position; incubating a droplet; heating a droplet; vaporizing a droplet; cooling a droplet; disposing of a droplet; transporting a droplet out of a droplet microactuator; other droplet operations described herein; and/or any combination of the foregoing.

Droplet dispensing refers to the process of aliquoting a larger volume of fluid into smaller droplets. Dispensing is usefully employed at the fluidic interface, the input reservoirs, and at processing reservoirs. Droplets may be formed by energizing electrodes adjacent to the fluid reservoir causing a "finger" of fluid to be extended from the reservoir. When the fluid front reaches the terminal electrode, the intermediate electrodes are de-energized causing the fluid to retract into the reservoir while leaving a newly-formed droplet on the terminal electrode. As previously noted, one or more electrodes in the reservoir may also be energized to assist in separating the droplet being dispensed from the bulk fluid. Because the droplet conforms to the shape of the electrode, which is fixed, excellent accuracy and precision are obtained. Droplet dispensing is controlled by the controller. In some embodiments the invention employs droplet dispensing structures and/or techniques described in U.S. Pat. No. 6,911,132, entitled "Apparatus for Manipulating Droplets by Electrowetting-Based Techniques," issued on Jun. 28, 2005 to Pamula et al.; U.S. patent application Ser. No. 11/343,284, entitled "Apparatuses and Methods for Manipulating Droplets on a Printed Circuit Board," filed on filed on Jan. 30, 2006; U.S. Pat. No. 6,773,566, entitled "Electrostatic Actuators for Microfluidics and Methods for Using Same," issued on Aug. 10, 2004 and U.S. Pat. No. 6,565,727, entitled "Actuators for Microfluidics Without Moving Parts," issued on Jan. 24, 2000, both to Shenderov et al., the disclosures of which are incorporated herein by reference.

In some embodiments, droplet operations are mediated by electrowetting techniques. In other embodiments, droplet operations are mediated by electrophoresis techniques. In still other embodiments, droplet operations are mediated by electrowetting techniques and by electrophoresis techniques.

In one embodiment, separations may be performed using a combination of electrowetting and electrophoresis. Electrowetting microactuation can be used to create a channel to perform electrophoresis; to deliver a sample to the channel or capture a sample fraction from channel following an electrophoretic separation. For example, for forming a channel, electrowetting can be used to deform (stretch) a droplet of separation medium in a long thin shape followed. In some cases, the channel may be polymerized, e.g., using UV polymerization. In other cases, the channel may be formed by using droplet operations to add droplets into a physically confined microchannel. In a related embodiment, the effective length of an electrophoresis channel can be increased by capturing the fraction of interest in a droplet at the output and then returning it to the input in a cyclical fashion. Using the same principle, a series of progressively finer separation can be performed. Separations may also be accomplished using multiple different separation mediums at the same time.

Droplet splitting or dividing of droplets generally involves separating a droplet into two or more sub-droplets. In some cases, the resulting droplets are relatively equal in size.

Transporting involves moving a droplet from one location to another in any direction. Droplets may be transported on a plane or in three dimensions. It will be appreciated that a variety of droplet operations, such as dispensing and/or splitting may include a transporting element, in which on droplet is transported away from another droplet.

Merging involves combining two or more droplets into a single droplet. In some cases, droplets of relatively equal size are merged into each other. In other cases, a droplet may be merged into a larger droplet, e.g., combining droplet with a larger volume present in a reservoir.

Mixing a droplet involves various droplet manipulations, such as transporting or agitating, that result in a more homogenous distribution of components within the droplet. In one mixing embodiment, a droplet positioned over an electrowetting electrode is rapidly and cyclically deformed in place by activating and deactivating the electrode, inducing fluid currents within the droplet which facilitate mixing. Frequency-dependent effects such as mechanical resonances may be used to tune the quality and speed of mixing. Compared to techniques which require transport of droplets on a surface for mixing this approach minimizes the area required for mixing. This mixing scheme can be employed without the presence of a top plate. Due to space-saving advantage, this scheme could provide for simplified mixing in reaction wells since only one electrode is needed.

Reagents or samples from reservoirs may be dispensed as discrete droplets for transport to other locations on the droplet microactuator.

The invention includes droplet operations using droplets comprising beads. A variety of such operations are described elsewhere herein. In one embodiment, beads are used to conduct droplet operations on reagents that are prone to interfere with droplet operations. For example, certain proteins may be prone to bind to surfaces of a droplet microactuator and/or to partition into the filler fluid. Immobilizing such compounds on hydrophilic beads can be used to facilitate droplet operations using the compounds. The compounds can be bound to the beads, and the beads can contained with a droplet which is subjected to droplet operations.

In one particular dispensing operation, coagulation is used to separate serum from whole blood. Whole blood is loaded onto the chip and combined with a droplet comprising a coagulating agent. Following coagulation, droplets are dispensed from the sample. Because cells and platelets are trapped in place, the liquid dispensed from the sample will contain only serum.

8.8.6 Thermal Control

The droplet microactuator of the invention may include a means for controlling the temperature of the droplet microactuator or a region of the droplet microactuator. Among other things, thermal control is useful for various protocols requiring heating or cooling steps. Examples include amplification protocols requiring thermal cycling and various assays that require incubation steps.

8.8.6.1 Thermal Control Designs

In general, thermal control may be provided in three ways: (1) thermal control of the entire droplet microactuator; (2) thermal control of a region of a droplet microactuator using a heater that is in contact with or in proximity to the controlled region; and (3) thermal control of a region of the droplet microactuator using a heater that is integrated into the droplet microactuator (e.g., in the substrate comprising the path or array of electrodes and/or in a top plate of the droplet microactuator, when present). Combinations of the foregoing approaches are also possible. Two approaches previously discussed are illustrated in FIG. 2.

In an integrated heater approach, temperature zones can be created and controlled using thermal control systems directly integrated into the droplet microactuator. Integration of thermal control through thin-film heating elements fabricated directly on the droplet microactuator is also useful to maximize the speed, throughput and quality of amplification reactions on the droplet microactuator. Due to their small thermal mass, droplets can be thermally cycled extremely rapidly. Thermal control is enhanced by locating the heating elements proximate to the droplets and reducing the parasitic thermal losses between the heater and the droplet. Heating elements can be integrated into the top plate and/or bottom plate of the droplet microactuator.

Integrating heating elements onto the droplet microactuator also enables the use of multiple distinct thermal zones within the droplet microactuator. This permits multiple steps in an analysis, such as sample preparation and thermal cycling, requiring different temperatures to be performed simultaneously on different portions of the droplet microactuator. Droplets can be physically transported or "shuttled" between zones of different fixed temperatures to perform the thermal cycling aspects of the amplification reaction. This approach can produce even faster reactions, since heating and cooling of the entire thermal zones is no longer rate-limiting. Instead, heating and cooling rates are determined by the time required to transport the droplets between the zones and the time required for the droplet temperature to equilibrate to the temperature of the zone once it arrives within the zone, both of which are expected to be very fast. A further advantage is that reaction steps can be "queued" rather than "batched" to permit greater operational flexibility. For example, discrete samples can be continuously fed into the droplet microactuator rather being delivered at a single point in time.

Droplets may be thermally cycled in batch mode using a single heater or in flow-through mode by circulating the droplets through distinct temperatures zones created by the heating elements. The essential difference between batch and flow-through modes is that in batch mode thermal control is effected by varying the temperature of the heater while in flow-through mode, thermal cycling is effected by transporting the droplets among distinct constant temperature zones. In the "batch" method a single integrated thin-film heater on the droplet microactuator was used to thermally cycle static droplets located within the heater zone. In the "flow-through" method, two distinct fixed temperature zones were created on the droplet microactuator and thermal cycling was performed by shuttling the droplets between the two zones.

In the "batch" case, the thermal mass of the heater itself as well as thermal losses may be minimized through the use of thin-film heaters placed directly adjacent to the droplets. Because the thermal masses, including the droplet itself, are so small, rapid temperature changes can be effected. Passive cooling (in filler fluid) is also rapid because the total energy input into the system is extremely small compared to the total thermal mass.

For "flow-through" heating, a larger thermal mass is desirable because it helps to stabilize the temperature while a slower ramp rate is tolerable because the heater temperature is not varied once it reaches its set point. A flow-through system can, for example, be implemented using block heaters external to the droplet microactuator which were more accurate and easier to control than thin-film heaters although, in principle either type of heater could be used to implement either method.

In another embodiment, temperature is controlled by flowing or recirculating heated filler fluid through the chip and around the droplets.

The droplet microactuator layout is scalable, such that a droplet microactuator may include a few as one heating zone up to tens, hundreds or more heating zones.

8.8.6.2 Heater Types

Heaters may be formed using thin conductive films. Examples of suitable thin films include Pt heater wires and transparent indium-tin-oxide (ITO). ITO provides better visualization of the droplets for real-time observation. A remotely placed conventional thermocouple (TC) for temperature regulation can also be used. In one embodiment, tiny metal (e.g., copper) vias in the PCB substrate are used to create tight thermal junctions between the liquid and the remote TC. Further, sample temperature can be determined by monitoring the copper via using a surface mount thermistor or an infrared sensor. One advantage of using a thermistor is that they are small enough (2×2 mm) to be soldered directly on the droplet microactuator, while an advantage of using IR is that it is non-contact method which would simplify the interfacing. Because the thermal conductivity of copper is at least 700 times greater than the FR-4 substrate (350-390 W/m·K versus 0.3-0.5 W/m·K) the temperature of a Cu via will accurately represent the temperature inside the liquid. Heaters may be integrated on the bottom and/or top (when present) plate of the droplet microactuator and on the bottom and/or top surface of either plate, or integrated within the structure of either plate.

In one flow-through embodiment, reduced thermal gradients can be provided by using heaters to create a continuous temperature gradient across the droplet microactuator (e.g., from 100 to 50° C.). The use of a continuous gradient will eliminate the need to overcome the steep temperature gradients found along the edge of the heater blocks. A controlled temperature gradient would also significantly enhance the functionality of the device by allowing protocols with arbitrary numbers of temperature points to be implemented. Furthermore, each reaction can be performed with a custom thermal protocol while only the temperatures of the two or more blocks would need to be thermally regulated. The droplets will be transported to and held at the appropriate location between the heaters to achieve a target temperature. The fluorescence of the droplets can be imaged using a fluorescence sensor as they are transported over a detection spot. The temperature of the upper and lower target temperatures can be varied by changing the location of the droplets.

In some embodiments, heaters located above the droplets may obscure the droplets thus interfering with real-time optical measurements. In such cases, the droplets can be transported out from underneath the heaters to a location which is preferred for optical detection (i.e. a detection spot). Droplets may be periodically transported out from underneath the heaters to a detection spot on the droplet microactuator detection purposes, e.g. detection by fluorescence quantitation. Droplets may be routed into proximity with a sensor while cycling them from one temperature zone to another.

8.8.7 Droplet Microactuator Fabrication

Droplet microactuators can be made using standard microfabrication techniques commonly used to create conductive interconnect structures on microdroplet microactuators and/or using printed-circuit board (PCB) manufacturing technology. Suitable PCB techniques include those described in U.S. patent application Ser. No. 11/343,284, entitled "Apparatuses and Methods for Manipulating Droplets on a Printed Circuit Board," filed on Jan. 30, 2006, the entire disclosure of which is incorporated herein by reference. These techniques permit the droplet microactuator to be manufactured in bulk at very low cost. Low cost manufacture enables economical production of droplet microactuators, even for use as one-use disposables. Thus, the invention provides a method in which droplet microactuators are supplied to users as components of disposable cartridges for use in systems of the invention.

Designs can also be implemented on glass or silicon using conventional microlithography techniques with the capability of producing much smaller features than are typical in a PCB process. Even, for example, for a 1,572,864-reservoir droplet microactuator with 70 μm reservoir spacing and 3 fL reservoir volume, the minimum required lithographic feature size is ~0.5 μm which is well within the capabilities of conventional microlithographic techniques currently used in the semiconductor industry.

8.9 Systems

Figure 18:
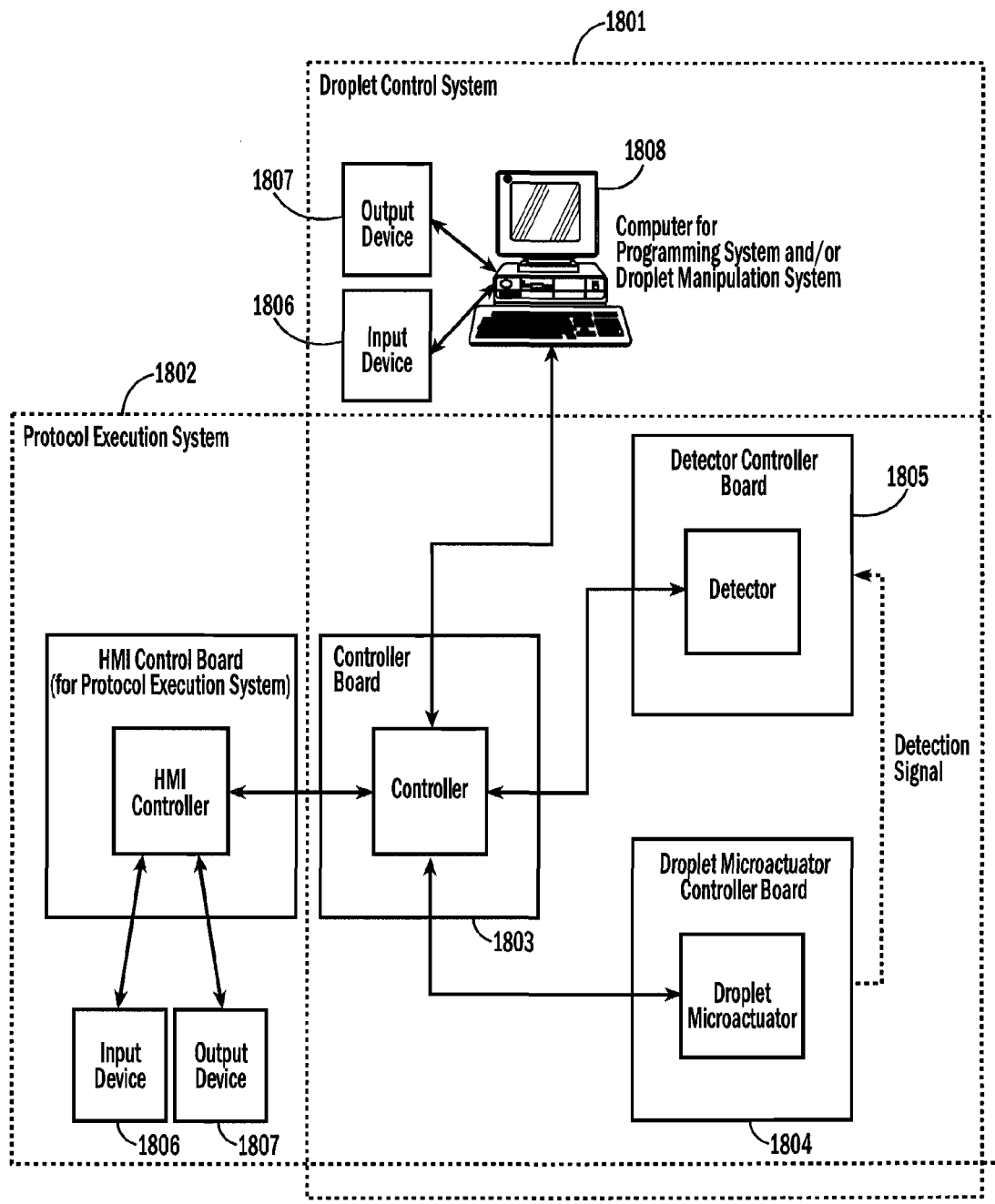
FIG. 18 is an illustration of droplet microactuator systems in accordance with an embodiment of the present invention.

Fluid loading may be accomplished using droplet microactuator systems, such as illustrated in FIG. 18. Steps of a fluid loading protocol may be conducted using a droplet control system 1801. A set of computer executable instructions may be written which can be loaded into a controller for execution of a loading protocol. Integrated systems including the droplet control system 1801 and the protocol execution system 1802 may also be used. The droplet control system 1801 permits a user to control droplet microactuator system functions, such as droplet operations and sensor operations for fluid loading protocols. The protocol execution system 1802 permits a user to execute software routines that control droplet microactuator system functions, such as droplet operations and fluid loading operations. The invention also provides a method or computer useable instructions for conducting fluid loading processes or protocols. The programmable flexibility of the platform permits assays to be rapidly optimized and allows conditional execution steps to be implemented. For example, calibrations, confirmatory tests, or additional controls can be executed if triggered by a particular test result. In some embodiments, the system can integrate sample preparation steps. Automation of the system and on-droplet microactuator operations enhance portability and enable assays to be performed more quickly and by personnel with minimal training, thereby reducing human error.

Referring further to FIG. 18, at a high level, each of the systems of the invention typically includes a processor or controller 1803, a droplet microactuator 1804, a sensor or detector 1805, input device(s) 1806, output device(s) 1807, and software. U.S. Patent Application No. 60/806,412, entitled "Systems and Methods for Droplet Microactuator Operations," filed on Jun. 30, 2006, the entire disclosure of which is incorporated herein by reference, describes droplet microactuator systems which may be employed in conjunction with the droplet microactuator aspects of the invention. The droplet control system includes droplet control software run on a computer 1808 and programmed to display a droplet control interface for controlling droplet microactuator system functions. The protocol execution system includes protocol execution software programmed to facilitate execution of a set of computer executable or computer useable instructions for controlling droplet microactuator system functions to conduct fluid loading.

8.9.1 Controller

The system of the invention may include a controller 1803. The controller serves to provide processing capabilities, such as storing, interpreting, and or executing software instructions. The controller may, for example, be comprised of a digital signal processor (DSP) with memory, a microcontroller or an application specific integrated circuit (ASIC). An example of a suitable DSP processor is the Analog Devices Blackfin DSP processor.

The controller is electronically coupled to various hardware components of the invention, such as the droplet microactuator, any sensors, and any input and/or output devices. The controller may be configured and programmed to control data and/or power aspects of these devices. For example, with respect to the droplet microactuator, the controller controls droplet manipulation by activating/deactivating electrodes. This aspect of the invention is discussed further in Section 8.8.

The controller may further be electronically coupled to a separate computer system including a processor, input and output devices, data storage medium, and other components. This arrangement is particularly useful in the droplet control system, in which the computer system is programmed to operate a droplet control user interface. In this arrangement, the processor of the computer system may accept input via the user interface and transmit instructions to the controller, e.g., to activate/deactivate electrodes, to read electrodes, memory, and/or sensors, and the like.

In the protocol execution system, software for controlling the system may be loaded directly into and executed by the controller to cause the controller to control the droplet microactuator system functions. In this embodiment, the system can run autonomously, e.g., as a portable or handheld system.

8.9.2 Droplet Microactuator

The system may include a droplet microactuator 1804, as described further in Section 8.8. The droplet microactuator is electronically coupled to the processor such that the processor can control various operations of the droplet microactuator, such as droplet manipulation operations.

8.9.3 Sensor

Various embodiments of the invention make use of sensors or detectors 1805. Sensors may include sensors which are coupled to the droplet microactuator for the purpose of measuring parameters of interest on the droplet microactuator such as the fluorescent or luminescent intensity at a location on the droplet microactuator where a reaction product may be located. Sensors may also include sensors which monitor the status of the system such as droplet microactuator insertion sensors, lid latch sensors, ambient temperature sensors and the like. Output from each sensor may be mapped to a specific memory location, and the processor must only query the mapped location to obtain a reading from the sensor. The sensor is mounted relative to the droplet microactuator and/or electronically coupled to the droplet microactuator such that the sensor can detect signals, such as electrical or light signals, from the droplet microactuator. Sensors are discussed in more detail elsewhere in this specification, e.g., see Section 8.11.

8.9.4 Input and Output Device(s)

Systems of the invention also include various input devices 1806 and output devices 1807. In certain embodiments, such as the protocol execution system, certain input and output devices may be controlled using a human-machine interface (HMI) controller.

8.9.5 Software

Each of the systems of the invention includes software. The software provided on a storage medium is one aspect of the invention. Examples of suitable storage mediums include magnetic storage, optical storage, phase-change memory, holographic storage, molecular memory storage, battery or capacitor-backed SRAM and flash memory storage. The software may be loaded in memory and/or in a processor. A system in which software of the invention is present in memory and/or a processor and/or a storage medium is also an aspect of the invention.

The software of the invention may be written in any of a variety of programming languages, such as Visual C, Java and/or Python. The system may include an interpreter for translating droplet manipulation and other instructions from the high-level language into an intermediate language for execution by the processor. Alternatively, software written according to the invention may be compiled into machine language using a compiler. The software interpreter and compiler for the language of the invention are themselves novel aspects of the invention. As such, all forms of data storage, memory, and processors containing the interpreter and/or compiler are aspects of the invention.

The system can be programmed to execute a wide variety of protocols involving any number of droplet manipulations. Multiple droplets can be independently and simultaneously manipulated on a single droplet microactuator. The capacity to independently manipulate multiple droplets in parallel enables execution of complex protocols as a series of basic microfluidic instructions. Systems are scalable and may control tens, hundreds, thousands or more parallel droplet manipulations per droplet microactuator. For example, at any one moment, up to a maximum of every control electrode on the droplet microactuator may be engaged in a droplet operation.

The system can be programmed to enable users to input instructions for the execution of protocols. Existing protocols may be monitored and adjusted according to user requirements. Complex protocols can be implemented in which the outcome of one or more steps determines the selection of one or more subsequent steps. For example, a droplet in which a certain measured result is positive may be transported for further processing, while a droplet in which a result is negative may be discarded, or vice versa.

8.9.6 Portability

Figure 19A:
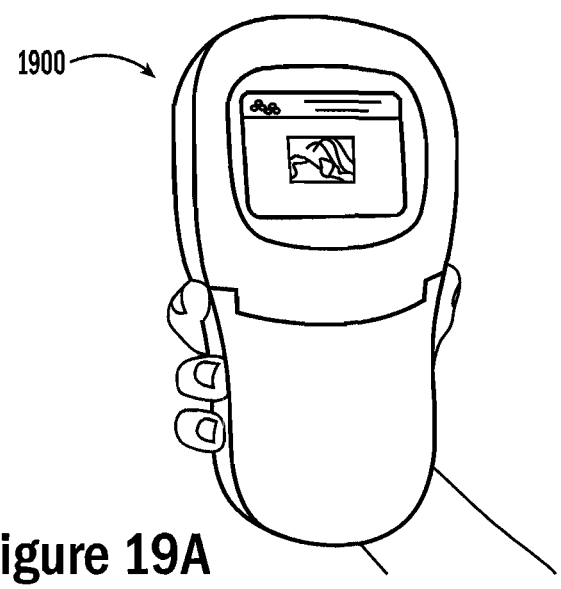
FIGS. 19A and 19B are illustrations of a portable handheld analyzer in accordance with an embodiment of the present invention.
Figure 19B:
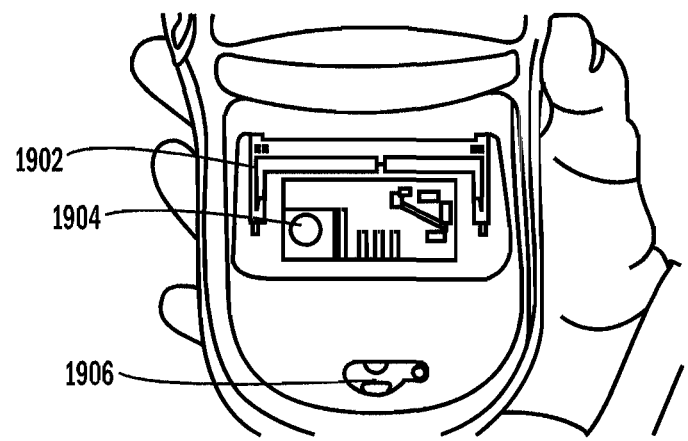

Referring to FIGS. 19A and 19B, in some embodiments, the analyzer is provided as a portable device, such as a handheld device 1900. FIG. 19A shows the exterior of handheld device 1900 and FIG. 19B shows a slot 1902 for insertion of a droplet microactuator (not shown), an optical sensor 1904 for sensing optical signals from the droplet microactuator, and a lid latch 1906, which may be coupled to the system to indicate whether the lid is open or closed. It is envisioned that the portable analyzer may also be a tabletop device. The portability of the droplet microactuator systems of the invention facilitates point of care or point of sample collection use in a wide variety of settings in clinics, operating rooms, emergency rooms, small laboratories, and in the field (emergency response teams, accidents, disasters, battlefield, bioterrorism sites etc.) for rapid diagnostics that can lead to quick turn around times in critical situations.

8.10 User Interface

The droplet control system includes droplet control software programmed to display a droplet control interface for controlling droplet operations on the droplet microactuator, controlling the sensor, when present, and controlling other hardware associated with the droplet control system. The system may also include software to facilitate creation of a set of software or computer useable instructions for controlling droplet microactuator system functions, such as droplet operations and/or sensor operations.

Figure 20:
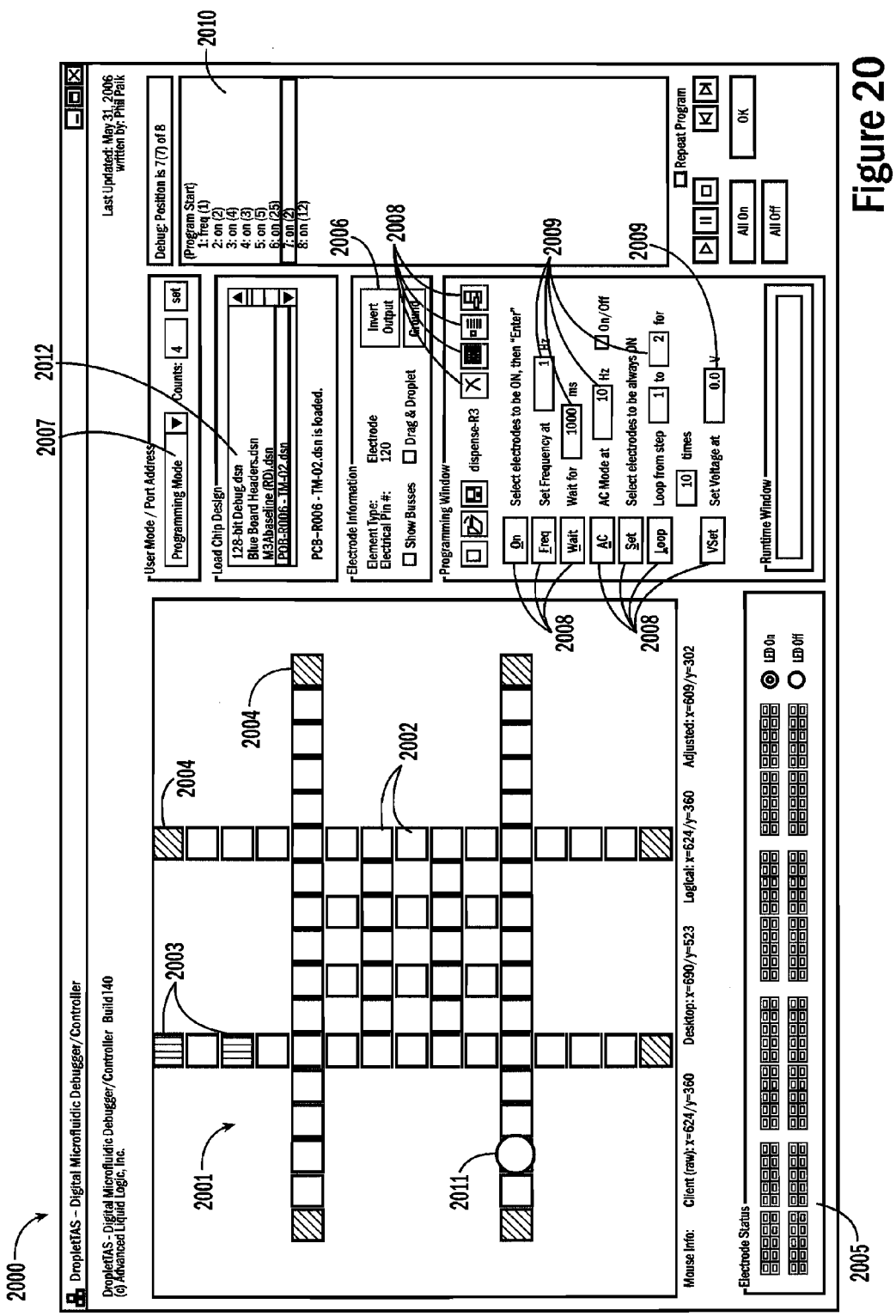
FIG. 20 is an illustration of a user interface of a droplet control system in accordance with an embodiment of the present invention.

As illustrated in FIG. 20, the system may include a user interface 2000. The user interface is described further in related U.S. Patent Application No. 60/806,412, entitled "Systems and Methods for Droplet Microactuator Operations," filed on Jun. 30, 2006, the entire disclosure of which is incorporated herein by reference. The user interface may display a map 2001, preferably an interactive map, of a droplet microactuator. The map may be used to interact directly with the droplet microactuator to manipulate droplets on the droplet microactuator to conduct a fluid loading protocol according to the invention. The map may be used in a virtual mode to manipulate virtual droplets 2011 in a programming mode to develop and record subroutines for controlling droplet microactuator functions and related hardware.

8.10.1 Droplet Control System and User Interface

The droplet control system includes droplet control software. The droplet control software is programmed to display a droplet control interface for controlling droplet operations on the droplet microactuator, controlling the sensor, when present, and controlling other hardware associated with the droplet microactuator system. The droplet control software permits a user to manipulate droplets on a droplet microactuator via a software driven user interface. As described above, an example of such an interface is illustrated in FIG. 20. Among other things, the user interface may permit a user to view information about a droplet microactuator. The user interface may also facilitate input by the user which controls functions of the droplet microactuator and associated devices, such as associated sensors.

With respect to controlling droplet operations on a droplet microactuator, the software is programmed and the system is configured to, among other things, drive control and reference electrodes on the droplet microactuator to conduct the droplet operations. Droplet operations, which are discussed further in Section 8.8 above, are effected by applying a voltage to selected electrodes. The software and system may be configured to permit software loaded in the processor to control activation of the selected electrodes by controlling the operation of relays associated with the electrodes.

As shown in FIG. 20, the user interface 2000, which is displayed on an output device, may be programmed to display a graphical illustration or map 2001 of a droplet microactuator design. The map 2001 may be based on a matrix or other configuration that defines the position of each of the control electrodes and/or reservoirs. Components of the map may be differentiated by appearance, e.g., by shape, color, brightness, symbols, icons, etc. For example, in the map displayed in FIG. 20, unactivated droplet manipulation electrodes 2002 can be shown in a first color (such as gray), activated droplet manipulation electrodes and reservoirs 2003 can be shown in a second color (such as red), and unactivated reservoirs 2004 can be shown in a third color (such as blue).

In a simple embodiment, the matrix is defined in a control file which identifies a row and column for each electrode and/or reservoir. When a control file is loaded, the system reads in the matrix definitions and displays the corresponding map of the matrix on the user interface.

The interface may display information about components of the map, which may also be stored in the control file. In one embodiment, the system displays information about a component when it is moused over, selected, or otherwise electronically identified by a user. Information displayed may, for example, include some or all of the following information:

- component type, e.g., droplet manipulation electrode, reagent reservoir, sample reservoir, etc.;
- electrical connectivity information, e.g., electrode enumeration, grounds, pinout number etc.;
- adjacency relationships, e.g., in a polygonal electrode arrangement;
- representative geometry, for rendering the map in the user interface;
- design notes and/or other comments;
- part numbers;
- column and/or row position.

The system may also record the history of the activation of each electrode, so that the user may track the number of times an electrode has been activated. History information may, for example, be displayed by mousing over or selecting an electrode. The system may be programmed to accept input from a user instructing history information to be displayed simultaneously for all electrodes.

To facilitate user interaction, a moused over or selected electrode 2002 or other component may also cause the electrode or other component to be highlighted on the droplet microactuator map. This capability permits a user who is directly controlling droplet microactuator operations to review information about each potential step by mousing over the droplet microactuator component prior to actually selecting and activating the droplet microactuator component. The system may be programmed to highlight a moused over component and a selected component differently so that a user may differentiate between the two.

The system may include a means 2007 for permitting a user to select the mode of operation, e.g., select between a virtual or programming mode in which a program can be written for controlling a droplet microactuator, and an operation mode in which droplets are controlled directly on a droplet microactuator.

The system may include a means 2012 for permitting a user to select a droplet microactuator design for display. Alternatively, data identifying the droplet microactuator design may be included as a component of the droplet microactuator assembly or cartridge accessible by the system upon coupling of the droplet microactuator assembly or cartridge to the system.

It should be noted that in some designs, more than one electrode may be coupled to the same electrical output. Such designs can be used to simplify the design of the droplet microactuator. In such designs, selecting or mousing over one electrode from a common set may result in selection, highlighting and activation of all electrodes in the set.

Thus, in one embodiment, the system is programmed so that when a user selects an unactivated electrode 2002 on a microactuator map 2001, the system activates the electrode. For example, the system may be programmed and configured so that clicking on a representation of an electrode on the map causes a voltage to be applied to a corresponding actual electrode on the droplet microactuator, thereby activating the selected electrode. In this way, a user can directly manipulate droplets on the droplet microactuator using the interface.

The droplet control system may permit a user to transport a droplet by sequentially clicking on a series of adjacent electrodes. Similarly, the system may permit a user to transport a droplet by selecting a virtual on-screen droplet 2011 and dragging the droplet to a virtual electrode at a desired location on the droplet microactuator map. Moreover, the system may permit a user to transport a droplet by selecting a virtual on-screen droplet 2011, then clicking a virtual electrode at a desired location on the droplet microactuator map. Other droplet microactuator components may be similarly controlled via a user interface.

The system may be programmed to display a representation of the electrical control lines 2005 electronically coupled to the droplet microactuator components, so that when a user mouses over and/or selects a component, the system highlights the electrical signal that is activated as a result of being mapped to the component.

The droplet microactuator may be visually monitored, e.g., using a microscope and video capture device. The user interface may be programmed to display a real-time image of the droplet microactuator from the video capture device. Further, the droplet microactuator map may be superimposed over the real-time droplet microactuator image so that a user can visualize droplet operations on the droplet microactuator as he or she interacts with the droplet microactuator via the user interface.

Similarly, the system may be programmed to display virtual droplets 2011 on the droplet microactuator map which illustrate actual behavior of droplets on a droplet microactuator which is being controlled by the system, and/or the system may be programmed to display virtual droplets 2011 on the droplet microactuator map which illustrate predicted behavior of droplets on a droplet microactuator, even though a droplet microactuator is not being directly controlled by the system.

The system may also be programmed to effect an "inverse output" 2006 operation. In typical operation, the droplets are constantly connected to a ground voltage/ground line. In the "inverse output" operation, the signals are inverted so that the droplet is at a high voltage and the electrodes are activated by setting them to ground potential. In other words, the "inverse output" operation switches the polarity of the signals.

The system may also facilitate creation of a set of software or computer useable instructions for controlling droplet operations on the droplet microactuator and controlling other functions of a droplet microactuator and related hardware. The software instructions may, for example, include instructions for executing a protocol for processing and analyzing a sample and outputting results of the analysis. The system may facilitate writing programs for controlling droplet microactuator functions and related components, such as sensor components without interacting with an actual droplet microactuator.

The system may, for example, include means for permitting a user to create a program with a set of instructions for execution by the droplet microactuator. Examples of suitable instructions include:

- "on" for identifying electrodes that are to be actuated;
- "frequency" to set the rate at which the steps are executed, e.g., the timing of electrode activation/deactivation;
- "wait" to permit the instructions to pause for a predetermined period;
- "loop" to loop steps in the program;
- "voltage" to set the voltage being applied to the outputs.

Instructions can be provided as a byte-coded language which includes instructions needed to conduct droplet manipulations and control other aspects of the system. The instructions prepared by the system can be recorded in the assembly language and assembled into byte codes. The byte codes can be loaded into a system of the invention, e.g., a protocol execution system, for execution. The system may include a software interpreter for interpreting the language for execution, e.g., in a protocol execution system.

In a preferred embodiment, the system displays a series of buttons or icons 2008 that can be selected to add, insert, update, modify or delete instructions from a subroutine. The buttons or icons may, as appropriate, be accompanied by fields 2009 for the entry of parameters associated with the instructions. For example, by clicking the "add" button, a command can be added at the end of a subroutine. By clicking an "insert" button, a command can be inserted within a subroutine. By clicking a "modify" button, a command present in a subroutine can be modified. By clicking a "delete" button, a command can be deleted. Further, a display field 2010, which may be editable, may be included for viewing, entering and/or editing code.

The system may display a simulated execution of a subroutine on the droplet microactuator map, which outputs to the user a visual display of the effects of the command series selected. In other words, in a simulated execution mode, the software executes the steps of a subroutine but does not send an electrical signal to the droplet microactuator. In a preferred simulation mode, simulated droplets are displayed on the screen to illustrate to the user the actual effect of the program. In this way, a user can readily troubleshoot a subroutine without requiring interaction with a droplet microactuator.

8.10.2 Protocol Execution System and User Interface

The invention provides a protocol execution system. The protocol execution system includes protocol execution software programmed to facilitate execution of a set of software instructions for loading fluid, controlling droplet operations on the droplet microactuator and/or other functions of a droplet microactuator and related hardware. The protocol execution system provides the ability to execute protocols on a free-standing system, typically a portable or handheld system.

The protocol execution system is configured to control the droplet microactuator and any associated components. Preprogrammed instructions may be loaded into the controller which controls the system and any associated components. The protocol execution system may include various components for permitting a user to provide input to and obtain output from the processor. The human-machine interface may be facilitated using a HMI board. The HMI board typically includes a controller and various electronic components, such as buses and ports for electronically coupling input and output devices with the processor.

8.11 Sensors

The droplet microactuators and systems include sensors for measuring droplet properties, such as physical properties, chemical properties, and electrical properties. In some embodiments, the sensors will include a sensing element arranged to interact with a droplet and/or a signal from a droplet; a transducing element, which converts output from a sensor into a measurable signal; a means for transmitting the signal to the processor. The processor may convert the signal into an output recognizable to a user.

The sensor element may be a component of the droplet microactuator, e.g., mounted on a top or bottom plate, positioned in the interior space of a droplet microactuator between top and bottom plates, or manufactured as an integral component of the droplet microactuator, e.g., an integral component of top or bottom plates. In other embodiments, the sensor element may be exterior to the droplet microactuator but arranged within the system in a manner which permits the sensor to receive a signal from on the droplet microactuator, e.g., from a droplet on a droplet microactuator. For example, a sensor element for sensing photons may be arranged to receive photons from a droplet on a droplet microactuator. Where the system has a top plate capable of transmitting photons from a droplet, the sensor may be arranged in proximity to the top plate for sensing the photons. Where the system has a top plate not capable of transmitting photons from a droplet, the top plate may be provided with a window capable of transmitting photons, and the sensor may be arranged in proximity to the window for sensing the photons.

Illustrative examples of sensor configurations are provided in FIGS. 21A-21D wherein the sensors may be provided in association with a bottom plate 2102, a top plate 2104, and electrodes 2106. FIG. 21A illustrates an optical sensor which may include use of a setup including an LED 2108 and a photodiode 2110 for monitoring absorbance. FIG. 21B illustrates a luminometric sensor which may include use of a photomultiplier tube (PMT) 2112. FIG. 21C illustrates a potentiometric sensor 2114 which typically functions based on the measurement of a potential under no current flow. FIG. 21D illustrates an amperometric sensor 2116 which typically functions by the production of a current when a potential is applied between two electrodes.

It is important to keep in mind that, as noted elsewhere in this disclosure, the droplet microactuator may be supplied as a separate component which can be coupled to a system by a user. Where sensors are exterior to the droplet microactuator, those sensors may in some embodiments be aligned such that upon coupling to the droplet microactuator system, the sensing elements are appropriately aligned to detect signals from the droplet microactuator, e.g., the photon sensor is aligned with the appropriate window and/or with the appropriate location on the droplet microactuator where the sensing step will be accomplished in the course of a droplet protocol.

In various embodiments, the droplet microactuator and/or system may be configured with sensor components enabling the implementation of one or more types of sensing. Examples of suitable sensing types include physical sensing, electrochemical sensing, and optical sensing.

8.11.1 Physical Approaches

A droplet microactuator and/or system of the invention may include one or more physical sensors arranged to sense a property of a droplet on a droplet microactuator. Examples of physical sensing include temperature and droplet size (e.g., by thermally measuring the footprint of the droplet).

8.11.2 Electrochemical Approaches

The droplet microactuator system of the invention makes use of a variety of optical detection approaches. A droplet microactuator and/or system of the invention may include one or more electrochemical sensors arranged to sense a property of a droplet on a droplet microactuator. Examples of suitable electrochemical sensing types include potentiometric sensors, amperometric sensors, voltametric sensors, and conductometric sensors. The various components of the sensors (e.g., electrodes, counter electrodes, reference electrodes, etc.) may be provided on the same or separate substrates, arranged to permit contact with a droplet on the droplet microactuator. For example, in embodiments in which the droplet microactuator includes two substantially parallel substrates, various components of the sensor assemblies may be comprised on one or both of the substrates. In some embodiments, an electric circuit may be used to amplify signals into a measurable voltage. Various aspects of these approaches are discussed in the ensuing sections.

8.11.2.1 Amperometry Sensor

The droplet microactuator device or system may include an amperometry sensor and an electrical source arranged to permit a droplet on the droplet microactuator to be transported into contact with electrical source and the sensor to permit detection of electric current flowing through the droplet.

8.11.2.2 Potentiometry Sensor

The droplet microactuator device or system may include a potentiometry measuring and reference electrode arranged to permit a droplet on the droplet microactuator to be transported into contact with the measurement and reference electrodes to permit measurement of equilibrium electrode potential of a droplet.

8.11.3 Optical Approaches

The droplet microactuator system of the invention makes use of a variety of optical detection approaches.

A droplet microactuator and/or system of the invention may include one or more optical sensors arranged to sense a property of a droplet on a droplet microactuator. Examples of optical sensing include absorbance, chemiluminescence, and fluorescence. Optical sensors may in some cases be accompanied with an appropriate light source, e.g., for exciting fluorescence or conducting absorbance measurements. These sensors may be provided as components mounted on a droplet microactuator and/or as integral parts of a droplet microactuator, e.g., using semiconductor manufacturing techniques.

Optical sensors may include various optics designed to direct optical signals, and may be coupled to various image processors for analyzing optical images. For example, droplet size may be detected by processing an image of a droplet. Similarly, droplet size may be obtained by measuring a thermal footprint of the droplet. Electrical sensors may also be used to measure droplet size, e.g., by measuring impedance of the droplet footprint.

In some cases, surfaces of the droplet microactuator may be modified to enhance optical sensing. For example, electrodes with reflective surface finishes may be used to facilitate optical measurements of droplets. The use of reflective electrodes increases the path length for absorbance measurements and is also compatible with reflectance spectroscopy. For auto-fluorescent substrates, such as PCB, coating a droplet microactuator surface with a non-fluorescent coatings can be used to provide a non-fluorescent detection zone.

Various aspects of these approaches are discussed in the ensuing sections.

8.11.3.1 Photosensor

The droplet microactuator device or system may include an absorbance detection components including a light source and a photosensor arranged to permit a droplet on the droplet microactuator to be transported into proximity with the light source and photosensor such that light or energy passing through the droplet can be detected by the photosensor.

The droplet microactuator device or system may include chemiluminescence detection components including a photosensor (such as a photodiode, avalanche photodiode, photomultiplier tube) or photon sensor (such as a photon-counting photomultiplier tube) arranged to permit a droplet on the droplet microactuator to be transported into proximity with the photosensor or photon sensor such that photons emitted by chemical species in the droplet can be detected by the photosensor or photon sensor.

8.11.3.2 Fluorescence Sensor

The droplet microactuator device or system may include fluorescence detection components including a light excitation source with appropriate filters, if necessary, and a photosensor (such as a photodiode, avalanche photodiode, photomultiplier tube) or a photon sensor (such as a photon-counting photomultiplier tube) with appropriate filters and dichroic mirrors, if necessary, arranged to permit a droplet on the droplet microactuator to be transported into proximity with the light excitation source and the photosensor or photon sensor such that photons emitted by fluorescent species in the droplet can be detected by the photosensor or photon sensor.

8.11.3.3 Surface Plasmon Resonance

In another embodiment, surface plasmon resonance (SPR) sensing is employed to detect interactions between an antibody and any target analyte. SPR sensing is useful to detect and quantify such interactions. Typically, one interactant in the interactant pair (i.e., antibody or analyte) is immobilized on an SPR-active gold surface on a glass substrate. The interactant may be immobilized using a droplet-based approach wherein a droplet is transported into contact with the gold surface to deposit the interactant thereon. A droplet including the other interactant may be transported into contact with the immobilized interactant, thereby permitting the other interactant to bind to the immobilized interactant. When light (e.g., visible or near infrared) is directed through the glass substrate and onto the gold surface at angles and wavelengths near the surface plasmon resonance condition, the optical reflectivity of the gold changes very sensitively with the presence of biomolecules on the gold surface or in a thin coating on the gold. The optical response may be highly sensitive due to the fact that it involves an efficient, collective excitation of conduction electrons near the gold surface. The extent of binding between the solution-phase interactant and the immobilized interactant may be observed and quantified by monitoring this reflectivity change. The invention also includes a droplet microactuator including a gold surface thereon, and a path or network of electrodes arranged to permit the execution of droplet manipulations sufficient to bring a droplet into contact with the gold surface. Further, the invention includes a system including such droplet microactuator and further including a light source capable of directing light onto the gold surface at angles and wavelengths near the surface plasmon resonance condition. Similarly, the invention includes a system including such a droplet microactuator and further including a means for detecting changes in reflectivity of the gold surface. Moreover, the invention includes a droplet microactuator device and/or system having loaded thereon reagents sufficient to conduct some or all steps of an SPR protocol.

8.11.3.4 Raman Spectroscopy

In one embodiment, the droplet microactuator and/or system includes Raman spectroscopic detection capability. In general, this capability includes a Raman signal-generating light source, a Raman signal detection surface, and a Raman spectrophotometer.

The Raman signal generating light source may, for example, be a monochromatic light, e.g., a laser source with excitation in the visible wavelength range. The light source is arranged to irradiate a Raman signal detection surface on a droplet microactuator. The surface may, for example, be a surface of the droplet microactuator and/or a surface of a particle on a droplet microactuator. For example, the surface may be the surface of a particle in a droplet on a droplet microactuator. The droplet microactuator may have the capability of conducting droplet operations using a droplet including such particles in order to effect various protocols which employ Raman signal detection methods.

The Raman signal detection surface may include any surface appropriate for Raman scattering. Examples include gold or silver surface. The surface may be roughened. The droplet microactuator may in some cases include multiple metallic surfaces (e.g., surfaces of the droplet microactuator, beads, particles, nanoparticles, etc.), including surfaces labeled with a different Raman reporter molecules. Antibodies or analytes bound to the surface may be identified by the characteristic Raman spectra of the Raman reporter molecules. The Raman detection surface may, for example, be an electrode, a coating on the electrode, or a layer on any chip surface. In operation, a droplet is positioned using droplet operations on the Raman detection surface, and is irradiated with a laser beam. Scattered light from the irradiated surface is collected with a spectrometer. In another embodiment, the Raman detection surface is a particle in a droplet on a droplet microactuator. The particle may, for example, be a nanoparticle, such as a silver or gold nanoparticle. For example, silver nanoparticles can be prepared as monodispersed colloidal suspensions, which can be manipulated on a droplet microactuator using droplet operations. In some embodiments, the particles may be aggregated into clusters using aggregation additives, such as inorganic salts such as sodium chloride or sodium nitrate, acids such as nitric or hydrochloric or organic amines such as poly-L-lysine. These aggregation additives can be combined with a droplet including the sample and the particles using droplet operations, e.g., using droplet operations to combine a droplet including the aggregation additive with a droplet including the particles and sample. Surfaces of the droplet microactuator associated with the Raman spectroscopic region are selected to minimize the background fluorescence signal.

A Raman spectrophotometer is arranged to detect Raman scattered light emitted from the sample droplet. The Raman spectrophotometer may be integral with the droplet microactuator arranged exterior to the droplet microactuator in a manner which permits it to detect Raman scattered light emitted from the sample droplet on the droplet microactuator.

In operation, a droplet microactuator is provided having a Raman detection surface thereon. An analyte is brought into association with the Raman detection surface using droplet operations. The surface is irradiated with a Raman signal generating light source. Raman scattered light signals are detected correlated with expected signals in order to determine the identity and/or quantity of an analyte.

In another embodiment, surface-enhanced Raman scattering (SERS) is employed to detect interactions between an antibody and any target analyte. In general, this method involves monitoring an analyte mediated binding event in a sample droplet which includes the analyte, a specific binding member, a Raman-active label, and is in contact with a surface, such as a bead or a surface of the droplet microactuator, and which is capable of inducing a surface-enhanced Raman light scattering. The sample droplet is illuminated with a radiation sufficient to cause the Raman-active label in the test mixture to emit a detectable Raman spectrum. The differences in the detected surface-enhanced Raman scattering spectra are dependent upon the quantity of the analyte present in the test mixture. The presence and/or quantity of the analyte in the sample droplet may be determined by monitoring the Raman scattering spectra. The invention includes a droplet microactuator device and/or system having loaded thereon reagents sufficient to conduct some or all steps of an SERS protocol. P In a related embodiment, the invention provides a method for determining the presence or quantity of an analyte in a sample droplet by monitoring an analyte-mediated ligand binding event on a droplet microactuator. The method generally includes reacting the analyte with an antibody coupled to a Raman active label. The reaction is conducted using droplets on a droplet microactuator and is effected under conditions permitting specific binding of the antibody to the analyte, if present, to yield a first complex in the sample droplet. Sequentially or simultaneously the first complex is contacted with a surface capable of inducing a surface-enhanced Raman light scattering and having attached thereto an antibody specific for the analyte to form a second complex. The second complex is illuminated with a radiation sufficient to cause the Raman-active labels in the complex to produce a detectable Raman spectrum. Differences in the surface-enhanced Raman scattering spectra are indicative of the presence and/or quantity of the analyte present in the test mixture.

A variety of surfaces may be appropriate for the droplet-based SERS protocols of the invention. Examples include roughened metal electrodes, aggregated, films, metal islands of different morphology, semicontinuous films near the percolation threshold, and vacuum-evaporated nanostructured metal films. Accordingly, the invention includes a droplet microactuator including an SERS substrate. The droplet microactuator is suitably arranged such that a droplet may be transported along a path or network of electrodes into contact with the SERS substrate.

In DNA detection methods of the invention, a Raman label may be used. A label may be a non-sequence specific intercalator or a specific label covalently attached to a unique probe sequence. Negatively charged labels may require the use of a charge neutralizing agent, such as spermine, to facilitate association of the label with a negatively charged surface, such as silver nanobeads with a citrate surface layer. Aggregating agents may also be used in order to improve signal. Spermine may also serve as an aggregating agent.

8.11.3.5 Multisensor Capabilities

Preferred sensors are sensors for detecting absorbance, fluorescence, chemiluminescence, as well as potentiometric, amperometric, and conductometric sensors. The droplet microactuator device and/or system of the invention includes one or more of these detection capabilities. In one embodiment, a droplet microactuator includes components for facilitating 2 or more of these detection methods on a single droplet microactuator. In another embodiment, the droplet microactuator includes one detection module, but the system is programmed to conduct more than one test using the module. In this embodiment, processed sample droplets requiring testing are sequentially moved into position for testing. Thus, multiple samples may be multiplexed over a detection spot where a single sensor is used.

8.11.4 Sensor Electronics

The detection capabilities may be provided as one or more components of a sensor board. The sensor board may include one or more sensors. The sensor board may include additional electronic circuitry such as amplifiers, A/D converters, readout circuits and the like for conditioning or amplifying the signal received from a droplet. The sensor board may include control elements or other off-droplet microactuator components of the detection protocol, such as control of motors for moving components of the system.

In one embodiment, the sensor board includes a servo motor controller for controlling a servo motor that moves a magnetic field source into and out of proximity with the droplet operation surface, thereby applying/removing the magnetic field to/from the droplet microactuator. This embodiment is useful for manipulating magnetically responsive materials. The sensor board may also include power supply elements and communication elements, including without limitation, elements required to electronically couple the sensor components or control components of the board to the processor.

The optical detection location may include specialized coatings, electrode designs, or other features that facilitate optical detection. For example, the detection spot may include a specialized pad and/or coating that facilitates its operation as a background surface for optical measurement.

In certain embodiments, such as nucleic acid amplification applications, the preferred optical detection method is fluorescence quantitation. In such embodiments, the detection spot may be selected to shield background fluorescence present in the microactuator substrate or coatings disposed on the microactuator substrate. For example, in one embodiment, the microactuator is comprised of a printed circuit board substrate and the detection spot is comprised of a gold pad which shields the background fluorescence of the substrate from the sensor thereby facilitating fluorescent measurement of a droplet positioned on the pad. The pad may be formed in a metal layer disposed directly on the substrate or disposed on an intervening layer disposed on the substrate.

Preferably, the metal layer in which the pad is formed should be disposed on top of any layers exhibiting significant background fluorescence. In one embodiment the pad is disposed directly on a printed circuit board substrate being formed in the same metal layer as the electrodes for controlling the droplet. In this embodiment, the dielectric material (which may also exhibit background fluorescence) may be disposed above the metal layer and is selectively removed from the detection pads, but not the control electrodes.

Thus, a low background fluorescence detection spot may be achieved through a combination of selective removal of fluorescent material above the detection pad and optical shielding of fluorescent material located below the pad. The pad is preferably designed to minimize its interference with other droplet microactuator functions. In the embodiment described above, the pad may be formed in the same metal layer as the control electrode but is separate and electrically distinct from the control electrodes. The pad therefore 8.11.5 Detection Approaches The invention provides a variety of approaches for sensing/detecting signals or attributes of droplets. Many of these approaches are described elsewhere in this specification. This section describes additional approaches that may be useful in various settings.

An advantage of the droplet microactuator approach of the invention includes the ability to decouple reaction steps in a particular assay. Many biochemical assays use common end reactions to generate a color, light or other detectable quantity. Droplet-based protocols of the invention can be used to combine the assay droplet with a droplet containing the end reaction reagents at the point of detection. Decoupling of the assay steps permits each to be separately optimized and separation of the steps in time provides greater flexibility when one of the reaction steps is rate limiting. For example chemiluminescence assays typically have better results at a basic pH. For an assay which is optimal at an acidic pH assay reaction can be completed first at the acidic pH, and the light generation aspect of the reaction can be performed at a basic pH.

The droplet microactuators of the invention are useful in the study of rate kinetic reactions. Sample droplets can be periodically dispensed from a reservoir in which a reaction is occurring. The droplets can then be individually analyzed to determine the time course of the reaction. The droplets can be analyzed in real-time or mixed with another reagent for later analysis. Electrowetting may also be used to rapidly mix droplets for the purpose of studying fast reaction kinetics.

Changes in viscosity of a droplet can be measured as a means for assessing the state of a chemical reaction inside the droplet. For example, a coagulant can be added to a droplet of blood followed by transporting the droplet and monitoring of the ease of transport of the droplet. Greater degrees of coagulation would make transport of the droplet more difficult which can be detected as used as a measure of the degree of coagulation.

Preferred sensors include optical sensors for sensing optical signals, such as absorbance, fluorescence, and chemiluminescence, and electrochemical sensors for sensing electrochemical properties, such as potentiometric properties, amperometric properties, conductometric properties. Accordingly, the droplet microactuator system of the invention includes components arranged to facilitate detection of one or more of these properties. In one embodiment, 2 or more of these properties are detected on one or more droplets on a single droplet microactuator or otherwise accomplished using a single droplet microactuator system. In another embodiment, the droplet microactuator includes one sensor of a particular type, and the system is programmed to conduct more than one test using the sensor. In this embodiment, processed sample droplets requiring testing are sequentially moved into position for testing, i.e., moved into sufficient proximity to the requisite sensor to enable detection. Thus, multiple samples may be multiplexed over a detection spot for detection by a single sensor. Multiple sensor types may be supplied on a single droplet microactuator using this approach.

The droplet microactuator system may in some embodiments be configured to deposit a droplet or sample to a location that is exterior to the droplet microactuator for detection. For example a droplet including (or potentially including) an analyte can be deposited on a substrate for MALDI-TOF analysis.

Droplets can be cyclically transported past a common detection point in proximity to an appropriate sensor to allow multiple reactions to be simultaneously monitored. For example the droplet microactuator can include two or more "tracks" that connect high and low temperature zones in a flow-through PCR reaction chamber. A single detector is placed at the intersection of the tracks. Droplet traffic can be timed to cause droplets to sequentially pass over the detection spot.

Examples of assays suitable for execution in the droplet-based protocols of the invention on the droplet microactuator of the invention include optical assays, such as absorbance assays, fluorescence assays, bioluminescence assays and chemiluminescence assays; and electrochemical assays, such as potentiometric assays, amperometric assays, and conductometric assays. For example, various combinations of one or more of the foregoing assay types can be used to identify and/or quantify one or more analytes, such as proteins, enzymes, nucleic acids, metabolites, electrolytes, gasses (e.g., blood gases) and hematocrit. A system of the invention may be programmed to conduct on a single droplet microactuator various combinations of these assay types.

In one embodiment, a single droplet microactuator or system includes detection capabilities for 2, 3, 4, 5, 6 or more different kinds of assays. For example, the droplet microactuator device, system and/or other components of a droplet microactuator system may separately or together include one or more detection components, such as components for amperometry, potentiometry, conductometry, absorbance, chemiluminescence, fluorescence, and/or temperature. Further, a droplet microactuator system may be programmed to execute assay protocols for conducting 2, 3, 4, 5, 6 or more different kinds of assays on the same or multiple samples or sample types.

Within the droplet microactuator, the droplet manipulation components and the detection components may in some embodiments be decoupled by providing them on separate substrates. Similarly, various detection components may be provided as part of a droplet microactuator device or system, but separate from the droplet microactuator. Thus, for example, a sensor may be provided on a cartridge to which the droplet microactuator is coupled. The coupling is arranged so that when the droplet microactuator is coupled to the cartridge, suitable components are aligned to permit detection. Thus, for example, a photon sensor may be aligned with a window or other transparent substrate so that when the droplet microactuator is properly mounted on the cartridge, photons emitted from a droplet on the droplet microactuator may pass through the window or substrate for detection by the photon sensor. Similarly, where a light source is necessary to cause fluorescence of a molecule in a droplet on the droplet microactuator, the light source may be mounted to the cartridge or other component of the droplet microactuator device or system and aligned so that the light source can reach the droplet to produce the desired fluorescence.

In one embodiment, the droplet microactuator includes electrodes for performing electrochemistry. Electrodes can be patterned onto the electrowetting substrate to permit electrochemical measurement of droplets in contact with the electrodes. In a two-substrate droplet microactuator, the electrodes for performing electrochemistry can be formed either or both substrates. In some embodiments, transport electrodes and electrochemical measurement electrodes are provided on different substrates. The electrodes may include membranes for fabricating ion-selective analyses.

8.12 Other Methods

The invention includes a method in which components of a bench-top system are offered to or provided to a customer in exchange for consideration. In one embodiment, the components offered to or provided to the customer do not include the PC. The software of the invention may be provided to the user on a storage medium or made available for download via a network, such as the Internet. The user may obtain other components of the system, couple the components to a PC, load the software on a PC, and thereby assemble system of the invention.

The invention includes a method in which a bench-top system is used to generate code for executing a protocol. Code is uploaded into a separate system, such as a portable or handheld system, which is offered to or provided to a customer in exchange for consideration. The user may use the system for executing the protocol.

The invention also includes a method in which programming and/or system control is effectuated remotely via a network, such as a telephone system or the internet. Thus, for example, a system may be sold to a user, a programmer may connect to the system via a user interface displayed via the Internet to control the system, create programs using the system, load programs on the system, and/or repair programs on the system. As another example, the invention includes a process whereby a remote user accesses a droplet microactuator via a network and performs one or more droplet manipulations on the system.

8.13 Kits

A further aspect of the invention is a kit including reagents, sample collection devices, and/or a droplet microactuator or cartridge for conducting the methods of the invention.

8.14 Concluding Remarks

The foregoing detailed description of embodiments refers to the accompanying drawings, which illustrate specific embodiments of the invention. Other embodiments having different structures and operations do not depart from the scope of the present invention.

As will be appreciated by one of skill in the art, the present invention may be embodied as a method, system, or computer program product. Accordingly, the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present invention may take the form of a computer program product on a computer-usable storage medium having computer-usable program code embodied in the medium.

Any suitable computer useable medium may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include some or all of the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission medium such as those supporting the Internet or an intranet, or a magnetic storage device. Note that the computer-usable or computer-readable medium may even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device.

Computer program code for carrying out operations of the present invention may be written in an object oriented programming language such as Java, Smalltalk, C++ or the like. However, the computer program code for carrying out operations of the present invention may also be written in conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through a local area network (LAN) or a wide area network (WAN), or the connection may be made to an external computer (for example, through the Internet using an Internet Service Provider).

The present invention is described with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

This specification is divided into sections for the convenience of the reader only. Headings should not be construed as limiting of the scope of the invention.

It will be understood that various details of the present invention may be changed without departing from the scope of the present invention. Furthermore, the foregoing description is for the purpose of illustration only, and not for the purpose of limitation, as the present invention is defined by the claims as set forth hereinafter.

We claim:

1. A method of splitting a droplet, the method comprising:
   (a) providing a droplet microactuator comprising a droplet comprising beads, wherein the droplet actuator comprises:
     (i) a first substrate comprising electrodes configured for manipulating a droplet on a surface of the substrate; and
     (ii) a second substrate arranged relative to the first substrate and spaced from the surface of the first substrate by a distance sufficient to define a space between the first substrate and second substrate, wherein the droplet is situated in the space between the first substrate and second substrate;
   (b) immobilizing the beads; and
   (c) conducting one or more droplet operations to divide the droplet to yield a set of droplets comprising:
     (i) a droplet comprising the beads; and
     (ii) a droplet substantially lacking the beads.

2. The method of claim 1 wherein the second substrate is arranged in a substantially parallel relationship to the first substrate.

3. The method of claim 1 wherein the starting droplet comprises a sample droplet having a volume which is less than about 100 µL.

4. The method of claim 1 wherein the starting droplet comprises a sample droplet having a volume which is less than about 50 µL.

5. The method of claim 1 wherein the starting droplet comprises a sample droplet having a volume which is less than about 25 µL.

6. The method of claim 1 wherein the beads have a diameter ranging from about 0.1 nm to about 25 mm.

7. The method of claim 1 wherein the immobilizing comprises attracting the beads prior to step 1(c).

8. The method of claim 1 wherein the immobilizing comprises using a physical object to block transport of the beads during a droplet operation.

9. The method of claim 1 wherein:
   (a) the beads comprise substantially non-magnetically responsive beads; and
   (b) the immobilizing step is achieved by using a physical object to block transport of the substantially non-magnetically responsive beads during a droplet operation.

10. The method of claim 1 wherein:
    (a) the beads comprise magnetically responsive beads; and
    (b) the immobilizing step is accomplished by exposing the magnetically responsive beads to a magnetic field.

11. The method of claim 10 wherein the immobilizing comprises using a magnetic field in of sufficient strength to generally restrain the location of the magnetically responsive beads during the droplet operation.

12. The method of claim 10 comprising using a surfactant to prevent or reduce bead aggregation.

13. The method of claim 10 wherein step 11(b) comprises situating a droplet comprising the beads in proximity with a means for effecting a magnetic field in proximity to one or more of the electrodes, wherein the strength and proximity of the magnetic field is sufficient to immobilize magnetically responsive beads during execution of a washing protocol.

14. The method of claim 13 wherein the means for effecting a magnetic field comprises an electromagnet and a means for controlling power supply to the electromagnet.

15. The method of claim 13 wherein the means for effecting a magnetic field comprises a magnet and a means for moving the magnet into and out of proximity with the one or more of the electrodes.

16. The method of claim 1 wherein the droplet of 1(c)(i) comprises more than 99% of beads present in the combined droplet.

17. The method of claim 1 wherein the droplet of 1(c)(i) comprises more than 99.9% of beads present in the combined droplet.

18. The method of claim 1 wherein the droplet of 1(c)(i) comprises more than 99.999% of beads present in the combined droplet.

19. The method of claim 1 wherein step 1(c) comprises one or more electrode-mediated droplet operations.

20. The method of claim 1 wherein step 1(c) comprises one or more electrowetting-mediated droplet operations.

21. The method of claim 1 wherein step 1(c) comprises one or more dielectrophoresis-mediated droplet operations.

22. The method of claim 1 wherein the droplet operation comprises splitting, transporting, and/or dispensing.

* * * * *